United States Patent
Hardy et al.

(10) Patent No.: US 11,512,094 B2
(45) Date of Patent: Nov. 29, 2022

(54) FUROXAN-BASED COMPOUNDS AND USES THEREOF

(71) Applicant: University of Massachusetts, Boston, MA (US)

(72) Inventors: Jeanne A. Hardy, Amherst, MA (US); Penchala Narasimharao Meka, Mishawaka, IN (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 16/960,470

(22) PCT Filed: Jan. 11, 2019

(86) PCT No.: PCT/US2019/013201
§ 371 (c)(1),
(2) Date: Jul. 7, 2020

(87) PCT Pub. No.: WO2019/140194
PCT Pub. Date: Jul. 18, 2019

(65) Prior Publication Data
US 2020/0339596 A1    Oct. 29, 2020

Related U.S. Application Data

(60) Provisional application No. 62/616,160, filed on Jan. 11, 2018.

(51) Int. Cl.
*C07D 498/04*    (2006.01)
*C07D 519/00*    (2006.01)

(52) U.S. Cl.
CPC ......... *C07D 498/04* (2013.01); *C07D 519/00* (2013.01)

(58) Field of Classification Search
CPC ............... C07D 498/04; C07D 519/00; A61K 31/4245; A61K 31/497; A61K 31/506
See application file for complete search history.

(56) References Cited

FOREIGN PATENT DOCUMENTS

WO    WO 2017/167989 A1 * 10/2017
WO    WO-2019140194 A1    7/2019

OTHER PUBLICATIONS

Ulrich, Crystallization, Kirk-Othmer Encyclopedia of Chemical Technology, pp. 1-7, 2002.*
Vippagunta et al., Crystalline Solids, Advanced Drug Delivery Reviews 48 (2001), pp. 3-26.*
Bundgaard, Design of Prodrugs, p. 1, 1985.*
Silverman, Prodrugs and Drug Delivery Systems, The Organic Chemistry of Drug Design and Drug Action, pp. 352-399, 1992.*
Banker et al., Prodrugs, Modern Pharmaceutics, Third Edition, Revised and Expanded, pp. 451 and 596 (1996).*
Wolff, Some consideration for prodrug design, Burger's Medicinal Chemistry and Drug Discovery, 5th Edition, vol. 1: Principles and Practice, pp. 975-977, 1995.*
Worsch et al., Separation of Enantiomers by Clathrate Formation, Topics in Current Chemistry, vol. 140, pp. 23-41, 1987.*
Samsonov et al., Synthesis of 1-hydroxybenzotriazoles angularly annulated by furazan orfuroxan rings, Russian Chemical Bulletin, International Edition, vol. 58, No. 11, pp. 2369-2375 (Nov. 2009).*
PubChem CID 650038 (2005).*
PubChem CID 3244385 (2005).*
PubChem CID 45105911 (2010).*
STN Registry RN 332849-94-2 (2001).*
"International Application Serial No. PCT/US2019/013201, International Search Report dated Apr. 15, 2019", 2 pgs.
"International Application Serial No. PCT/US2019/013201, Written Opinion dated Apr. 15, 2019", 5 pgs.
Ascenzi, Paolo, et al., "Inactivation of parasite cysteine proteinases by the NO-donor 4-(phenylsulfonyl)-3-((2-(dimethylamino)ethyl)thio)-furoxan oxalate", Biochimica et Biophysica Acta., vol. 1703, (2004), 69-77.
Samsonov, VA, et al., "Interaction of 4-Aminobenzofurazan with Aryldiazonium Salts", Chemistry of Heterocyclic Compounds, 30(10), (1994), 1243-1249.
Schiefer, Isaac T, et al., "Furoxans (1,2, 5 Oxadiazole-N-Oxides) as Novel NO Mimetic Neuroprotective and Procognitive Agents", J Med Chem., 55(7), pp. 3076-3087, (2012), 29 pgs.
Wang, Hongbo, et al., "A Small-molecule Inhibitor of MDMX Activates p53 and Induces Apoptosis", Mol. Cancer Ther.,10(1), (2011), 69-79.
"International Application Serial No. PCT/US2019/013201, International Preliminary Report on Patentability dated Jul. 23, 2020", 7 pgs.
Dagbay, Kevin Buadlart, "Probing the Domain Architecture and Structural Dynamics of Caspase-6 for Its Specific Regulation", PhD diss. University of Massachusetts Amherst, (May 2017), 290 pgs.
MacPherson, Derek Joseph, "Probing Apoptotic Caspase Allostery and Exosite Interactions for Alternative Regulation", PhD diss. University of Massachusetts Amherst, (Oct. 2018), 296 pgs.

* cited by examiner

*Primary Examiner* — Deepak R Rao
(74) *Attorney, Agent, or Firm* — Schwegman Lundberg & Woessner, P.A.

(57) ABSTRACT

Described herein are compounds of the formula (I), as well as pharmaceutical compositions comprising such compounds, and methods for using such compounds/pharmaceutical compositions for treating neurodegenerative diseases including Alzheimer's disease, Parkinson's disease, Huntington's disease, and multiple sclerosis (MS).

7 Claims, No Drawings

FUROXAN-BASED COMPOUNDS AND USES THEREOF

CROSS-REFERENCE TO RELATED APPLICATIONS

This application is a U.S. National Stage Filing under 35 U.S.C. § 371 from International Application No. PCT/US2019/013201, filed on Jan. 11, 2019, which claims the benefit of U.S. Provisional Patent Appl. Ser. No. 62/616,160, filed Jan. 11, 2018, which applications are incorporated by reference in their entireties.

BACKGROUND OF THE INVENTION

Caspases comprise a family of cysteine protease enzymes with a well-known role as key mediators in apoptosis signaling pathways and cell disassembly. Interleukin converting enzyme (ICE), also known as Caspase-1, was the first identified caspase. In humans, 11 other known caspases have been further identified. Caspases have been classified in two general groups according to their effects: proapoptotic (caspase-2, 3, 6, 7, 8, 9, 10) and proinflammatory (caspase-1, 4, 5, 11, 12) caspases. The proapoptotic caspases have been divided in initiators (caspase-2, 8, 9, 10) also known as group II, and executioners (caspase-3, 6, 7) of the apoptotic process or group III. The Interleukin converting enzyme (ICE), also known as Caspase-1, appears to have a proinflammatory role only.

There is growing evidence demonstrating the role of caspases in very diverse pathologies. For instance, increased levels of apoptosis and caspase activity are reported to be frequently observed at sites of cellular damage in both acute (e.g., Sepsis, myocardial infarction (MI), Ischemic Stroke, Spinal cord injury (SCI), traumatic Brain Injury (TBI)) and neurodegenerative disease (e.g. Alzheimer's, Parkinson's and Huntington's diseases, and multiple sclerosis (MS)). And because of the significant impact of such diverse pathologies on the world's population, and the apparent paucity of therapeutic agents that treat those pathologies by targeting (e.g., inhibiting) caspases (e.g., caspase-6), there is a need for compounds designed for inhibiting caspases. Capsase-6 plays a central role in the development and pathology of several neurodegenerative diseases including Alzheimer's and Huntington's diseases, due to cleavage of microtubule associated protein Tau and polygluatimine expanded huntingtin protein.

DETAILED DESCRIPTION OF THE INVENTION

Reference will now be made in detail to certain examples of the disclosed subject matter. While the disclosed subject matter will be described in conjunction with the enumerated claims, it will be understood that the exemplified subject matter is not intended to limit the claims to the disclosed subject matter.

Embodiments of this disclosure are directed to compounds of the general formula (I):

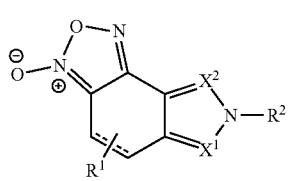

(I)

or a pharmaceutically acceptable salt, polymorph, prodrug, solvate or clathrate thereof,
wherein:
the dashed line represents a single or a double bond;
$R^1$ is H or aryl;
$R^2$ is H or aryl; and
$X^1$ and $X^2$ are each, independently, N, $N^+$—$O^-$ or $CR^3$, wherein $R^3$ is H or alkyl and only one of $X^1$ and $X^2$ can be $N^+$—$O^-$.

Embodiments of this disclosure are also directed to compounds of the general formula (Ia) and (Ib):

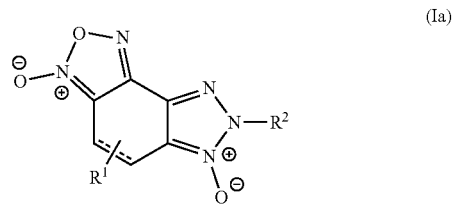

(Ia)

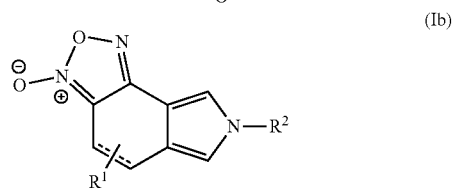

(Ib)

or a pharmaceutically acceptable salt, polymorph, prodrug, solvate or clathrate thereof, wherein the dashed line in the compounds of the formula (Ia) and (Ib) represents a single or a double bond and $R^1$ and $R^2$ are defined herein.

For example, the compound of the formula (I) can be a compound of the formula (Ic):

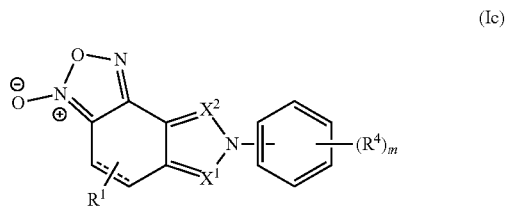

(Ic)

or a pharmaceutically acceptable salt, polymorph, prodrug, solvate or clathrate thereof, wherein the dashed line represents a single or a double bond; $X^1$, $X^2$, and $R^1$ are defined herein; m is an integer from 1 to 3; and each $R^4$ is, independently, H, halo, alkyl, alkoxy, nitro, $N(R^5)_2$, $COR^6$, or haloalkyl, wherein each $R^5$ is, independently, H, $S(O)_nR^7$ or acyl, wherein $R^7$ can be alkyl or aryl and n is an integer from 1 to 2, and $R^6$ is H, alkyl, alkenyl, alkynyl, aryl, heteroaryl or $N(R^8)_2$, wherein each $R^6$ is, independently, H, alkyl or aryl; or, two adjacent $R^4$ groups, together with the atoms to which they are attached, can form an aryl or a heteroaryl group.

In the compounds of the formula (I), (Ia), and (Ic), $R^4$ can be fluoro, iodo or bromo, when m is 1. When m is 1, $R^4$ can be chloro, fluoro, iodo or bromo, provided that when $R^4$ is chloro, the chloro group forms a 2-chloro, 3-chloro or 4-chloro phenyl group. And when m is 2, $R^4$ can be chloro, fluoro, iodo or bromo, provided that when the two $R^4$ groups are chloro, the two chloro groups form a 1,2-dichloro, 1,4-dichloro, 1,5-dichloro, 2,4-dichloro or 2,5-dichloro phenyl group. In the compounds of the formula (I), (Ia), and (Ic), R⁴ can be $C_2$-$C_{20}$ alkyl, e.g., when m is 1. When m is 1, R⁴ can be alkyl, provided that when R⁴ is methyl, the methyl group forms a 1-methyl or 2-methyl phenyl group.

Excluded from the scope of the compounds of the formula (I), (Ia), and (Ic) are the compounds of the formulae:

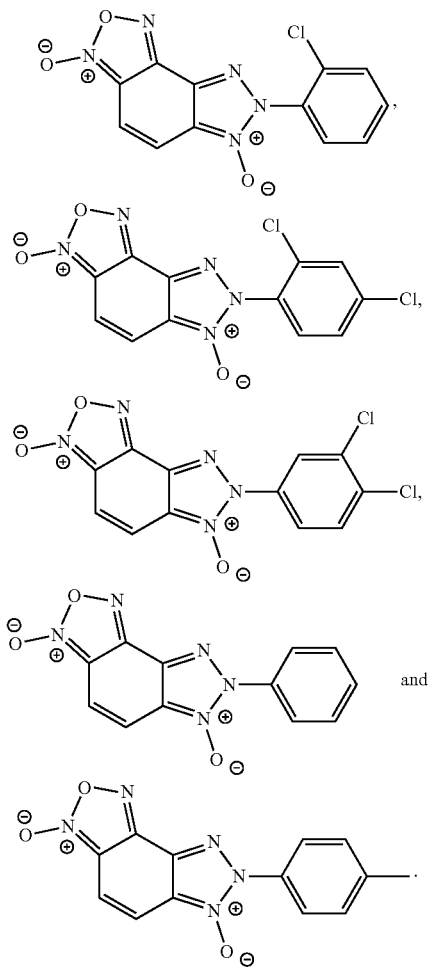

and

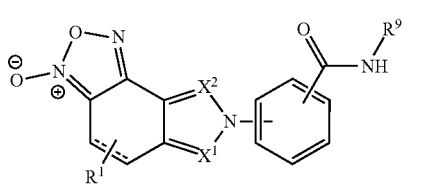

For example, the compound of the formula (I) can be a compound of the formula (Id):

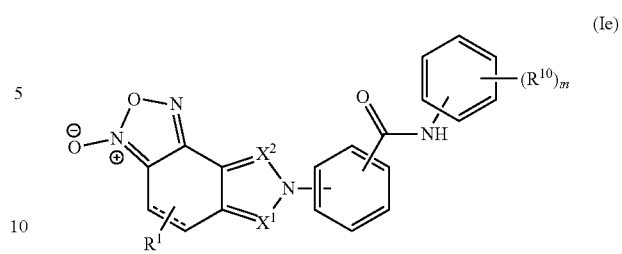

(Id)

or a pharmaceutically acceptable salt, polymorph, prodrug, solvate or clathrate thereof, wherein the dashed line represents a single or a double bond; $X^1$, $X^2$, and $R^1$ are defined herein; m is an integer from 1 to 3; and $R^9$ is H, alkyl, aryl, alkenyl, alkynyl, arylalkyl or heteroarylalkyl.

The dashed line in the compounds of the formula (I) and (Ia)-(If) can be a single bond.

For example, the compound of the formula (I) can be a compound of the formula (Ie):

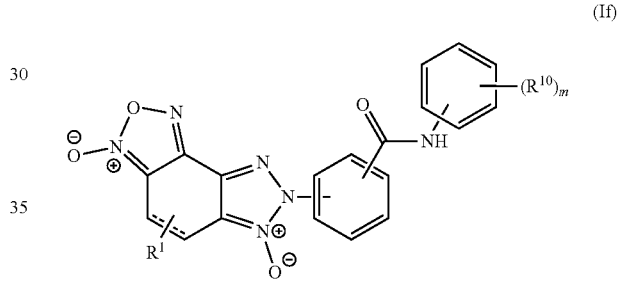

(Ie)

or a pharmaceutically acceptable salt, polymorph, prodrug, solvate or clathrate thereof, wherein the dashed line represents a single or a double bond; $X^1$, $X^2$, and $R^1$ are defined herein; m is an integer from 1 to 3; and $R^{10}$ is H, halo, alkyl, OH, alkoxy, aryl, alkenyl, alkynyl, arylalkyl, heteroarylalkyl, heterocyclyl, $N(R^5)_2$ or $COR^6$, wherein $R^5$ and $R^6$ are defined herein; or, two adjacent $R^{10}$ groups, together with the atoms to which they are attached, can form a cycloalkyl, aryl or a heteroaryl group.

For example, the compound of the formula (I) can be a compound of the formula (If):

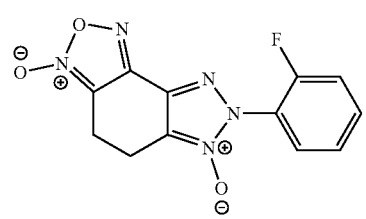

(If)

or a pharmaceutically acceptable salt, polymorph, prodrug, solvate or clathrate thereof, wherein the dashed line represents a single or a double bond: $R^1$, $R^{10}$, and m are defined herein.

Compounds contemplated herein include compounds of the formula:

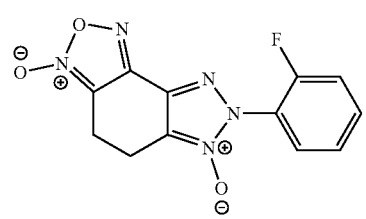

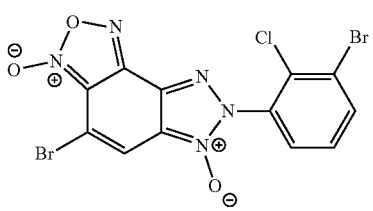

5
-continued
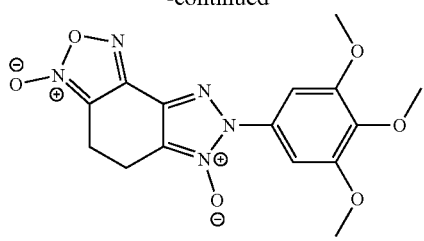
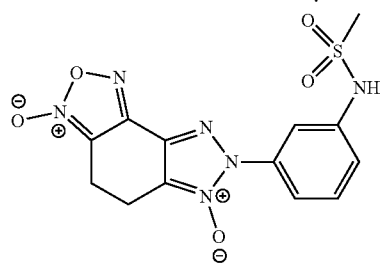
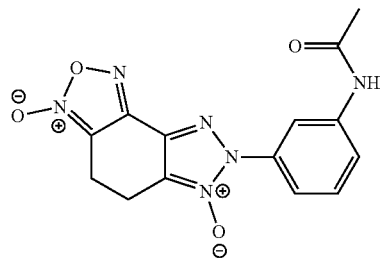
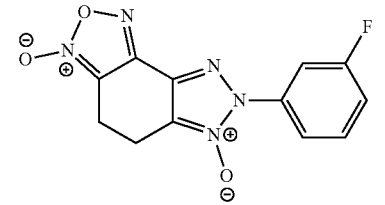
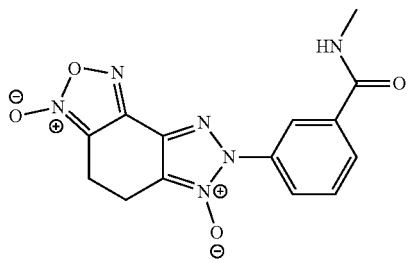
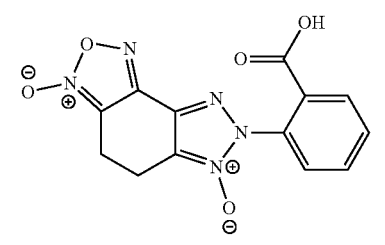
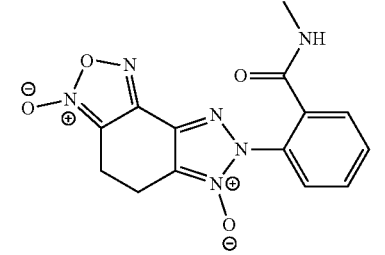
6
-continued
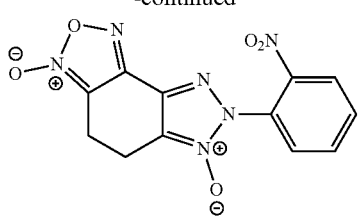
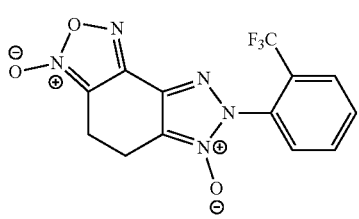
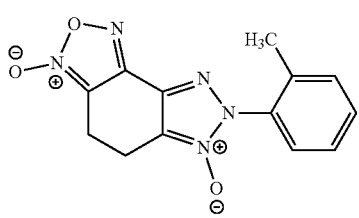
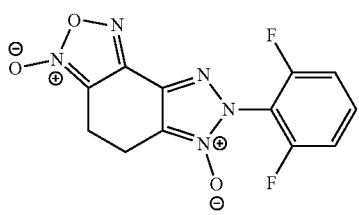
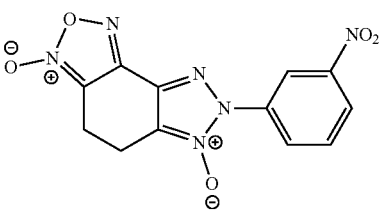
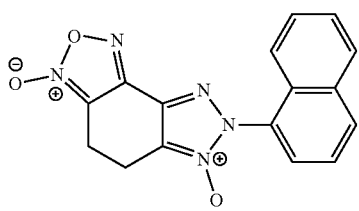
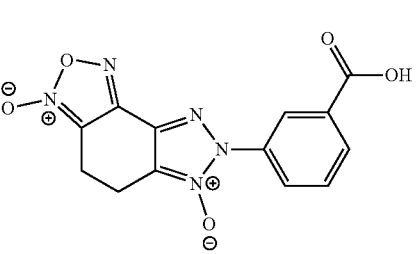

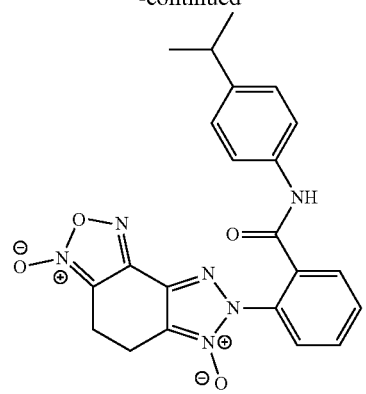
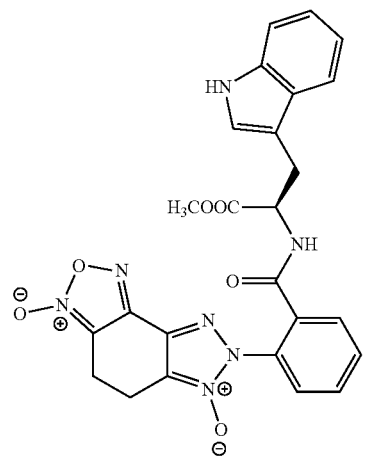
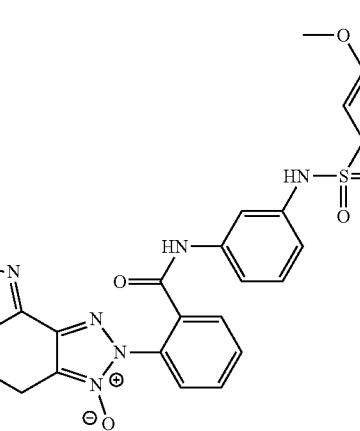
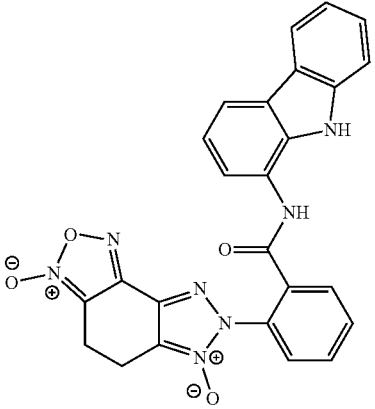
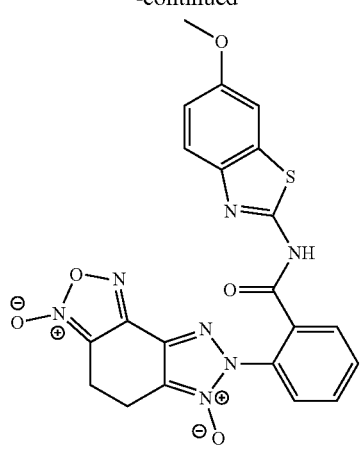
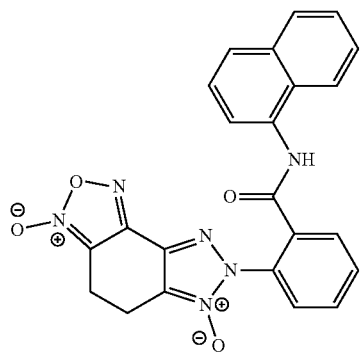
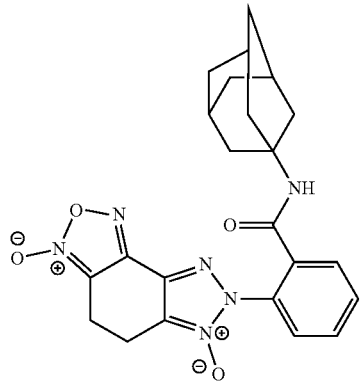
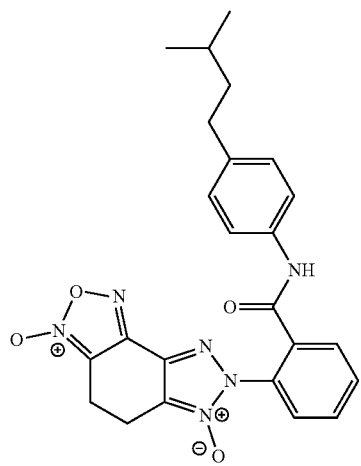

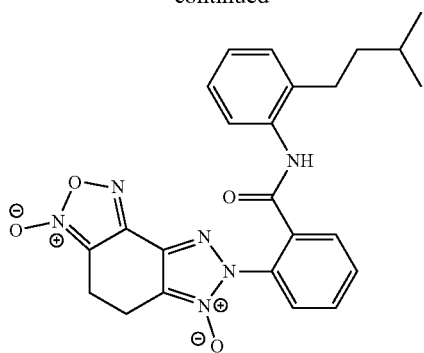
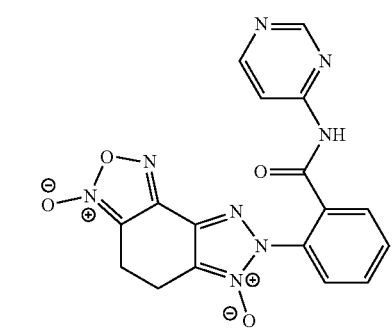
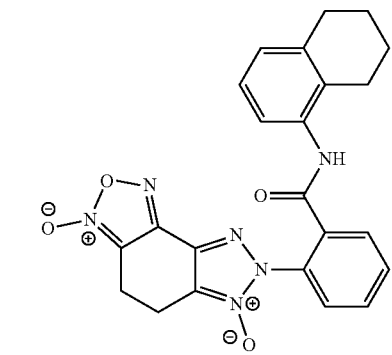
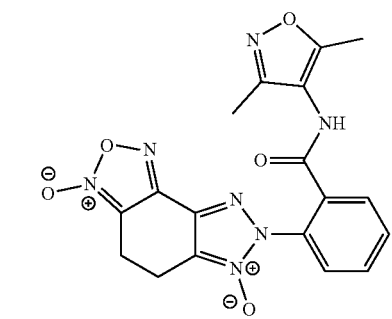
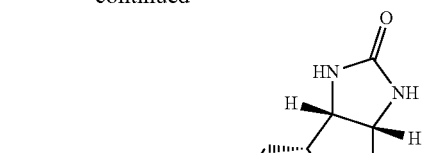
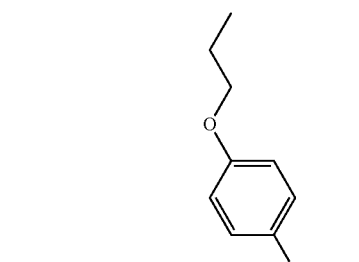
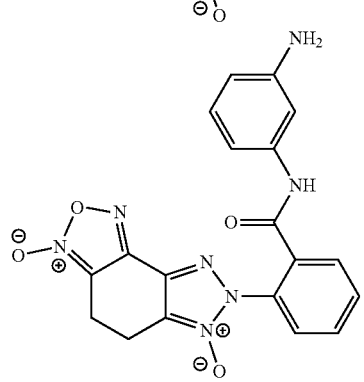
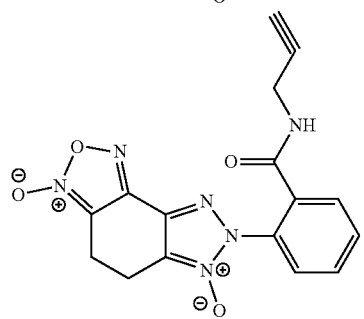

11
-continued
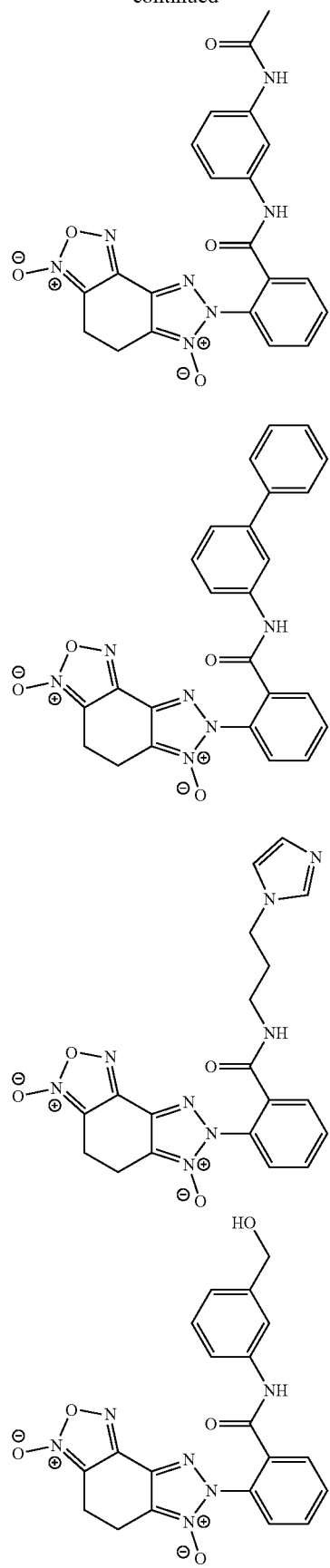
12
-continued
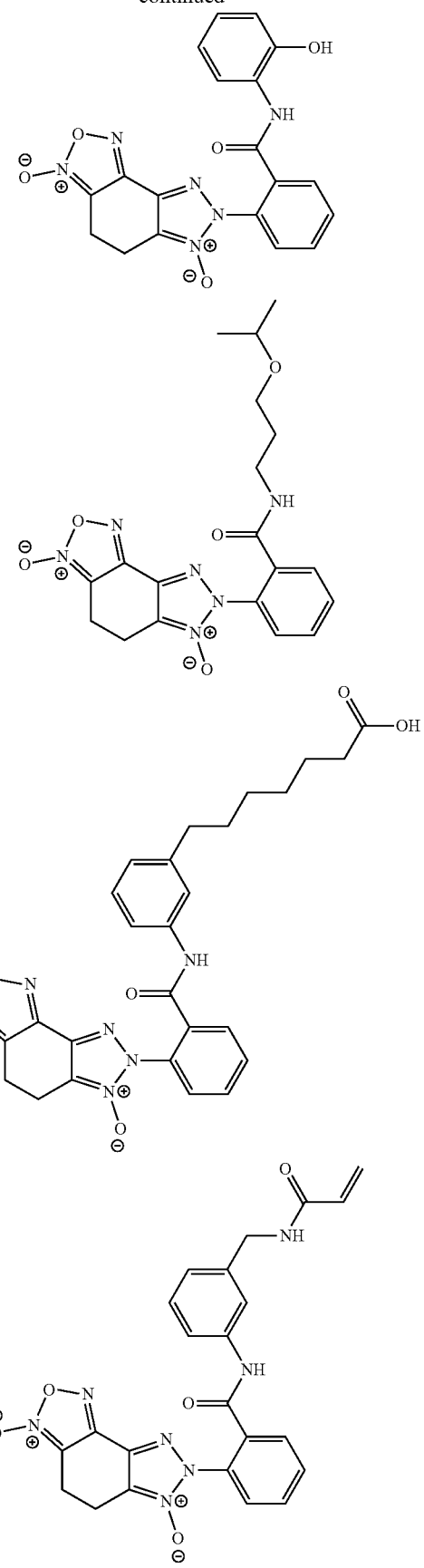

-continued
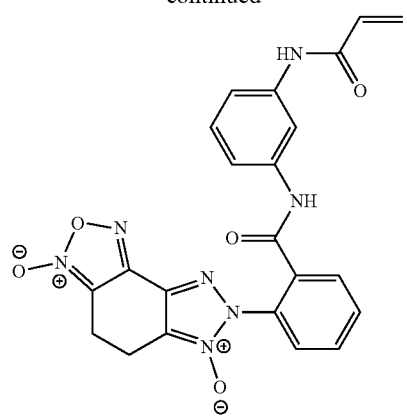
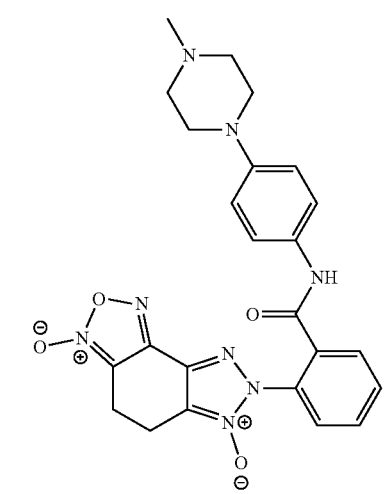
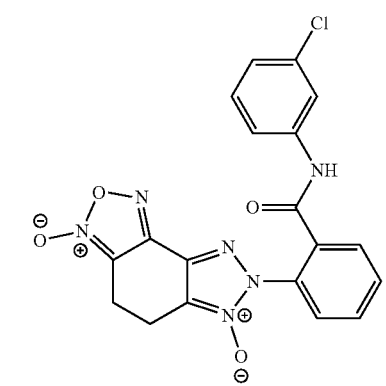
-continued
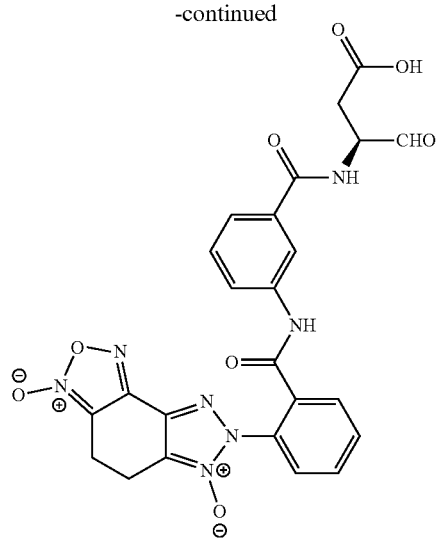
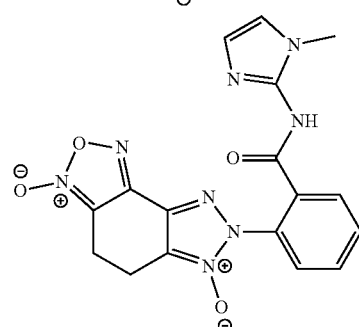
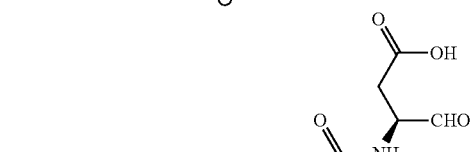
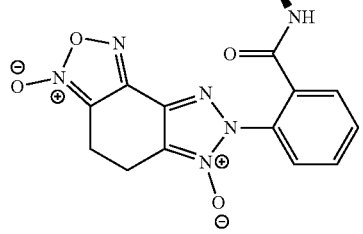

15
-continued
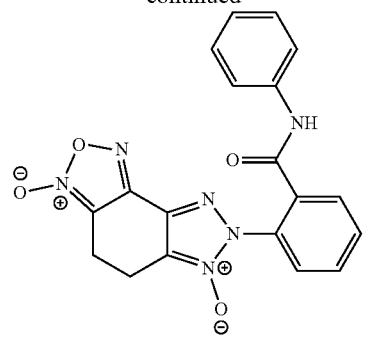
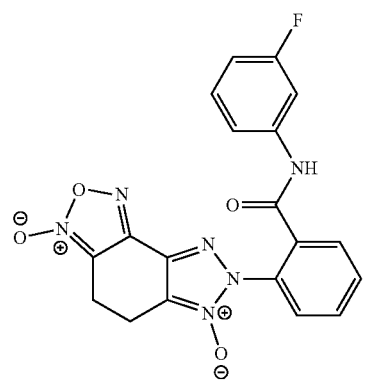
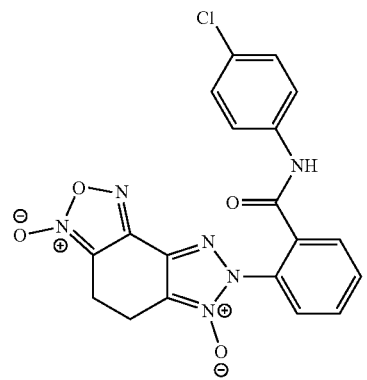
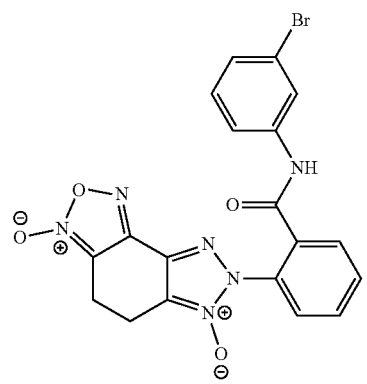
16
-continued
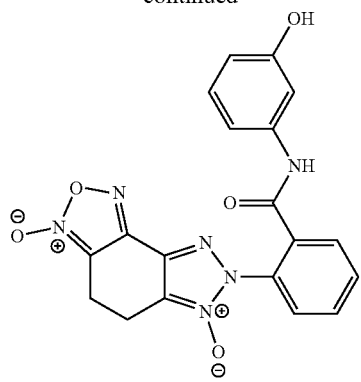
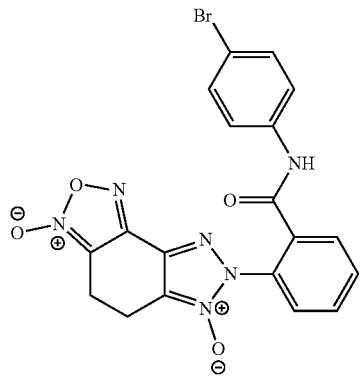
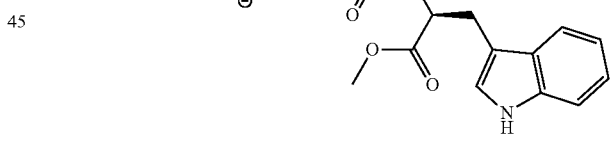
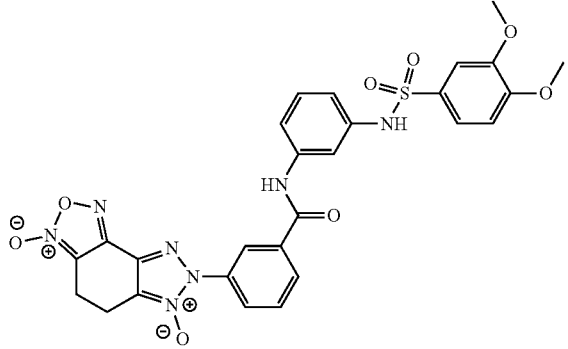

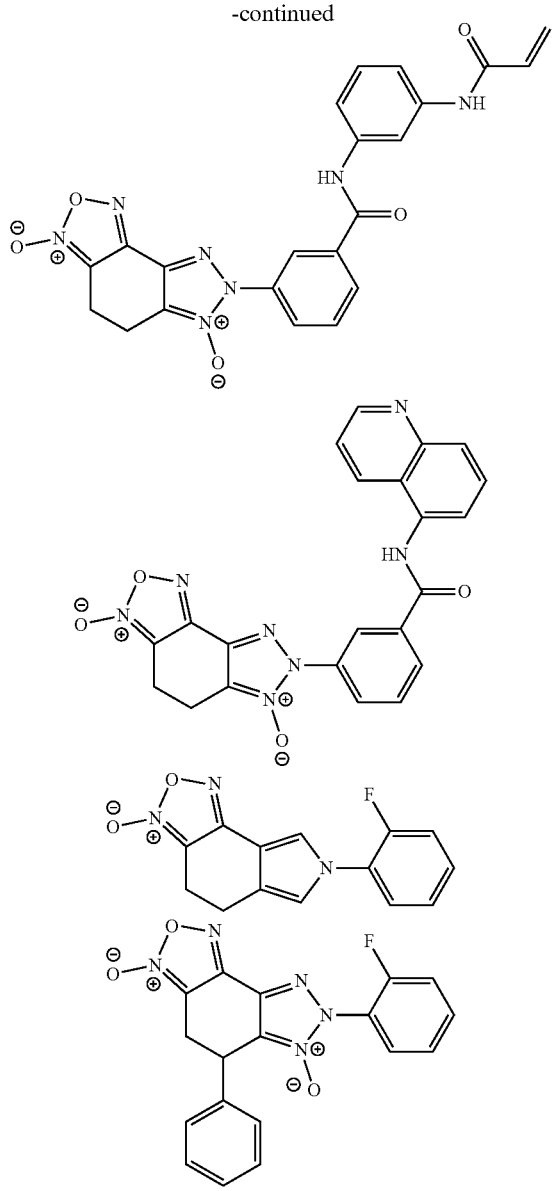

or a pharmaceutically acceptable salt, polymorph, prodrug, solvate or clathrate thereof.

Those of ordinary skill in the art will recognize that the compounds described herein can contain chiral centers. All diastereomers of the compounds described herein are contemplated herein, as well as racemates. Prodrugs of the compounds described are also contemplated herein.

The compounds described herein (e.g., compounds of the formula (I) and (Ia)-(If)) can be formulated into pharmaceutical compositions comprising one or more compounds of the various embodiments described herein and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In some cases isotonic agents can be included in the pharmaceutical compositions, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the various embodiments described herein or an appropriate pharmaceutical composition thereof are effective, the compounds of the various embodiments described herein may be administered in an effective amount. The dosages as suitable for this invention may be a composition, a pharmaceutical composition or any other compositions described herein.

The dosage can be administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

Pharmaceutical compositions comprising a therapeutically effective amount of at least one compound described herein (e.g, compounds of the formula (I) and (Ia)-(If)) are contemplated by the disclosure. The compositions can be useful in a method for treating a neurodegenerative disease (e.g. Alzheimer's, Parkinson's and Huntington's diseases, and multiple sclerosis (MS)), the method comprising administering a therapeutically effective amount of at least one compound described herein to a patient in need thereof. The compounds described herein can also be used as a medicament for treating a patient in need of relief from a neurodegenerative disease.

The compositions contemplated herein can also be generally useful in a method for inhibiting caspase-6 with a compound that reacts with the sulfhydryl group (SH) on cysteine 264 of caspase-6, the method comprising contacting caspase-6 (e.g., in vitro or in vivo) with an effective amount of said compound. While not wishing to be bound to any specific theory, it is believed that the compounds described herein (e.g, compounds of the formula (I) and (Ia)-(If)) are compounds that can react with the sulfhydryl group (SH) on cysteine 264 of caspase-6. The mechanism of this reaction could be the mechanism shown in Scheme A.

disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher,

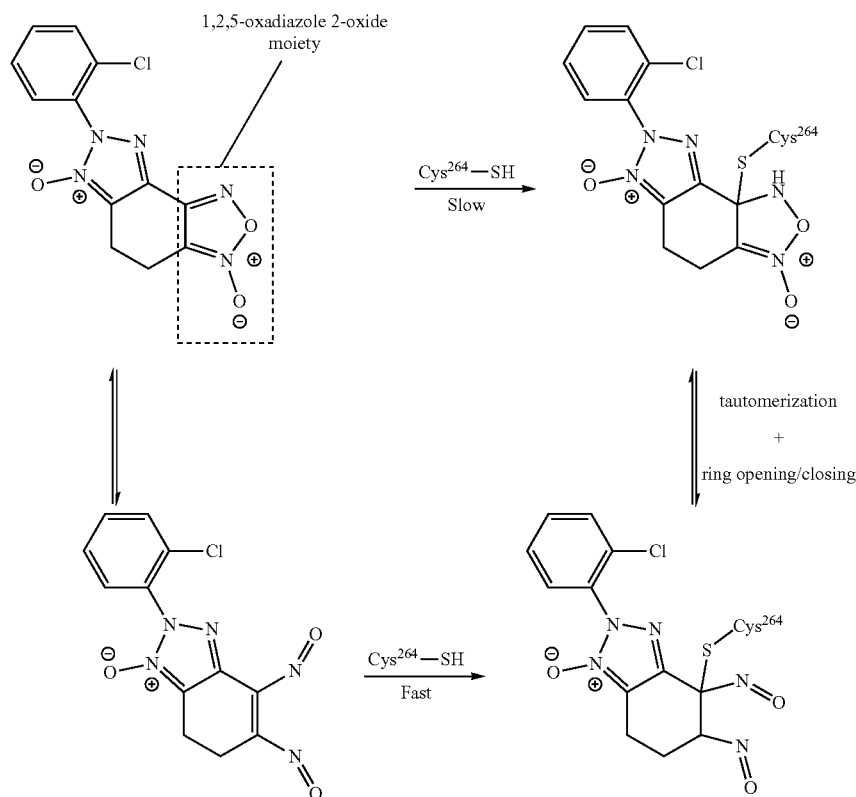

The method can therefore be a method for inhibiting caspase-6 with a compound comprising at least one 1,2,5-oxadiazole-2-oxide moiety that reacts with the sulfhydryl group (SH) on cysteine 264 of caspase-6, the method comprising contacting caspase-6 (e.g., in vitro or in vivo) with an effective amount of said compound.

The term "therapeutically effective amount" as used herein, refers to that amount of one or more compounds of the various embodiments described herein (e.g, compounds of the formula (I) and (Ia)-(If)) that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the veterinarian, medical doctor or other clinician. It is also appreciated that the therapeutically effective amount can be selected with reference to any toxicity, or other undesirable side effect, that might occur during administration of one or more of the compounds described herein.

The compounds of the various embodiments described herein can have a half-maximal inhibitory concentration ($IC_{50}$) for caspase-6 of from about 1 nM to about 100 µM (e.g., about 10 nM to about 200 nM, about 100 nM to about 900 nM, about 20 nM to about 500 nM, about 100 nM to about 600 nM, from about 500 nM to about 100 µM, about 800 nM to about 50 µM, about µM to about 90 µM, about 900 nM to about 30 µM or about 1 µM to about 50 µM).

The compounds of the various embodiments described herein can have an $IC_{50}$ for caspase-6 that is about four to about 100 times lower than the $IC_{50}$ for caspase-3 or caspase-7, or -8 or -9. The IC$_{50}$ for caspase-6 can be at least about 20 to about 100 times lower than the IC$_{50}$ for caspase-3 or caspase-7-9 (e.g., the IC$_{50}$ for caspase-3 or caspase-7 or -8 or -9 is about 20 to about 100 times greater than the IC$_{50}$ for caspase-6).

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.10% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "substituted" or "substituent" as used herein refers to a group that can be or is substituted onto a molecule or onto another group (e.g., on an aryl or an alkyl group). Examples of substituents include, but are not limited to, a halogen (e.g., F, Cl, Br, and I), OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, —(CH$_2$)$_{0-2}$P(O)(OR)$_2$, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-10}$N(R)C(O)R, (CH$_2$)$_{0-10}$N(R)C(O)OR, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, or C(=NOR)R wherein each R can be, independently, hydrogen, alkyl, acyl, cycloalkyl, aryl, aralkyl, heterocyclyl, heteroaryl, or heteroarylalkyl, wherein any alkyl, acyl, cycloalkyl, aryl, aralkyl, heterocyclyl, heteroaryl, or heteroarylalkyl or two R groups bonded to a nitrogen atom or to adjacent nitrogen atoms can together with the nitrogen atom or atoms form a heterocyclyl, which can be mono- or independently multi-substituted.

The term "alkyl" as used herein refers to substituted or unsubstituted straight chain and branched alkyl groups and cycloalkyl groups having from 1 to 40 carbon atoms (C$_1$-C$_{40}$), 1 to about 20 carbon atoms (C$_1$-C$_{20}$), 2 to about 20 carbon atoms (C$_1$-C$_{20}$), 1 to 12 carbons (C$_1$-C$_{12}$), 1 to 8 carbon atoms (C$_1$-C$_8$), or, in some embodiments, from 1 to 6 carbon atoms (C$_1$-C$_6$) or 2 to 6 carbon atoms (C$_2$-C$_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl," as used herein, refers to substituted or unsubstituted straight and branched chain and cyclic alkyl (cycloalkyl) groups as defined herein, except that at least one double bond exists between two adjacent carbon atoms. Thus, alkenyl groups have from 2 to 40 carbon atoms, or 2 to about 20 carbon atoms, or 2 to 12 carbons or, in some embodiments, from 2 to 8 carbon atoms. Examples of alkenyl groups include, but are not limited to, vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl," as used herein, refers to substituted or unsubstituted straight and branched chain alkyl groups, except that at least one triple bond exists between two adjacent carbon atoms. Thus, alkynyl groups have from 2 to 40 carbon atoms, 2 to about carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms (C$_3$-C$_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "cycloalkylalkyl" as used herein refers to substituted or unsubstituted alkyl groups as defined herein in which a hydrogen or carbon bond of an alkyl group as defined herein is replaced with a bond to a cycloalkyl group as defined herein. Representative cycloalkylalkyl groups include, but are not limited to, cyclopentylalkyl.

The term "alkylcycloalkyl" as used herein refers to substituted or unsubstituted cycloalkyl groups as defined herein in which a hydrogen of a cycloalkyl group as defined herein is replaced with a bond to an alkyl group as defined herein. Representative alkylcycloalkyl groups include, but are not limited to, alkylcyclopropyl.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "heterocyclylcarbonyl" is an example of an acyl group that is bonded to a substituted or unsubstituted heterocyclyl group, as the term "heterocyclyl" is defined herein. An example of a heterocyclylcarbonyl group is a prolyl group, wherein the prolyl group can be a D- or an L-prolyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be monosubstituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein. The aralkyl group can, in turn, be unsubstituted or substituted, either at the aryl portion, the alkyl portion or both the aryl and alkyl portions of the group.

The term "heterocyclyl" or "heterocyclo" as used herein refers to substituted or unsubstituted aromatic and non-aromatic ring compounds containing 3 or more ring members, of which, one or more (e.g., 1, 2 or 3) is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$), 3 to 5 carbon atoms ($C_3$-$C_5$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl. The heterocyclylalkyl group can, in turn, be unsubstituted or substituted, either at the heterocyclyl portion, the alkyl portion or both the heterocyclyl and alkyl portions of the group. An example of a heterocyclylalkyl group that is substituted at the alkyl portion (by the group C(O)OR) of the group is:

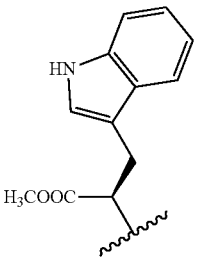

The term "heterocyclylalkoxy" as used herein refers to alkyl groups as defined herein in which a hydrogen or carbon bond of an alkyl group as defined herein is replaced with a bond to a heterocyclyl group as defined herein and the alkyl group is attached to an oxygen. Representative heterocyclylalkoxy groups include, but are not limited to, —O—$(CH_2)_q$heterocyclyl, wherein q is an integer from 1 to 5. In some embodiments, heterocyclylalkoxy groups include —O—$(CH_2)_q$morpholinyl such as —O—$CH_2CH_2$-morpholine.

The term "heteroarylalkyl" as used herein refers to alkyl groups as defined herein in which a hydrogen or carbon bond of an alkyl group is replaced with a bond to a heteroaryl group as defined herein. The heteroarylalkyl group can, in turn, be unsubstituted or substituted, either at the heteroaryl portion, the alkyl portion or both the heteroaryl and alkyl portions of the group.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein R is defined herein, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —NH$_2$, —NHR, —NR$_2$, —NR$_3^+$, wherein each R is defined herein, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

An example of a "alkylamino" is —NH-alkyl and —N(alkyl)$_2$.

An example of a "cycloalkylamino" group is —NH-cycloalkyl and —N(cycloalkyl)$_2$.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —CF(CH$_3$)$_2$ and the like.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Examples

The present invention can be better understood by reference to the following examples which are offered by way of illustration. The present invention is not limited to the examples given herein.

Materials and Methods:

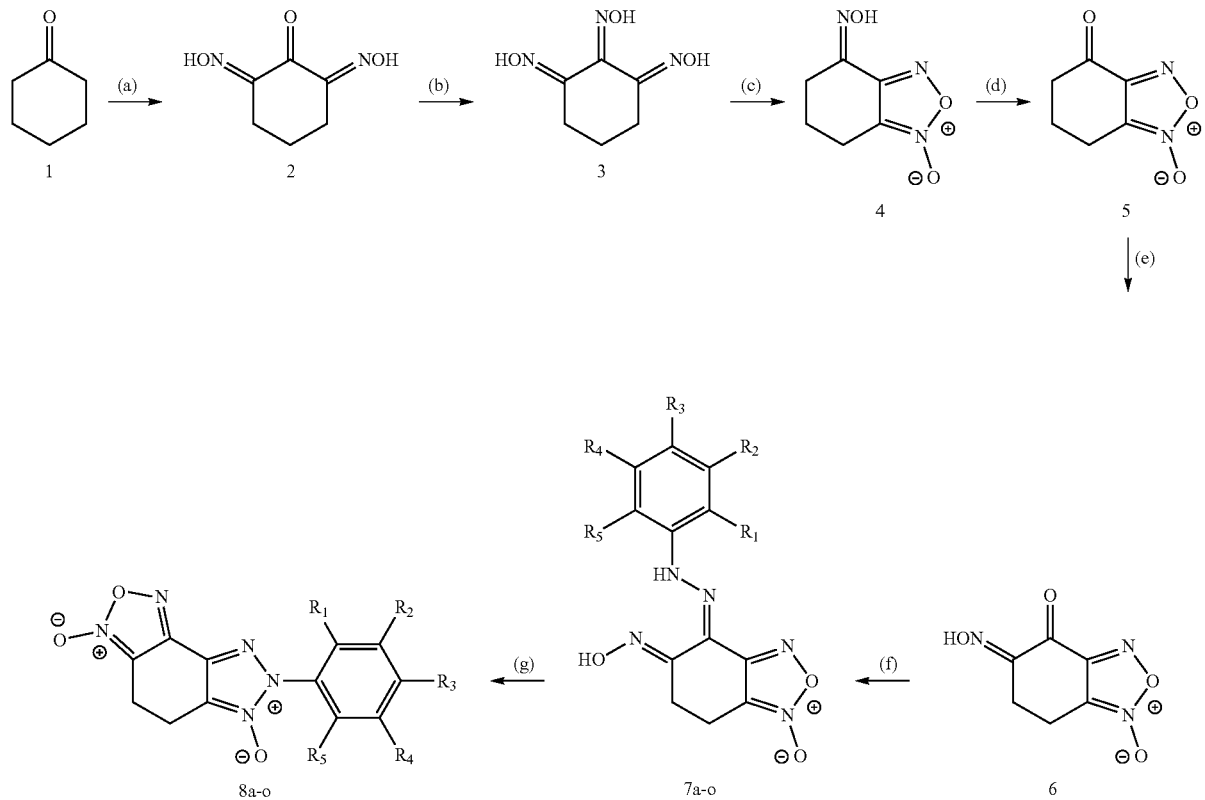

Scheme-1. Synthesis of Compound-A Analogs (8a-o).

7a $R_1$ = H: $R_2$ = OCH$_3$: $R_3$ = OCH$_3$: $R_4$ = OCH$_3$; $R_5$ = H.
7b $R_1$ = H; $R_2$ = N-methane sulfonamide; $R_3$ = H: $R_4$ = H; $R_5$ = H.
7c R1 = H; $R_2$ = N-acetamide; $R_3$ = H: $R_4$ = H; $R_5$ = H.
7d R1 = H; $R_2$ = F: $R_3$ = H: $R_4$ = H; $R_5$ = H.
7e R1 = H; $R_2$ = N-methyamide; $R_3$ = H: $R_4$ = H; $R_5$ = H.
7f $R_1$ = F: $R_2$ = H: $R_3$ = H: $R_4$ = H; $R_5$ = H.
7g $R_1$ = COOH: $R_2$ = H: $R_3$ = H: $R_4$ = H; $R_5$ = H.
7h $R_1$ = N-methylamide; $R_2$ = H; $R_3$ = H: $R_4$ = H; $R_5$ = H.

7i R1 = NO$_2$; $R_2$ = H; $R_3$ = H: $R_4$ = H; $R_5$ = H.
7j $R_1$ = CF$_3$: $R_2$ = H; $R_3$ = H: $R_4$ = H; $R_5$ = H.
7k R1 = CH$_3$; $R_2$ = H; $R_3$ = H: $R_4$ = H; $R_5$ = H.
7l $R_1$ = F: $R_2$ = H: $R_3$ = H: $R_4$ = H; $R_5$ = F.
7m $R_1$ = H: $R_2$ = NO$_2$: $R_3$ = H: $R_4$ = H; $R_5$ = H.
7n R1 $R_2$ = Phenyl; $R_3$ = H: $R_4$ = H; $R_5$ = H.
7o $R_1$ = H: $R_2$ = COOH: $R_3$ = H: $R_4$ = H; $R_5$ = H.

8a $R_1$ = H: $R_2$ = OCH$_3$: $R_3$ = OCH$_3$: $R_4$ = OCH$_3$; $R_5$ = H.
8b $R_1$ = H; $R_2$ = N-methane sulfonamide; $R_3$ = H: $R_4$ = H; $R_5$ = H.
8c R1 = H; $R_2$ = N-acetamide; $R_3$ = H: $R_4$ = H; $R_5$ = H.
8d R1 = H; $R_2$ = F: $R_3$ = H: $R_4$ = H; $R_5$ = H.
8e R1 = H; $R_2$ = N-methyamide; $R_3$ = H: $R_4$ = H; $R_5$ = H.
8f $R_1$ = F: $R_2$ = H: $R_3$ = H: $R_4$ = H; $R_5$ = H.
8g $R_1$ = COOH: $R_2$ = H: $R_3$ = H: $R_4$ = H; $R_5$ = H.
8h $R_1$ = N-methylamide; $R_2$ = H; $R_3$ = H: $R_4$ = H; $R_5$ = H.

8i R1 = NO$_2$; $R_2$ = H; $R_3$ = H: $R_4$ = H; $R_5$ = H.
8j $R_1$ = CF$_3$: $R_2$ = H; $R_3$ = H: $R_4$ = H; $R_5$ = H.
8k R1 = CH$_3$; $R_2$ = H; $R_3$ = H: $R_4$ = H; $R_5$ = H.
8l $R_1$ = F: $R_2$ = H: $R_3$ = H: $R_4$ = H; $R_5$ = F.
8m $R_1$ = H: $R_2$ = NO$_2$: $R_3$ = H: $R_4$ = H; $R_5$ = H.
8n R1 $R_2$ = Phenyl; $R_3$ = H: $R_4$ = H; $R_5$ = H.
8o $R_1$ = H: $R_2$ = COOH: $R_3$ = H: $R_4$ = H; $R_5$ = H.

Reagents and conditions: (a) Diethyl ether, methyl nitrite, 0°-25° C., 4 h (90%); (b) Na$_2$CO$_3$, NH$_2$OH.HCl, EtOH:H$_2$O (1:1), 6 h (85%); (c) NaOBr aq Sol, H$_2$O, 30 min (85%); (d) HCHO, Con. HCl, 25° C., 20 min (90%); (e) NaNO$_2$, EtOH, AcOH, 25° C., 12 h (90%); (f) Corresponding Hydrazines, EtOH, Cat. AcOH, 25° C., 20-40 min (90%); (g) activated MnO$_2$, Acetonitrile, 85° C., 20-40 min (90%).

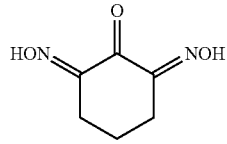

Preparation of 2,6-Dioximinocyclohexanone (2): To a solution of 50 g. (0.509 moles) of cyclohexanone on 200 ml. of ether was added 11 ml. of con. HCl. The reaction mixture was cooled to 10° C., and nitrogen gas was passed slowly through it for 15-20 min. Then methyl nitrite was passed slowly from an external generator. The methyl nitrite gas was generated by adding a solution of 32 ml. of con. H$_2$SO$_4$ in 58 ml. of H$_2$O dropwise to a mixture of 86 g. of sodium nitrite, 41 g. of methanol, and 76 ml. of H$_2$O. The temperature was maintained at 5-10° C., while the methyl nitrite was passed in over about 2 h until the methyl nitrite gas was seized. A pale Yellow solid was precipitated as the reaction proceeded. Then the reaction mixture was stirred at 25° C. for about 2 h, the solid was filtered on Buckner funnel and washed with (100 ml×2) diethyl ether and dried thoroughly to obtain pure product 2 as a pale yellow solid (70.8 g, 89% yield). $^1$H NMR (400 MHz, DMSO-d$_6$): δ (ppm): 2.69-2.65 (t, J=6.5 Hz, 4H), 1.76-1.69 (m, 2H); $^{13}$C NMR (100 MHz, DMSO-d$_6$): δ (ppm): 181.6, 154.6, 24.3, 17.9; MS (EI, m/z): 156 [M]$^+$.

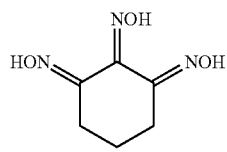

Preparation of 1, 2, 3-Cyclohexane trioxime (3): To a solution of compound-2, 31.3 g. (0.2 moles) in 300 ml. of 50% aq Ethanol was added 12.9 g. of Na$_2$CO$_3$, followed by 17.4 g of Hydroxylamine hydrochloride at stirring. The stirring was continued at 25° C. for about overnight. The precipitate obtained was filtered on Buckner funnel and washed with (50 ml×2) of H$_2$O. The solid was dried thoroughly to obtain compound-3 as a pale brown solid (27 g, 80% yield). $^1$H NMR (400 MHz, DMSO-d$_6$): δ (ppm): 12.59 (s, 1H), 11.83 (s, 1H), 11.33 (s, 1H), 2.58-2.49 (m, 4H), 1.65-1.56 (m, 2H); $^{13}$C NMR (100 MHz, DMSO-d$_6$): δ (ppm): 154.6, 153.1, 144.2, 25.2, 24.9, 18.1; MS (EI, m/z): 171 [M]$^+$.

Preparation of 4-Hydroxyimino-4,5,6,7-tetrahydrobenzo [c][1,2,5]oxadiazole 1-oxide (4): To a solution of 10 g. (0.058 moles) of trioxime 3 in 35 ml. of 10% NaOH was added at reaction temperature 5-10° C. a solution of sodium hypobromite prepared from 4.67 g. of NaOH in 44 ml. of water and 1.5 ml. of bromine. The reaction mixture was stirred 1 h at 25° C. and 8 ml. of con HCl was added drop wise over a period of 10 min. The precipitate obtained was filtered on Buckner funnel and washed with (20 ml.×2) H$_2$O and dried to obtain compound-4 as a pale yellow solid (8.1 g. 82% yield). $^1$H NMR (400 MHz, DMSO-d$_6$): δ (ppm): 12.26 (s, 1H), 2.71-2.61 (m, 4H), 1.89-1.81 (m, 2H); $^{13}$C NMR (100 MHz, DMSO-d$_6$): δ (ppm): 152.0, 145.3, 114.3, 22.6, 19.5, 19.2; MS (EI, m/z): 169 [M]$^+$.

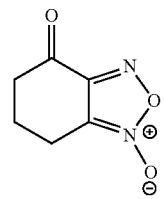 [SMILES: O=C1CCCc2c1no[n+]2[O-]]

Preparation of 4-oxo-4,5,6,7-tetrahydrobenzo[c][1,2,5] oxadiazole 1-oxide (5): To a stirred solution of 8 g (0.04 moles) compound-4 in 70 ml. of 30% formaldehyde was added 53 ml. of con HCl, slowly dropwise over a period of 20 min. Continued the stirring at 25° C. for about 20 min and extracted with chloroform (2×100 ml). The organic layer was separated and washed with water (2×100 ml) and dried over anhydrous Na$_2$SO$_4$ and concentrated on rota vapour under reduced vacuum to give the product 5 as pale yellow solid (6.5 g 90% yield). $^1$H NMR (400 MHz, DMSO-d$_6$): δ (ppm): 2.91-2.85 (t, J=6.25 Hz, 2H), 2.78-2.73 (m, 2H), 2.30-2.21 (m, 2H); $^{13}$C NMR (100 MHz, DMSO-d$_6$): δ (ppm): 183.9, 145.9, 108.7, 35.2, 16.2, 14.5; MS (EI, m/z): 154 [M]$^+$.

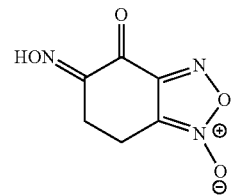

Preparation of 5-(hydroxyimino)-4-oxo-4,5,6,7-tetrahydrobenzo[c][1,2,5]oxadiazole 1-oxide (6): To a stirred solution of 6 g (0.038 moles) compound 5 in 46 ml. of ethanol was added 46 ml. of acetic acid and 2.95 g (0.042 moles) of sodium nitrite at 0° C. The stirring was continues at 0° C. for 4 h and at 25° C. for about overnight. The precipitate was filtered on Buckner funnel and washed with (2×10 ml) water and dried thoroughly to obtain product 6 as pale yellow solid. Evaporation of the filtrate gave a further amount of product. (5 g, 70% yield). $^1$H NMR (400 MHz, DMSO-d$_6$): δ (ppm): 13.12 (s, 1H), 3.08-3.02 (t, J=6.8 Hz, 2H), 2.88-2.83 (t, J=7.0 Hz, 2H); $^{13}$C NMR (100 MHz, DMSO-d$_6$): δ (ppm): 175.2, 153.6, 152.3, 115.1, 20.4, 16.2; MS (EI, m/z): 183 [M]$^+$.

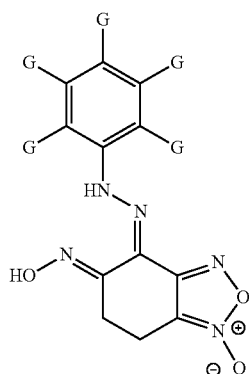

wherein each G is a substituent on the aryl ring.

General procedure for the preparation of (4)-4-(Substituted aromatic hydrazono)-5-(hydroxyimino)-4,5,6,7-tetrahydrobenzo[c][1,2,5]oxadiazole 1-oxides (7a-z): To a stirred solution of 500 mg (2.73 mmoles, 1 equi) of compound 6 in 10 ml. of ethanol was added corresponding hydrazine compounds (2.73 mmoles, 1 equi) and catalytic amount of acetic acid. The stirring was continued at 25° C. for 30 min. The precipitate was filtered on Buckner funnel and washed with (5 mi) of ethanol and dried thoroughly to obtain products (7a-z) as solids. (70-85% yield).

General procedure for Preparation of 7-(substituted aromatic)-5,7-dihydro-4H-[1,2,3]triazolo[4',5':3,4]benzo[1,2-c][1,2,5]oxadiazole 3,6-dioxide (8a-o): To a solution of corresponding hydrazones (1 equi) in acetonitrile (100 times), activated MnO$_2$ (7 equi) was added. The reaction mixture was stirred at 85° C. for 2-3 h. (until all the starting compound has disappeared, TLC monitoring). After completion of the reaction the reaction mixture was cooled to 25° C. and filtered on Buckner funnel over celite and washed with acetonitrile (2×50 ml). The filtrate was evaporated on rota vapour at reduced vacuum and the crude product was purified by column chromatography (silica gel 120-200 mesh) using Ethylaceate/n-Hexane as eluents to afford the compounds with high purity (8a-o).

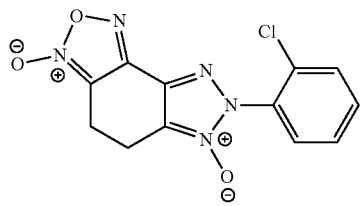 [SMILES: [O-][n+]1onc2c1CCc1c-2nn(-c2ccccc2Cl)[n+]1[O-]]

7-(2-Chlorophenyl)-5,7-dihydro-4H-[1,2,3]triazolo[4',5':3,4]benzo[1,2-c][1,2,5]oxadiazole 3,6-dioxide (CMPD-A): Compound A was prepared according to the method described in general procedure. Employing compound 7A (500 mg, 1.62 mmol) in 50 ml. of acetonitrile and MnO$_2$ (990 mg, 11.4 mmol) to obtain compound-A as pale yellow solid (440 mg, 90% yield). $^1$H NMR (400 MHz, CDCl$_3$): δ (ppm): 7.68-7.49 (m, 5H), 3.28-3.21 (m, 2H), 3.19-3.13 (m, 2H); $^{13}$C NMR (100 MHz, CDCl$_3$): δ (ppm): 147.9, 134.3, 133.4, 132.6, 131.4, 131.1, 129.1, 125.7, 17.1, 16.5; MS (EI, m/z): 305 [M]$^+$.

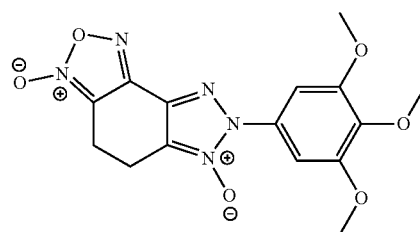

7-(3,4,5-Trimethoxyphenyl)-5,7-dihydro-4H-[1,2,3]triazolo[4',5':3,4]benzo[1,2-c][1,2,5]oxadiazole 3,6-dioxide (8a): Compound 8a was prepared according to the method described in general procedure. Employing compound 7a (500 mg, 1.37 mmol) in 50 ml. of acetonitrile and MnO$_2$ (838 mg, 9.59 mmol) to obtain 8a as brown solid (460 mg, 95% yield). $^1$H NMR (400 MHz, DMSO-d$_6$): δ (ppm): 7.30 (s, 2H), 3.94 (s, 6H), 3.93 (s, 3H), 3.24-3.20 (m, 2H), 3.17-3.13 (m, 2H); $^{13}$C NMR (100 MHz, DMSO-d$_6$): δ (ppm): 147.9, 134.3, 133.4, 132.6, 131.4, 131.1, 129.1, 125.7, 17.1, 16.5; MS (EI, m/z): 363 [M]$^+$.

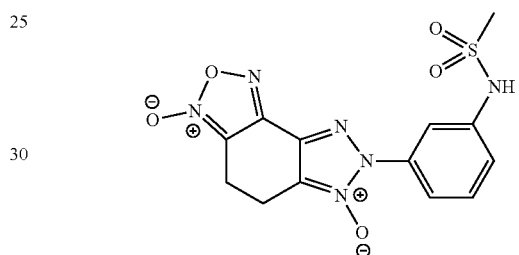

7-(3-(methylsulfonamido)phenyl)-5,7-dihydro-4H-[1,2,3]triazolo[4',5':3,4]benzo[1,2-c][1,2,5]oxadiazole 3,6-dioxide (8b): Compound 8b was prepared according to the method described in general procedure. Employing compound 7b (500 mg, 1.366 mmol) in 50 ml. of acetonitrile and MnO$_2$ (831 mg, 9.56 mmol) to obtain 8b as pale yellow solid (440 mg, 90% yield). $^1$H NMR (400 MHz, DMSO-d$_6$): δ (ppm): 10.21 (bs, 1H), 7.79 (s, 1H), 7.67 (d, J=8.2 Hz, 1H), 7.60 (t, J=8.1 Hz, 1H), 7.39 (d, J=8.1 Hz, 1H), 3.32 (s, 3H), 3.01 (s, 4H); $^{13}$C NMR (100 MHz, DMSO-d$_6$): δ (ppm): 147.8, 139.8, 135.2, 132.5, 130.9, 1272, 120.7, 118.6, 113.9, 112.9, 17.1, 16.6; MS (EI, m/z): 366 [M]$^+$.

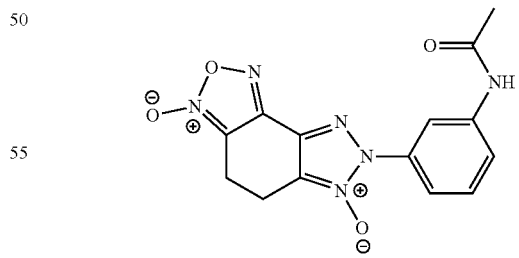

7-(3-acetamidophenyl)-5,7-dihydro-4H-[1,2,3]triazolo[4',5':3,4]benzo[1,2-c][1,2,5]oxadiazole 3,6-dioxide (8c): Compound 8c was prepared according to the method described in general procedure. Employing compound 7c (500 mg, 1.5 mmol) in 50 ml. of acetonitrile and MnO$_2$ (921 mg, 10.6 mmol) to obtain 8c as pale yellow solid (457 mg, 92% yield). $^1$H NMR (400 MHz, DMSO-d$_6$): δ (ppm): 10.31

(bs, 1H), 8.28 (s, 1H), 7.69 (d, J=8.0 Hz, 1H), 7.61 (d, J=8.5 Hz, 1H), 7.55 (t, J=8.1 Hz, 1H), 3.08 (s, 4H), 2.09 (s, 3H); $^{13}$C NMR (100 MHz, DMSO-d$_6$): δ (ppm): 169.2, 147.8, 140.6, 134.8, 132.4, 130.1, 127.2, 120.3, 118.2, 114.0, 112.9, 24.5, 17.1, 16.6; MS (EI, m/z): 330 [M]$^+$.

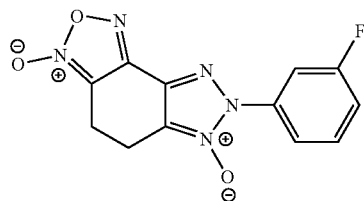 [SMILES: [O-][n+]1onc2c1CCc1c-2nn(-c2cccc(F)c2)[n+]1[O-]]

7-(3-fluorophenyl)-5,7-dihydro-4H-[1,2,3]triazolo[4',5': 3,4]benzo[1,2-c][1,2,5]oxadiazole 3,6-dioxide (8d): Compound 8d was prepared according to the method described in general procedure. Employing compound 7d (500 mg, 1.36 mmol) in 50 ml. of acetonitrile and MnO$_2$ (1.04 g, 11.97 mmol) to obtain 8d as pale yellow solid (450 mg, 92% yield). $^1$H NMR (400 MHz, DMSO-d$_6$): δ (ppm): 7.91-7.87 (m, 1H), 7.82-7.80 (m, 1H), 7.51-7.46 (m, 1H), 3.09 (s, 4H)); $^{13}$C NMR (100 MHz, DMSO-d$_6$): δ (ppm): 163.3, 160.8, 147.7, 135.6, 132.8, 131.9, 127.3, 119.9, 117.4, 112.9, 111.0, 17.0, 16.6; MS (EI, m/z): 289 [M]$^+$.

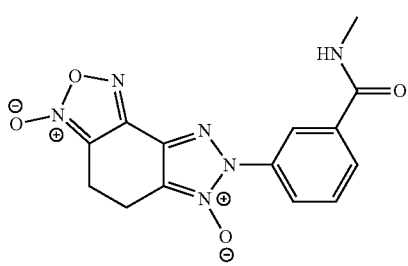 [SMILES: CNC(=O)c1cccc(-n2nc3c([n+]2[O-])CCc2c-3no[n+]2[O-])c1]

7-(3-(methylcarbamoyl)phenyl)-5,7-dihydro-4H-[1,2,3] triazolo[4',5':3,4]benzo[1,2-c][1,2,5]oxadiazole 3,6-dioxide (8e): Compound 8e was prepared according to the method described in general procedure. Employing compound 7e (500 mg, 1.5 mmol) in 50 ml. of acetonitrile and MnO$_2$ (921 mg, 10.6 mmol) to obtain 8a as pale yellow solid (457 mg, 92% yield). $^1$H NMR (400 M Hz, DMSO-d$_6$): δ (ppm): 8.70 (bs, 1H), 8.35 (t, J=1.84 Hz, 1H), 8.12-8.03 (m, 2H), 7.75 (t, J=7.9 Hz, 1H), 3.09 (s, 4H), 2.82 (d, J=4.5 Hz, 3H); $^{13}$C NMR (100 MHz, DMSO-d$_6$): δ (ppm); MS (EI, m/z): 328 [M]$^+$.

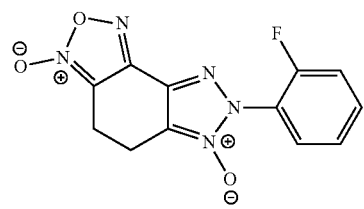 [SMILES: [O-][n+]1onc2c1CCc1c-2nn(-c2ccccc2F)[n+]1[O-]]

7-(2-fluorophenyl)-5,7-dihydro-4H-[1,2,3]triazolo[4',5': 3,4]benzo[1,2-c][1,2,5]oxadiazole 3,6-dioxide (8f): Compound 8f was prepared according to the method described in general procedure. Employing compound 7f (500 mg, 1.71 mmol) in 50 ml. of acetonitrile and MnO$_2$ (1.04 g, 11.97 mmol) to obtain 8f as pale yellow solid (450 mg, 92% yield). $^1$H NMR (400 MHz, CDCl$_3$): δ (ppm): 7.68-7.59 (m, 2H), 7.42-7.35 (m, 2H), 3.26-3.22 (m, 2H), 3.17-3.13 (m, 2H); $^{13}$C NMR (100 MHz, CDCl$_3$): δ (ppm): 158.5, 156.0, 147.8, 134.6, 133.7, 130.3, 126.0, 125.9, 121.4, 117.6, 112.9, 17.1, 16.6; MS (EI, m/z): 289 [M]$^+$.

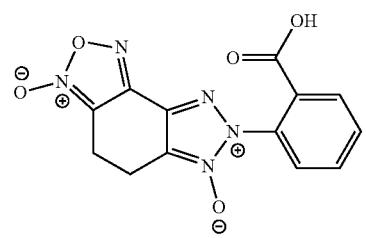

7-(2-carboxyphenyl)-5,7-dihydro-4H-[1,2,3]triazolo[4', 5':3,4]benzo[1,2-c][1,2,5]oxadiazole 3,6-dioxide (8g): Compound 8g was prepared according to the method described in general procedure. Employing compound 7g (500 mg, 1.57 mmol) in 50 ml. of acetonitrile and MnO$_2$ (960 mg, 11.04 mmol) to obtain 8g as pale yellow solid (450 mg, 91% yield). $^1$H NMR (400 MHz, DMSO-d$_6$): δ (ppm): 13.42 (bs, 1H), 8.06 (d, J=8.2 Hz, 1H), 7.87-7.76 (m, 2H), 3.07 (s, 4H); MS (EI, m/z): 315 [M]$^+$.

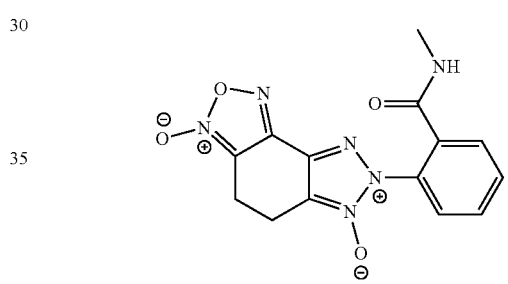

7-(2-(methylcarbamoyl)phenyl)-5,7-dihydro-4H-[1,2,3] triazolo[4',5':3,4]benzo[1,2-c][1,2,5]oxadiazole 3,6-dioxide (8h): Compound 8h was prepared according to the method described in general procedure. Employing compound 7h (500 mg, 1.5 mmol) in 50 ml. of acetonitrile and MnO$_2$ (921 mg, 10.6 mmol) to obtain 8h as pale yellow solid (450 mg, 92% yield). $^1$H NMR (400 MHz, DMSO-d$_6$): δ (ppm): 8.57 (bs, 1H), 7.80-7.69 (m, 4H), 3.12-3.02 (m, 4H), 2.69-2.65 (m, 3H); $^{13}$C NMR (100 MHz, DMSO-d$_6$): δ (ppm): 165.8, 147.9, 134.1, 132.0, 131.7, 131.6, 129.0, 128.9, 125.6, 112.9, 26.6, 17.1, 16.4; MS (EI, m/z): 328 [M]$^+$.

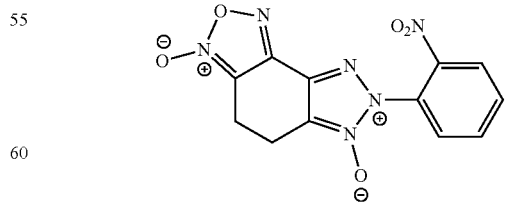

7-(2-nitrophenyl)-5,7-dihydro-4H-[1,2,3]triazolo[4',5':3, 4]benzo[1,2-c][1,2,5]oxadiazole 3,6-dioxide (8i): Compound 8i was prepared according to the method described in general procedure. Employing compound 7i (500 mg, 1.57 mmol) in 50 ml. of acetonitrile and MnO$_2$ (956 mg, 11.0 mmol) to obtain 8i as pale yellow solid (457 mg, 92% yield). $^1$H NMR (400 MHz, DMSO-d$_6$): δ (ppm): 7.68-7.49 (m, 5H), 3.28-3.21 (m, 2H), 3.19-3.13 (m, 2H); MS (EI, m/z): 316 [M]$^+$.

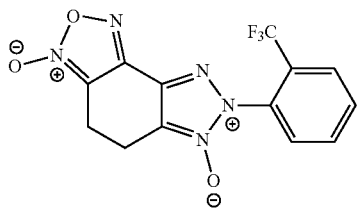

7-(2-(trifluoromethyl)phenyl)-5,7-dihydro-4H-[1,2,3]triazolo[4',5':3,4]benzo[1,2-c][1,2,5]oxadiazole 3,6-dioxide (8j): Compound 8j was prepared according to the method described in general procedure. Employing compound 7j (500 mg, 1.46 mmol) in 50 ml. of acetonitrile and MnO$_2$ (892 mg, 10.26 mmol) to obtain 8j as pale yellow solid (462 mg, 93% yield). $^1$H NMR (400 MHz, DMSO-d$_6$): δ (ppm): 8.12 (d, J=8.7 Hz, 1H), 8.01 (q, J=7.6, 7.1 Hz, 2H), 7.88 (d, J=7.2 Hz, 1H), 3.10 (s, 4H); $^{13}$C NMR (100 MHz, DMSO-d$_6$): δ (ppm): 156.6, 147.7, 134.1, 133.6, 132.1, 130.0, 128.2, 125.1, 112.9, 17.1, 16.5; MS (EI, m/z): 339 [M].

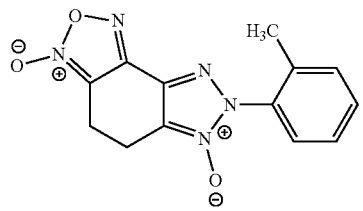 [SMILES: Cc1ccccc1-n1nc2c([n+]1[O-])CCc1c-2no[n+]1[O-]]

7-(o-tolyl)-5,7-dihydro-4H-[1,2,3]triazolo[4',5':3,4]benzo[1,2-c][1,2,5]oxadiazole 3,6-dioxide (8k): Compound 8k was prepared according to the method described in general procedure. Employing compound 7k (500 mg, 1.74 mmol) in 50 ml. of acetonitrile and MnO$_2$ (1.06 g, 12.19 mmol) to obtain 8k as pale yellow solid (460 mg, 92% yield). $^1$H NMR (400 MHz, CDCl$_3$): δ (ppm): 7.55-7.51 (m, 1H), 7.45-7.37 (m, 3H), 3.28-3.21 (m, 4H), 2.28 (s, 3H); $^{13}$C NMR (100 MHz, CDCl$_3$): δ (ppm): 146.3, 137.0, 132.8, 131.9, 131.8, 131.4, 127.9, 127.0, 124.4, 110.4, 17.8, 17.0, 16.5; MS (EI, m/z): 285 [M]$^+$.

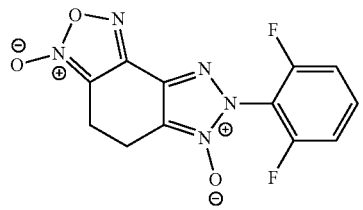 [SMILES: [O-][n+]1onc2c1CCc1c-2nn(-c2c(F)cccc2F)[n+]1[O-]]

7-(2,6-difluorophenyl)-5,7-dihydro-4H-[1,2,3]triazolo[4',5':3,4]benzo[1,2-c][1,2,5]oxadiazole 3,6-dioxide (8l): Compound 8l was prepared according to the method described in general procedure. Employing compound 7l (500 mg, 1.61 mmol) in 50 ml. of acetonitrile and MnO$_2$ (892 mg, 10.26 mmol) to obtain 8l as pale yellow solid (463 mg, 93% yield). $^1$H NMR (400 MHz, DMSO-d$_6$): δ (ppm): 7.95-7.86 (m, 1H), 7.59-7.51 (m, 3H), 3.10 (s, 4H); $^{13}$C NMR (100 MHz, DMSO-d$_6$): δ (ppm): 159.8, 157.2, 136.1, 133.2, 125.9, 113.7, 13.6, 110.8, 17.0, 16.6; MS (EI, m/z): 307 [M]

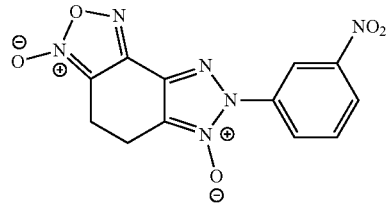 [SMILES: O=[N+]([O-])c1cccc(-n2nc3c([n+]2[O-])CCc2c-3no[n+]2[O-])c1]

7-(3-nitrophenyl)-5,7-dihydro-4H-[1,2,3]triazolo[4',5':3,4]benzo[1,2-c][1,2,5]oxadiazole 3,6-dioxide (8m): Compound 8m was prepared according to the method described in general procedure. Employing compound 7m (500 mg, 1.57 mmol) in 50 ml. of acetonitrile and MnO$_2$ (950 mg, 11.0 mmol) to obtain 8m as pale yellow solid (467 mg, 94% yield). $^1$H NMR (400 MHz, DMSO-d$_6$): δ (ppm): 8.85 (s, 1H), 8.44-8.39 (m, 2H), 7.95 (t, J=8.2 Hz, 1H), 3.11 (s, 4H); $^{13}$C NMR (100 MHz, DMSO-d$_6$): δ (ppm): 148.3, 147.6, 135.0, 133.2, 131.6, 129.5, 127.5, 124.7, 118.7, 112.9, 17.1, 16.6; MS (EI, m/z): 367 [M]$^+$.

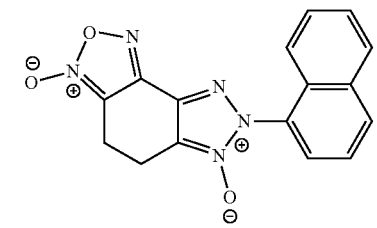 [SMILES: [O-][n+]1onc2c1CCc1c-2nn(-c2cccc3ccccc23)[n+]1[O-]]

7-(naphthalen-1-yl)-5,7-dihydro-4H-[1,2,3]triazolo[4',5':3,4]benzo[1,2-c][1,2,5]oxadiazole 3,6-dioxide (8n): Compound 8n was prepared according to the method described in general procedure. Employing compound 7n (500 mg, 1.54 mmol) in 50 ml. of acetonitrile and MnO$_2$ (940 mg, 10.83 mmol) to obtain 8n as pale yellow solid (450 mg, 91% yield). $^1$H NMR (400 MHz, DMSO-d$_6$): δ (ppm): 8.32 (d, J=8.2 Hz, 1H), 8.15 (d, J=8.6 Hz, 1H), 7.89 (d, J=7.3 Hz, 1H), 7.77 (t, J=7.9 Hz, 1H), 7.72-7.69 (m, 2H), 7.48 (d, J=7.1 Hz, 1H), 3.14 (s, 4H); $^{13}$C NMR (100 MHz, DMSO-d$_6$): δ (ppm): 147.9, 134.3, 133.4, 132.6, 131.4, 131.1, 129.1, 125.7, 17.1, 16.5; MS (EI, m/z): 321 [M]$^+$.

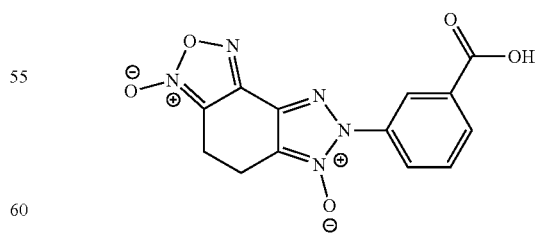

7-(3-carboxyphenyl)-5,7-dihydro-4H-[1,2,3]triazolo[4',5':3,4]benzo[1,2-c][1,2,5]oxadiazole 3,6-dioxide (8o): Compound 8o was prepared according to the method described in general procedure. Employing compound 7o (500 mg, 1.57 mmol) in 50 ml. of acetonitrile and MnO$_2$ (960 mg, 11.04 mmol) to obtain 8o as pale yellow solid (462 mg, 95% yield). $^1$H NMR (400 MHz, DMSO-d$_3$): δ (ppm): 13.21 (bs, 1H), 8.46 (s, 1H), 8.12 (d, J=7.9 Hz, 2H), 7.75 (t, J=7.9 Hz, 1H), 3.09 (s, 4H); $^{13}$C NMR (100 MHz, DMSO-d$_6$): δ (ppm): 147.9, 134.3, 133.4, 132.6, 131.4, 131.1, 129.1, 125.7, 17.1, 16.5; MS (EI, m/z): 315 [M]$^+$.
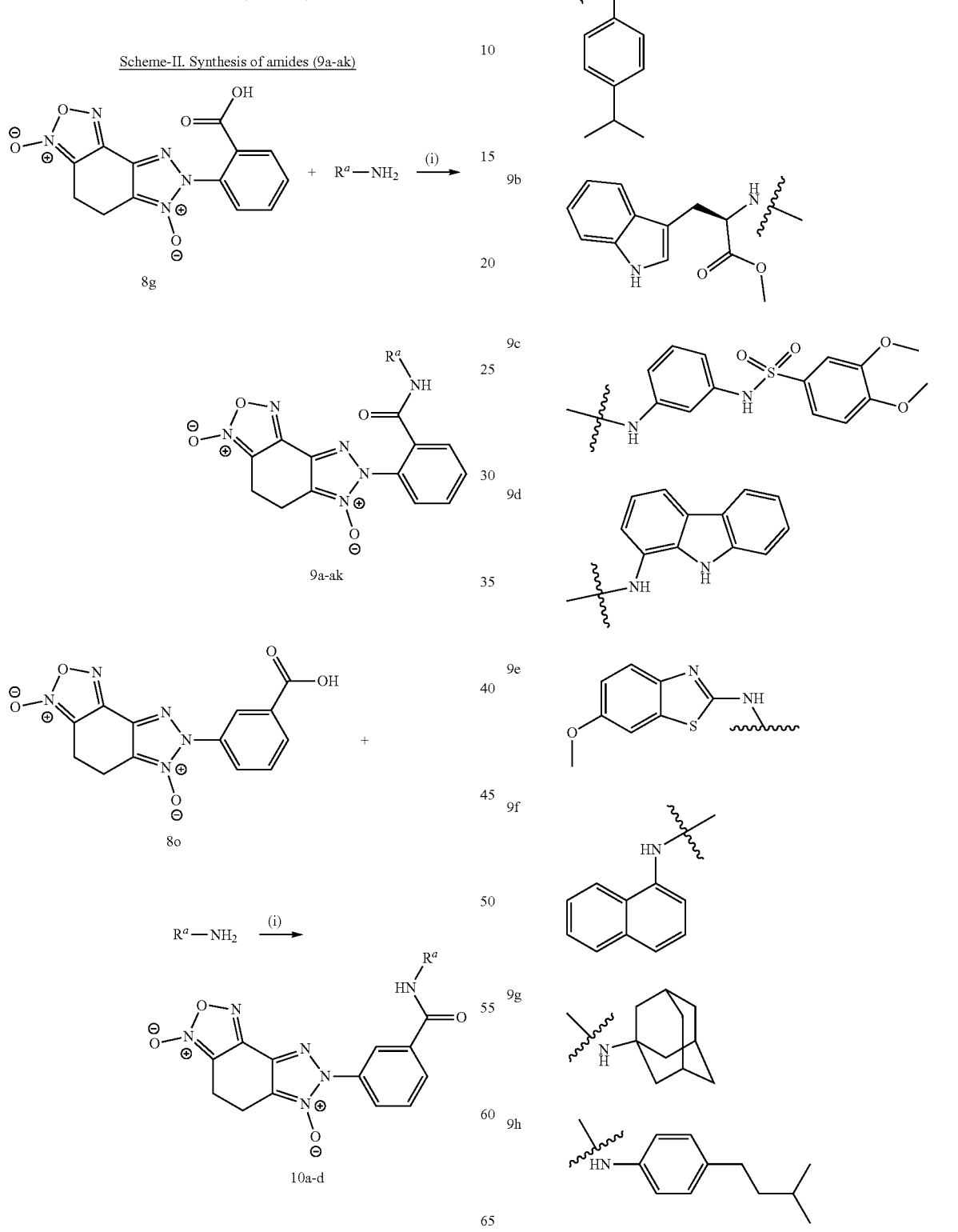
Reagents and conditions: 8g/8o and Corresponding Amines (i) HATU, DIPEA and Dry DMF 25° C., 4 h (90%).

-continued
| Compound | Rᵃ |
|---|---|
| 9i | 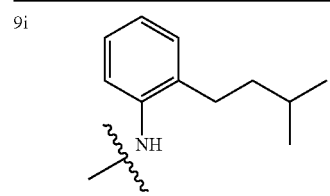 |
| 9j | 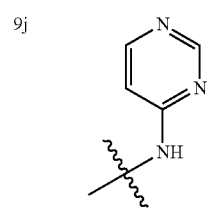 |
| 9k | 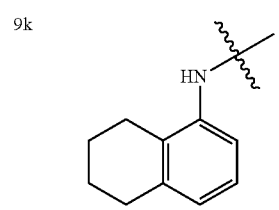 |
| 9l | 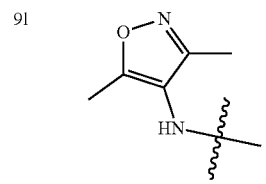 |
| 9m | 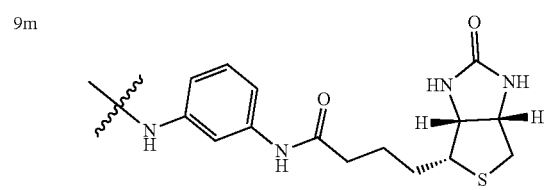 |
| 9n | 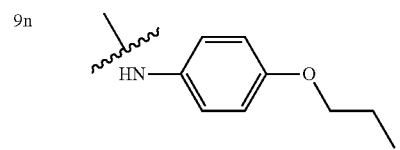 |
| 9o | 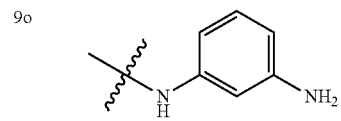 |
| 9p | 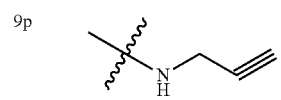 |
| 9q | 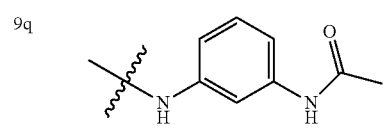 |
-continued
| Compound | Rᵃ |
|---|---|
| 9r | 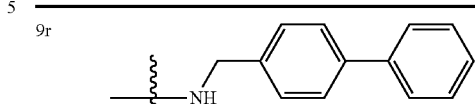 |
| 9s | 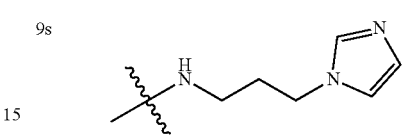 |
| 9t | 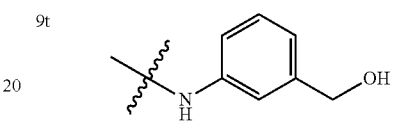 |
| 9u | 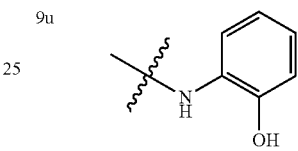 |
| 9v | 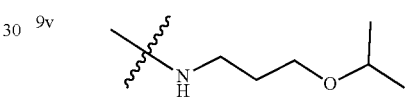 |
| 9w | 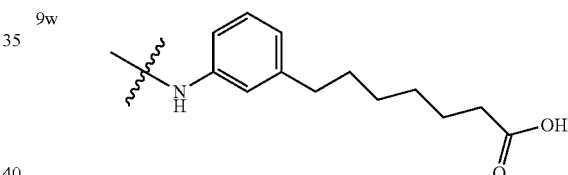 |
| 9x | 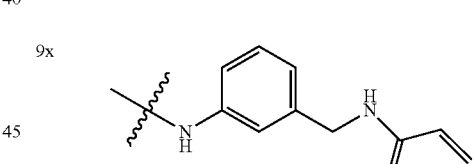 |
| 9y | 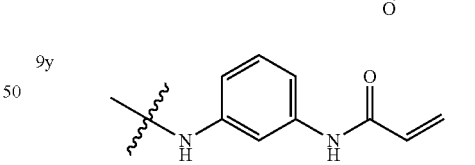 |
| 9z | 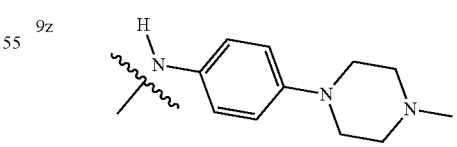 |
| 9aa | 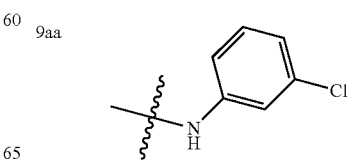 |

| Compound | R$^a$ |
|---|---|
| 9ab | |
| 9ac | |
| 9ad | |
| 9af | |
| 9ag | |
| 9ah | |
| 9ai | |
| 9aj | |
| 9ak | |

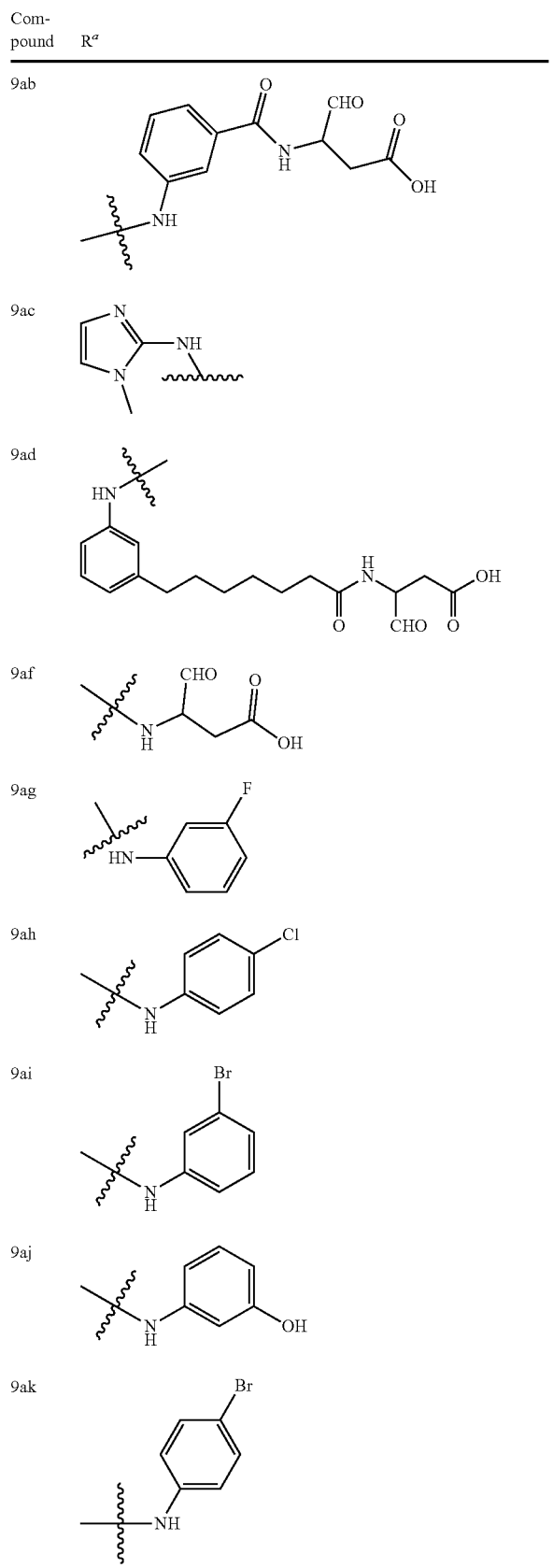

| Compound | R$^a$ |
|---|---|
| 10a | |
| 10b | |
| 10c | |
| 10d | |

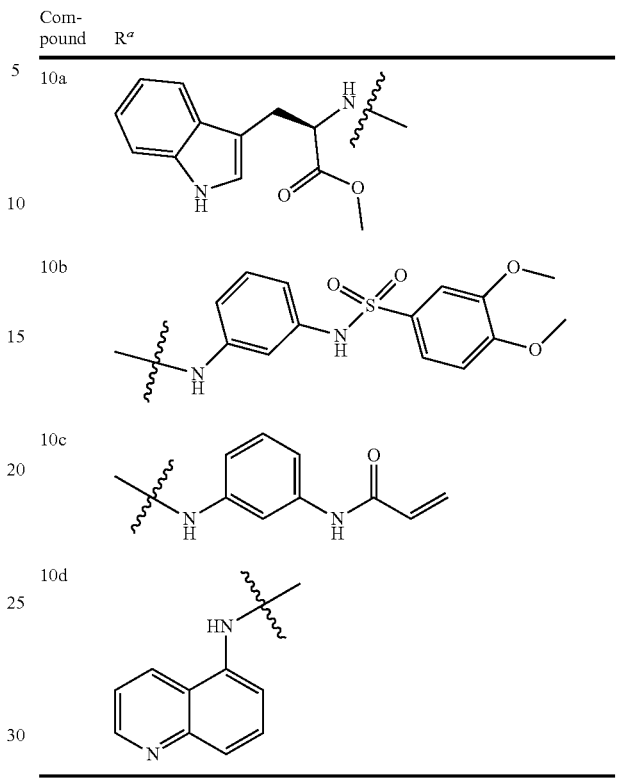

General procedure for synthesis of compounds (9a-ak): To a solution of compounds 8g/8o (1 equi) in Dry DMF (50 times), HATU (1 equi) and DIPEA (3 equi) were added followed by corresponding amines (1 equi). The reaction mixture was stirred at 25° C. for 2-3 h. (until all the starting material has disappeared, TLC monitoring). After completion of the reaction, Ice cold water (100 mL) was added and extracted with ethyl acetate (2×50 mL). The combined organic layers were washed with brine, dried over Na2SO4, filtered, and concentrated to give a crude product, which was purified by column chromatography (silica gel 120-200 mesh), eluting with cyclohexane/EtOAc (from 100:0 to 40:60) to afford with high purity (9a-ak).

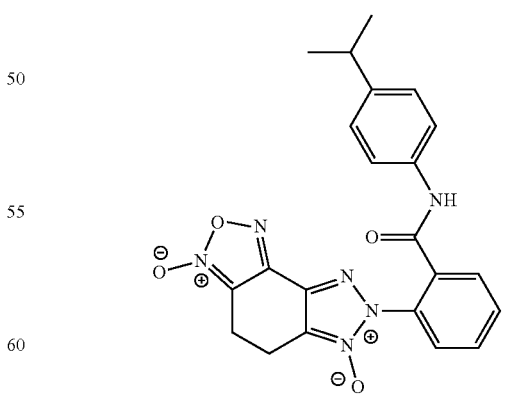

7-(2-((4-isopropylphenyl)carbamoyl)phenyl)-5,7-dihydro-4H [1,2,3]triazolo[4',5':3,4]benzo[1,2-c][1,2,5]oxadiazole 3,6-dioxide (9a): Compound 9a was prepared according to the method described in general procedure.

Employing compound 8g (200 mg, 0.63 mmol) in 10 mL Dry DMF, HATU (289 mg, 0.76 mmol), DIPEA (0.34 mL 1.9 mmol) and 4-isopropylaniline (0.63 mmol) to obtain 9a as a brown solid (230 mg, 84% yield). $^1$H NMR (400 MHz, DMSO-$d_6$): δ (ppm): 10.55 (bs, 1H), 8.01-7.22 (m, 4H), 7.61-7.45 (m, 2H), 7.22-7.10 (m, 2H), 3.12-2.75 (m, 5H), 1.18 (s, 6H); $^{13}$C NMR (100 MHz, DMSO-$d_6$): δ (ppm): 164.0, 147.8, 144.3, 137.2, 134.0, 132.0, 131.6, 129.5, 128.6, 126.7, 125.8, 120.5, 112.9, 33.3, 24.4, 171, 16.4; MS (ESI, m/z): 433.1431[M+1]+.

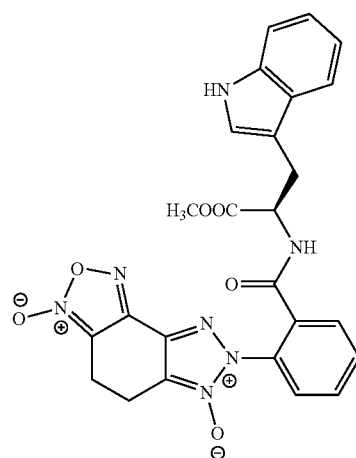

(R)-7-(2-((3-(1H-indol-3-yl)-1-methoxy-1-oxopropan-2-yl)carbamoyl)phenyl)-5,7-dihydro-4H-[1,2,3]triazolo[4',5':3,4]benzo[1,2-c][1,2,5]oxadiazole 3,6-dioxide (9b): Compound 9b was prepared according to the method described in general procedure. Employing compound 8g (200 mg, 0.63 mmol) in 10 mL Dry DM, HATU (289 mg, 0.76 mmol), DIPEA (0.34 mL 1.9 mmol) and methyl D-tryptophanate (0.63 mmol) to obtain 9b as a pale yellow solid (280 mg, 86% yield). $^1$H NMR (400 MHz, DMSO-$d_6$): δ (ppm): 10.83 (bs, 1H), 9.05 (s, 1H), 7.95-6.84 (m, 8H), 4.58 (s, 1H), 3.57 (s, 3H), 3.42-2.82 (m, 5H), 2.42 (m, 2H); $^{13}$C NMR (100 MHz, DMSO-$d_6$): δ (ppm): 172.2, 165.3, 147.7, 136.5, 133.7, 132.0, 131.8, 129.6, 128.9, 127.4, 125.7, 123.9, 121.4, 118.8, 118.3, 112.7, 111.8, 109.9, 53.8, 52.3, 27.2, 16.9, 16.2; MS (ESI, m/z): 516.1891 [M+1]+.

9c was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and N-(3-aminophenyl)-3,4-dimethoxybenzenesulfonamide (0.63 mmol) to obtain 9c as a brown solid (326 mg, 85% yield). $^1$H NMR (400 MHz, DMSO-$d_6$): δ (ppm): 10.68 (bs, 1H), 10.12 (s, 1H), 8.05-7.70 (m, 5H), 7.59 (s, 1H), 7.43-7.21 (m, 3H), 7.18-7.02 (m, 2H), 6.87-6.73 (m, 1H), 3.78 (s, 3H), 3.73 (s, 3H), 3.15-2.93 (m, 4H); $^{13}$C NMR (100 MHz, DMSO-$d_6$): δ (ppm): 164.2, 162.7, 152.5, 148.8, 147.8, 140.1, 138.7, 133.7, 132.3, 131.6, 129.6, 128.5, 125.9, 120.8, 115.9, 115.5, 112.8, 111.8, 111.6, 110.1, 56.2, 56.1, 17.0, 16.4; MS (ESI, m/z): 606.5816 [M+1]+.

7-(2-((9H-carbazol-1-yl)carbamoyl)phenyl)-5,7-dihydro-4H-[1,2,3]triazolo[4',5':3,4]benzo[1,2-c][1,2,5]oxadiazole 3,6-dioxide (9d): Compound 9d was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and 9H-carbazol-1-amine (115 mg, 0.63 mmol) to obtain 9d as a pale yellow solid (267 mg, 88% yield). $^1$H NMR (400 MHz, DMSO-$d_6$): δ (ppm): 11.20 (bs, 1H), 10.62 (s, 1H), 8.37 (s, 1H), 8.0 (d, J=6.4 Hz, 2H), 7.82 (d, J=8.1 Hz, 2H), 7.60-7.33 (m 4H), 7.13 (t, J=7.3 Hz, 1H), 3.05 (s, 4H); $^{13}$C NMR (100 MHz, DMSO-$d_6$): δ (ppm): 170.8, 163.9, 147.8, 140.7, 137.1, 14.4, 132.2, 131.8, 131.7, 129.0, 128.7, 126.0, 125.8, 122.7, 122.4, 120.4, 120.0, 118.9, 112.9, 112.7, 111.5, 111.1, 17.1, 16.4; MS (ESI, m/z): 480.1415 [M+1]+.

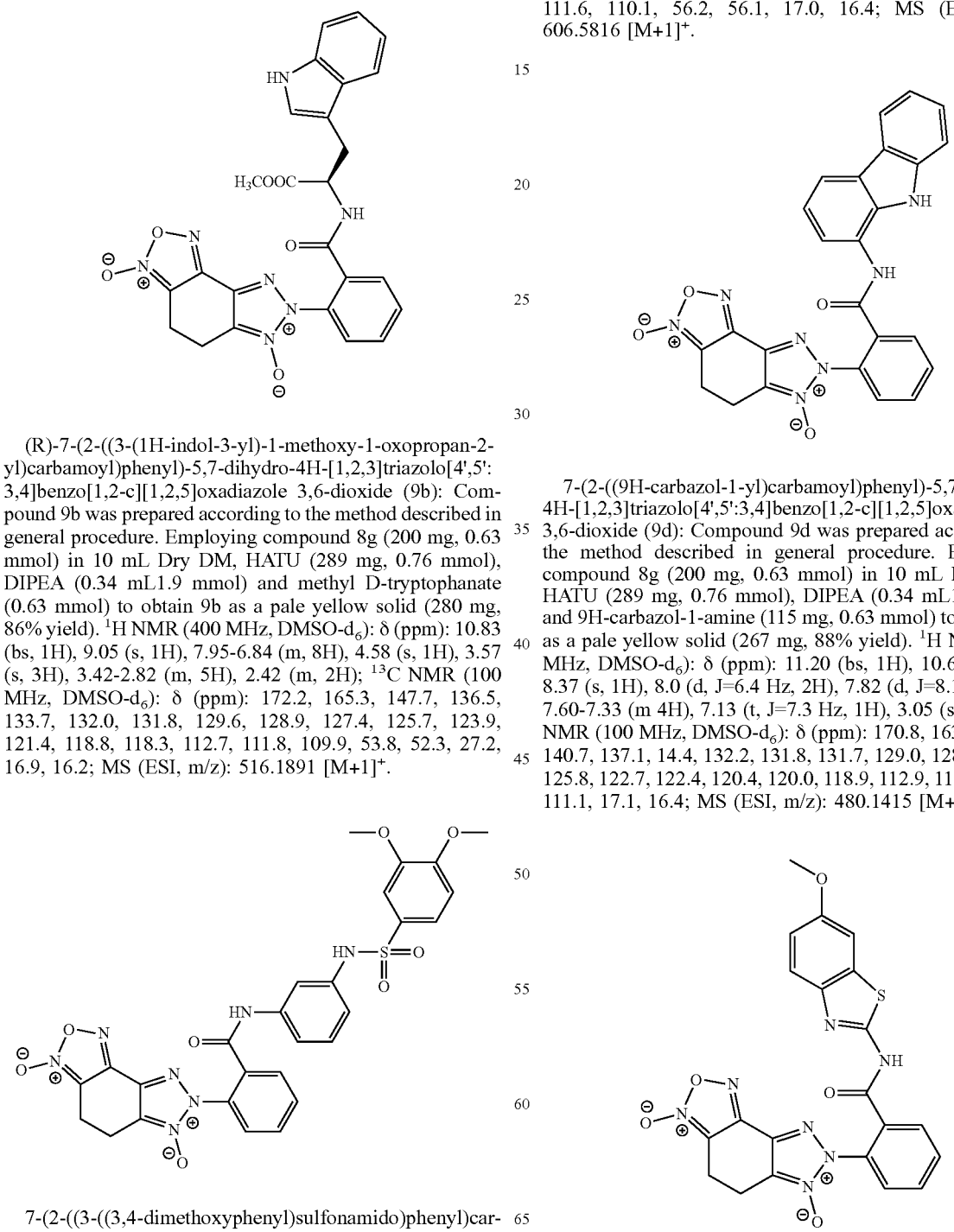

7-(2-((3-((3,4-dimethoxyphenyl)sulfonamido)phenyl)carbamoyl)phenyl)-5,7-dihydro-4H-[1,2,3]triazolo[4',5':3,4]benzo[1,2-c][1,2,5]oxadiazole 3,6-dioxide (9c): Compound 7-(2-((6-methoxybenzo[d]thiazol-2-yl)carbamoyl)phenyl)-5,7-dihydro-4H-[1,2,3]triazolo[4',5':3,4]benzo[1,2-c][1,2,5]oxadiazole 3,6-dioxide (9e): Compound 9e was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and 6-methoxybenzo[d]thiazol-2-amine (114 mg, 0.63 mmol) to obtain 9e as a yellow solid (248 mg, 82% yield). $^1$H NMR (400 MHz, DMSO-$d_6$): δ (ppm): 13.0 (bs, 1H), 8.15-7.59 (m, 5H), 7.55 (s, 1H), 7.06 (d, J=9.1 Hz, 1H), 3.81 (s, 3H), 3.16-2.92 (m, 4H); $^{13}$C NMR (100 MHz, DMSO-$d_6$): δ (ppm): 164.8, 156.7, 147.7, 143.1, 133.3, 133.1, 132.6, 131.6, 131.5, 130.8, 129.9, 128.1, 126.1, 121.7, 115.5, 112.9, 105.1, 56.1, 17.0, 16.4; MS (ESI, m/z): 478.0928 [M+1]$^+$.

9g as a pale yellow solid (236 mg, 82% yield). $^1$H NMR (400 MHz, DMSO-$d_6$): δ (ppm): 7.95 (bs, 1H), 7.76-7.63 (m, 4H), 3.07 (s, 4H), 1.99 (s, 4H), 1.95 (s, 5H), 1.60 (s, 6H); $^{13}$C NMR (100 MHz, DMSO-$d_6$): δ (ppm): 170.7, 165.0, 156.6, 147.8, 135.0, 132.0, 131.5, 130.9, 129.4, 128.3, 125.7, 124.1, 112.9, 60.2, 52.0, 40.9, 36.5, 29.2, 17.1, 16.4; MS (ESI, m/z): 449.1932 [M+1]$^+$.

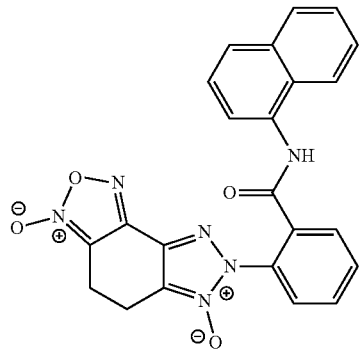 [SMILES: O=C(Nc1cccc2ccccc12)c1ccccc1-n1nc2c([n+]1[O-])CCc1c-2no[n+]1[O-]]

7-(2-(naphthalen-1-ylcarbamoyl)phenyl)-5,7-dihydro-4H-[1,2,3]triazolo[4',5':3,4]benzo[1,2-c][1,2,5]oxadiazole 3,6-dioxide (9f): Compound 9f was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and naphthalen-1-amine (90 mg, 0.63 mmol) to obtain 9f as a brown solid (237 mg, 85% yield). $^1$H NMR (400 MHz, DMSO-$d_6$): δ (ppm): 10.71 (bs, 1H), 8.23-8.13 9 m, 2H), 8.01-7.76 (m, 5H 0, 7.59-7.46 (m, 4H), 3.05 (s, 4H); MS (ESI, m/z): 441.1306 [M+1]$^+$.

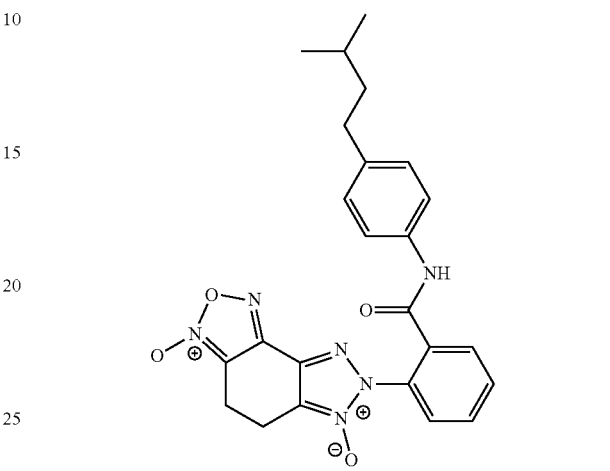

7-(2-((4-isopentylphenyl)carbamoyl)phenyl)-5,7-dihydro-4H-[1,2,3]triazolo[4',5':3,4]benzo[1,2-c][1,2,5]oxadiazole 3,6-dioxide (9h): Compound 9h was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and 4-isopentylaniline (103 mg, 0.63 mmol) to obtain 9h as a yellow solid (251 mg, 86% yield). $^1$H NMR (400 MHz, DMSO-$d_6$): δ (ppm): 10.55 (bs, 1H), 7.98-7.70 (m, 4H), 7.52 (d, J=7.63 Hz, 2H), 7.13 (d, J=7.56 Hz, 2H), 3.04 (s, 4H), 2.53 (m, 2H), 1.58-1.34 (m, 3H), 0.91 (s, 3H), 0.89 (s, 3H); $^{13}$C NMR (100 MHz, DMSO-$d_6$): δ (ppm):164.0, 147.8, 138.4, 137.1, 134.0, 132.2, 132.0, 131.6, 129.5, 128.7, 128.6, 125.8, 124.3, 120.5, 112.8, 32.9, 27.4, 22.8, 17.0, 16.4; MS (ESI, m/z): 461.1284 [M+1]$^+$.

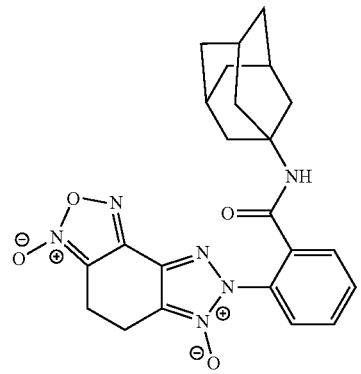 [SMILES: O=C(NC12CC3CC(CC(C3)C1)C2)c1ccccc1-n1nc2c([n+]1[O-])CCc1c-2no[n+]1[O-]]

7-(2-(((3s,5s,7s)-adamantan-1-yl)carbamoyl)phenyl)-5,7-dihydro-4H-[1,2,3]triazolo[4',5':3,4]benzo[1,2-c][1,2,5]oxadiazole 3,6-dioxide (9g): Compound 9g was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and Adamantyl anime (95 mg, 0.63 mmol) to obtain

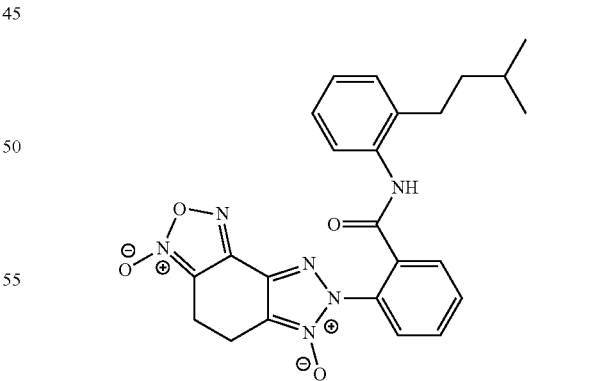

7-(2-((2-isopentylphenyl)carbamoyl)phenyl)-5,7-dihydro-4H-[1,2,3]triazolo[4',5':3,4]benzo[1,2-c][1,2,5]oxadiazole 3,6-dioxide (9i): Compound 9i was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and 2-isopentylaniline (114 mg, 0.63 mmol) to obtain 9i as a pale yellow solid (250 mg, 86% yield). $^1$H NMR (400 MHz, DMSO-d$_6$): δ (ppm): 10.14 (bs, 1H), 8.02-7.76 (m, 4H), 7.32-7.16 (m, 4H), 3.05 (s, 4H), 2.69-2.57 (m, 2H), 1.67-1.31 (m, 3H), 0.90 (s, 6H); $^{13}$C NMR (100 MHz, DMSO-d$_6$): δ (ppm): 164.7, 156.6, 147.8, 139.1, 135.8, 134.0, 132.2, 131.9, 129.6, 129.1, 128.7, 127.9, 126.8, 126.3, 125.8, 29.2, 27.9, 22.9, 17.0, 16.4; MS (ESI, m/z): 461.1428[M+1]$^+$.

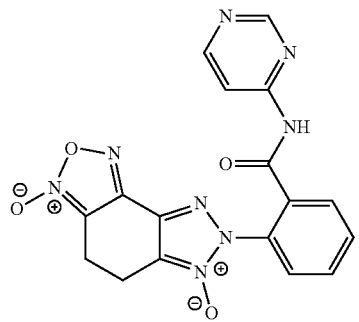 [SMILES: O=C(Nc1ccncn1)c1ccccc1-n1nc2c([n+]1[O-])CCc1c-2no[n+]1[O-]]

7-(2-(pyrimidin-4-ylcarbamoyl)phenyl)-5,7-dihydro-4H-[1,2,3]triazolo[4',5':3,4]benzo[1,2-c][1,2,5]oxadiazole 3,6-dioxide (9j): Compound 9j was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and pyrimidin-4-amine (60 mg, 0.63 mmol) to obtain 9j as a yellow solid (214 mg, 86% yield). $^1$H NMR (400 MHz, DMSO-d$_6$): δ (ppm): 11.64 (bs, 1H), 8.93 (s, 1H), 8.66 (d, J=5.1 Hz, 1H), 8.02-7.95 (m, 2H), 7.88-7.76 (m, 2H), 3.15-2.91 (m, 4H); $^{13}$C NMR (100 MHz, DMSO-d$_6$): δ (ppm): 166.1, 158.7, 158.4, 147.7, 132.8, 132.5, 132.0, 131.5, 131.3, 130.0, 128.0, 126.1, 112.9, 111.0, 17.0, 16.4; MS (ESI, m/z): 393.1055 [M+1]$^+$.

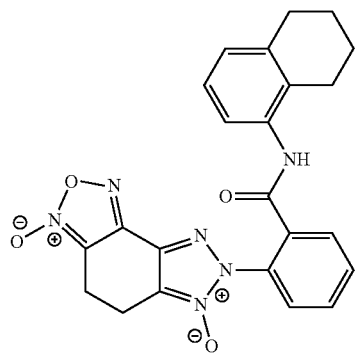 [SMILES: O=C(Nc1cccc2c1CCCC2)c1ccccc1-n1nc2c([n+]1[O-])CCc1c-2no[n+]1[O-]]

7-(2-((5,6,7,8-tetrahydronaphthalen-1-yl)carbamoyl)phenyl)-5,7-dihydro-4H-[1,2,3]triazolo[4',5':3,4]benzo[1,2-c][1,2,5]oxadiazole 3,6-dioxide (9k): Compound 9k was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and 5,6,7,8-tetrahydronaphthalen-1-amine (93 mg, 0.63 mmol) to obtain 9k as a brown solid (228 mg, 81% yield). $^1$H NMR (400 MHz, DMSO-d$_6$): δ (ppm): 10.00 (bs, 1H), 8.10-7.61 (m, 4H), 7.25-6.94 (m, 3H), 3.05 (s, 4H), 2.72 (m, 2H), 2.69 (m, 2H), 1.78-1.62 (m, 4H); MS (ESI, m/z): 445.1257 [M+1]$^+$.

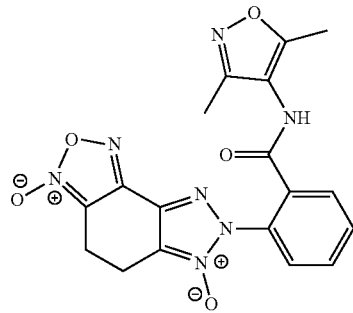 [SMILES: Cc1noc(C)c1NC(=O)c1ccccc1-n1nc2c([n+]1[O-])CCc1c-2no[n+]1[O-]]

7-(2-((3,5-dimethylisoxazol-4-yl)carbamoyl)phenyl)-5,7-dihydro-4H-[1,2,3]triazolo[4',5':3,4]benzo[1,2-c][1,2,5]oxadiazole 3,6-dioxide (9l): Compound 9l was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and 3,5-dimethylisoxazol-4-amine (71 mg, 0.63 mmol) to obtain 9l as a brown solid (215 mg, 83% yield). $^1$H NMR (400 MHz, DMSO-d$_6$): δ (ppm): 10.09 (bs, 1H), 8.03-7.80 (m, 4H), 3.01 (s, 4H), 2.30 (s, 3H), 2.14 (s, 3H); $^{13}$C NMR (100 MHz, DMSO-d$_6$): δ (ppm): 165.0, 163.6, 158.1, 147.8, 133.1, 132.3, 131.7, 131.6, 129.4, 128.5, 125.9, 114.1, 112.9, 171, 16.4, 11.1, 9.8; MS (ESI, m/z): 410.1561 [M+1]$^+$.

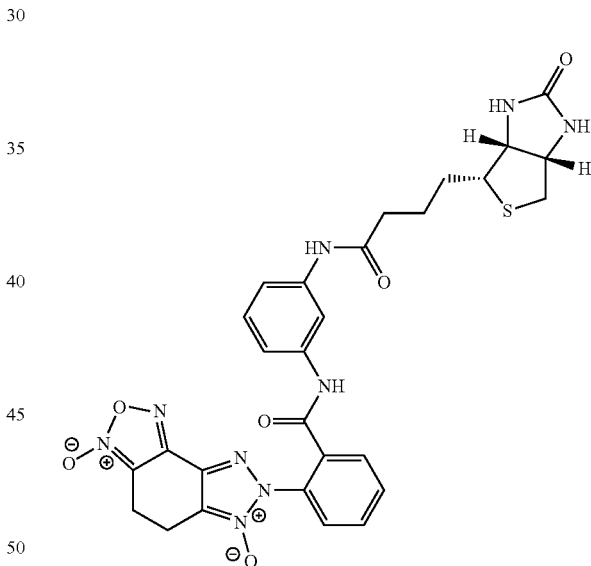

7-(2-((3-(4-((3aR,4R,6aS)-2-oxohexahydro-1H-thieno[3,4-d]imidazol-4-yl)butanamido)phenyl)carbamoyl)phenyl)-5,7-dihydro-4H-[1,2,3]triazolo[4',5':3,4]benzo[1,2-c][1,2,5]oxadiazole 3,6-dioxide (9m): Compound 9m was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and N-(3-aminophenyl)-4-((3aR,4R,6aS)-2-oxohexahydro-1H-thieno[3,4-d]imidazol-4-yl)butanamide (203 mg, 0.63 mmol) to obtain 9e as a pale yellow solid (313 mg, 80% yield). $^1$H NMR (400 MHz, DMSO-d$_6$): δ (ppm): 10.64 (bs, 1H), 9.87 (bs, 1H), 7.98-7.92 (m, 3H), 7.83-7.78 (m, 2H), 7.32-7.18 (m, 3H), 6.43 (s, 1H), 6.36 (s, 1H), 4.32-4.29 (m, 1H), 4.15-4.13 (m, 1H), 3.15-3.01 (m, 4H), 2.83-2.80 (m, 1H), 2.60-2.57 (m, 1H), 2.31-2.27 (m, 2H), 1.67-1.27

(m, 6H); $^{13}$C NMR (100 MHz, DMSO-d$_6$): δ (ppm): 171.6, 164.1, 163.1, 162.7, 147.8, 1399, 139.6, 134.0, 132.3, 132.0, 131.6, 129.6, 129.1, 128.6, 125.8, 115.4, 115.1, 112.8, 111.5, 61.5, 59.6, 55.8, 36.6, 28.7, 28.5, 25.5, 17.0, 16.4, MS (ESI, m/z): 618.1878 [M+1]$^+$.

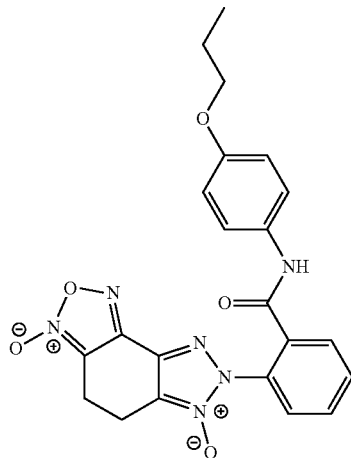 [SMILES: CCCOc1ccc(NC(=O)c2ccccc2-n2nc3c([n+]2[O-])CCc2c-3no[n+]2[O-])cc1]

7-(2-((4-propoxyphenyl)carbamoyl)phenyl)-5,7-dihydro-4H-[1,2,3]triazolo[4',5':3,4]benzo[1,2-c][1,2,5]oxadiazole 3,6-dioxide (9n): Compound 9n was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and 4-propoxyaniline (95 mg, 0.63 mmol) to obtain 9n as a brown solid (238 mg, 84% yield). $^1$H NMR (400 MHz, DMSO-d$_6$): δ (ppm): 10.48 (bs, 1H), 8.02-7.71 (m, 4H), 7.44 (d, J=7.2 Hz, 2H), 6.98 (d, J=7.3 Hz, 2H), 3.97-3.79 (m, 2H), 3.26-2.98 (m, 4H), 1.79-1.59 (m, 2H), 1.06-0.82 (m, 3H); $^{13}$C NMR (100 MHz, DMSO-d$_6$): δ (ppm): 163.7, 155.5, 147.8, 134.1, 132.4, 132.2, 131.9, 131.6, 29.5, 128.6, 125.8, 122.1, 114.8, 112.9, 64.5, 22.5, 17.1, 16.4; MS (ESI, m/z): 449.1568 [M+1]$^+$.

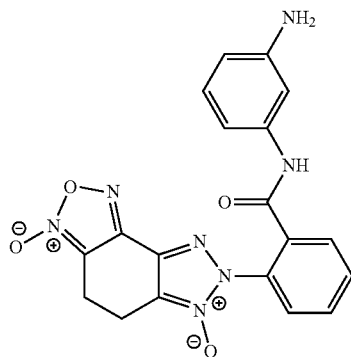 [SMILES: Nc1cccc(NC(=O)c2ccccc2-n2nc3c([n+]2[O-])CCc2c-3no[n+]2[O-])c1]

7-(2-((3-aminophenyl)carbamoyl)phenyl)-5,7-dihydro-4H-[1,2,3]triazolo[4',5':3,4]benzo[1,2-c][1,2,5]oxadiazole 3,6-dioxide (9o): Compound 9o was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and tert-butyl (3-aminophenyl)carbamate (0.63 mmol) followed by Boc deprotection with TFA (10 times in DCM) to obtain 9o as a pale yellow solid (215 mg, 84% yield). $^1$H NMR (400 MHz, DMSO-d$_6$): δ (ppm): 10.34 (bs, 1H), 7.90-7.74 (m, 4H), 6.95-6.90 (m, 2H), 6.72 (d, J=7.9 Hz, 2H), 6.29 (d, J=8.3 Hz, 2H), 5.05 (bs, 2H), 3.05 (s, 4H); $^{13}$C NMR (100 MHz, DMSO-d$_6$): δ (ppm): 163.8, 156.6, 149.3, 147.8, 140.0, 134.4, 132.2, 131.8, 131.6, 129.6, 129.2, 128.6, 125.8, 124.2, 122.7, 112.8, 110.2, 108.4, 106.1, 171, 16.4; MS (ESI, m/z): 406.1258 [M+1]$^+$.

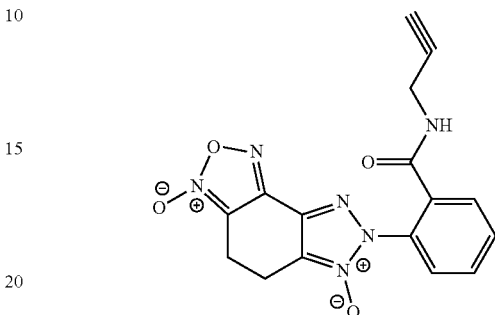

7-(2-(prop-2-yn-1-ylcarbamoyl)phenyl)-5,7-dihydro-4H-[1,2,3]triazolo[4',5':3,4]benzo[1,2-c][1,2,5]oxadiazole 3,6-dioxide (9p): Compound 9p was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and propargylamine (34 mg, 0.63 mmol) to obtain 9p as a pale yellow solid (183 mg, 82% yield). $^1$H NMR (400 MHz, DMSO-d$_6$): δ (ppm): 9.05 (bs, 1H0, 7.85-7.68 (m, 4H), 3.94 (s, 2H), 3.34 (s, 1H), 3.07 (s, 4H); $^{13}$C NMR (100 MHz, DMSO-d$_6$): δ (ppm): 165.0, 147.8, 133.4, 132.1, 132.0, 131.8, 131.6, 129.2, 128.9, 125.7, 112.8, 81.0, 73.6, 28.9, 17.1, 16.4; MS (ESI, m/z): 353.0993 [M+1]$^+$.

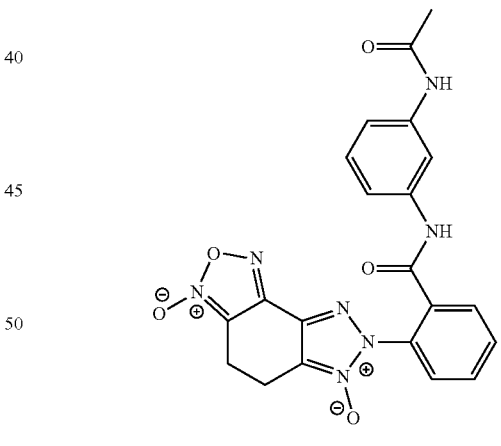

7-(2-((3-acetamidophenyl)carbamoyl)phenyl)-5,7-dihydro-4H-[1,2,3]triazolo[4',5':3,4]benzo[1,2-c][1,2,5]oxadiazole 3,6-dioxide (9q): Compound 9q was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and N-(3-aminophenyl)acetamide (95 mg, 0.63 mmol) to obtain 9q as a brown solid (244 mg, 86% yield). $^1$H NMR (400 MHz, DMSO-d$_6$): δ (ppm): 1097 (bs, 1H), 9.94 (bs, 1H), 8.07-7.67 (m, 5H), 7.38-7.15 (m, 3H), 3.27-3.04 (m, 4H), 2.02 (s, 3H); $^{13}$C NMR (100 MHz, DMSO-d$_6$): δ (ppm): 18.7, 164.1, 156.6, 147.8, 139.9, 139.7, 134.0, 1H), 7.89-7.62 (m, 5H), 7.18 (s, 1H), 6.87 (s, 1H), 4.02-3.98 (m, 2H), 3.28-3.00 (m, 6H), 1.91-1.81 (m, 2H); $^{13}$C NMR (100 MHz, DMSO-d$_6$): δ (ppm): 165.7, 156.5, 147.8, 137.8, 134.2, 132.1, 131.7, 131.6, 129.0, 128.7, 125.8, 124.2, 119.9, 112.8, 43.7, 36.4, 3.0, 17.1, 16.3; MS (ESI, m/z): 423.1524 [M+1]$^+$.

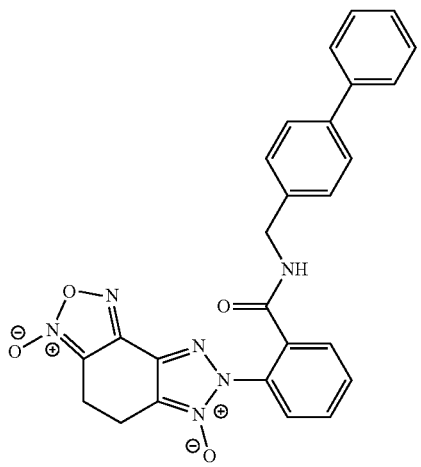 [SMILES: O=C(NCc1ccc(-c2ccccc2)cc1)c1ccccc1-n1nc2c([n+]1[O-])CCc1c-2no[n+]1[O-]]

7-(2-(([1,1'-biphenyl]-4-ylmethyl)carbamoyl)phenyl)-5,7-dihydro-4H-[1,2,3]triazolo[4',5':3,4]benzo[1,2-c][1,2,5]oxadiazole 3,6-dioxide (9r): Compound 9r was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and [1,1'-biphenyl]-4-ylmethanamine (116 mg, 0.63 mmol) to obtain 9r as a brown solid (264 mg, 87% yield). $^1$H NMR (400 MHz, DMSO-d$_6$): δ (ppm): 9.22 (bs, 1H), 7.87-7.76 (m, 4H), 7.65-7.60 (m, 4H), 7.48-7.34 (m, 5H), 4.42 (s, 2H), 3.25-3.05 (m, 4H); $^{13}$C NMR (100 MHz, DMSO-d$_6$): δ (ppm): 165.5, 156.5, 147.8, 140.4, 139.0, 128.5, 134.3, 132.1, 131.8, 131.7, 130.0, 129.3, 128.3, 127.7, 126.9, 126.8, 125.7, 124.1, 42.6, 17.1, 16.4; MS (ESI, m/z): 481.1619 [M+1]$^+$.

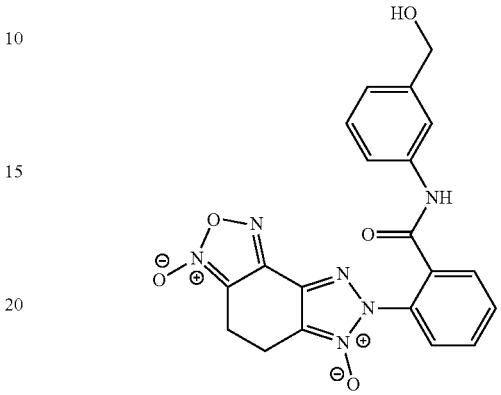

7-(2-((3-(hydroxymethyl)phenyl)carbamoyl)phenyl)-5,7-dihydro-4H-[1,2,3]triazolo[4',5':3,4]benzo[1,2-c][1,2,5]oxadiazole 3,6-dioxide (9t): Compound 9t was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and (3-aminophenyl)methanol (78 mg, 0.63 mmol) to obtain 9t as a brown solid (230 mg, 86% yield). $^1$H NMR (400 MHz, DMSO-d$_6$): δ (ppm): 10.64 (bs, 1H), 7.93-7.62 (m, 5H), 7.48 (s, 1H), 7.26-7.24 (m, 1H), 7.03-7.02 (m, 1H), 5.21 (bs, 1H), 4.46 (s, 2H), 3.27-3.04 (m, 4H); $^{13}$C NMR (100 MHz, DMSO-d$_6$): δ (ppm): 164.1, 156.6, 147.8, 143.5, 139.3, 134.0, 132.3, 132.0, 131.6, 129.5, 128.7, 125.9, 124.3, 122.3, 118.9, 118.6, 112.9, 106.4, 63.03, 17.0, 16.4; MS (ESI, m/z): 421.1255 [M+1]$^+$.

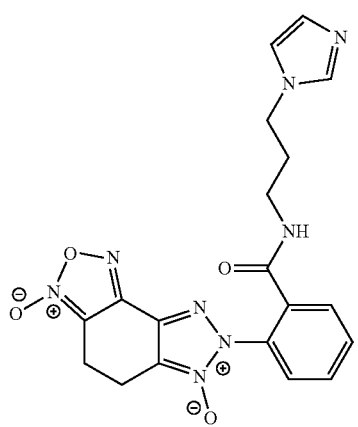 [SMILES: O=C(NCCCn1ccnc1)c1ccccc1-n1nc2c([n+]1[O-])CCc1c-2no[n+]1[O-]]

7-(2-((3-(1H-imidazol-1-yl)propyl)carbamoyl)phenyl)-5,7-dihydro-4H-[1,2,3]triazolo[4',5':3,4]benzo[1,2-c][1,2,5]oxadiazole 3,6-dioxide (9s): Compound 9s was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and 3-(1H-imidazol-1-yl)propan-1-amine (79 mg, 0.63 mmol) to obtain 9s as a yellow solid (214 mg, 80% yield). $^1$H NMR (400 MHz, DMSO-d$_6$): δ (ppm): 8.74 (bs,

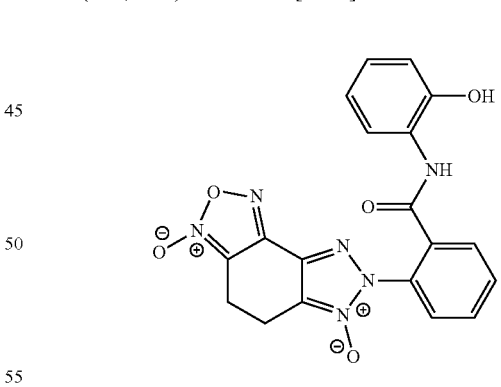

7-(2-((2-hydroxyphenyl)carbamoyl)phenyl)-5,7-dihydro-4H-[1,2,3]triazolo[4',5':3,4]benzo[1,2-c][1,2,5]oxadiazole 3,6-dioxide (9u): Compound 9u was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and 2-amino phenol (69 mg, 0.63 mmol) to obtain 9u as a brown solid (226 mg, 88% yield). $^1$H NMR (400 MHz, DMSO-d$_6$): δ (ppm): 9.65 (bs, 1H), 9.46 (bs, 1H), 8.03-7.52 (m, 3H), 7.06-6.73 (m, 3H), 3.05 (s, 4H); MS (ESI, m/z): 407.1814 [M+1]$^+$.

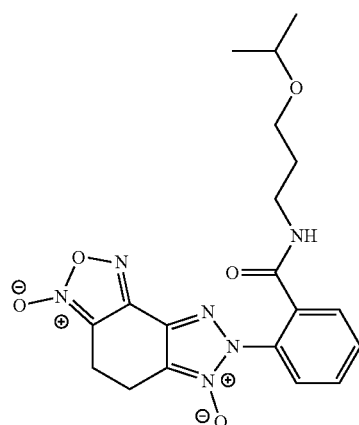

7-(2-((3-isopropoxypropyl)carbamoyl)phenyl)-5,7-dihydro-4H-[1,2,3]triazolo[4',5':3,4]benzo[1,2-c][1,2,5]oxadiazole 3,6-dioxide (9v): Compound 9v was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and 3-isopropoxypropan-1-amine (74 mg, 0.63 mmol) to obtain 9v as a pale yellow solid (228 mg, 87% yield). $^1$H NMR (400 MHz, DMSO-d$_6$): δ (ppm): 8.60 (bs, 1H), 7.77-7.70 (m, 4H), 3.52-3.46 (m, 1H), 3.39-3.62 (m, 2H), 3.30-3.01 (m, 6H), 1.68-1.61 (m, 2H), 1.09 (s, 3H), 1.03 (s, 3H); $^{13}$C NMR (100 MHz, DMSO-d$_6$): δ (ppm): 165.3, 156.6, 147.8, 134.5, 134.4, 132.0, 131.7, 131.6, 130.0, 129.0, 128.8, 125.6, 124.0, 112.8, 71.0, 65.4, 37.0, 29.9, 22.5, 17.1, 16.4; MS (ESI, m/z): 415.1724 [M+1]$^+$.

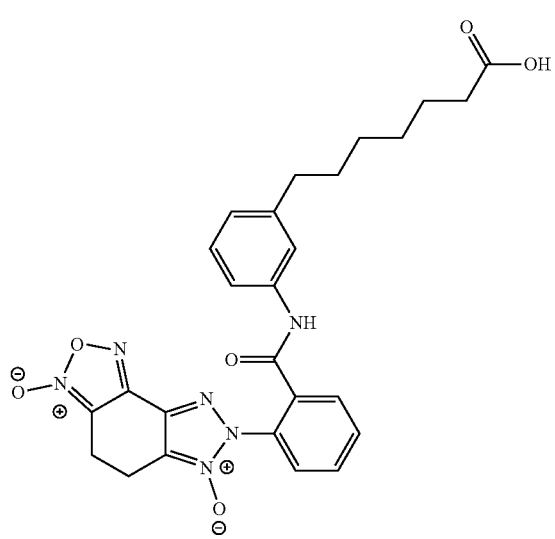

7-(2-((3-(6-carboxyhexyl)phenyl)carbamoyl)phenyl)-5,7-dihydro-4H-[1,2,3]triazolo[4',5':3,4]benzo[1,2-c][1,2,5]oxadiazole 3,6-dioxide (9w): Compound 9w was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and 7-(3-aminophenyl)heptanoic acid (140 mg, 0.63 mmol) to obtain 9w as a brown solid (269 mg, 82% yield). $^1$H NMR (400 MHz, DMSO-d$_6$): δ (ppm): 10.57 (bs, 1H), 7.94-7.72 (m, 4H), 7.46-7.40 (m, 2H), 7.22 (s, 1H), 6.92 (bs, 1H), 3.04 (s, 4H), 2.33-1.91 (m, 4H), 1.53-1.47 (m, 4H), 1.28-1.18 (m, 4H); $^{13}$C NMR (100 MHz, DMSO-d$_6$): δ (ppm): 172.9, 169.1, 147.8, 143.2, 139.3, 134.0, 132.3, 132.0, 131.6, 129.5, 128.9, 128.6, 125.9, 124.2, 120.3, 118.0, 112.8, 35.6, 31.2, 28.8, 25.5, 17.0, 16.4; MS (ESI, m/z): 519.1436 [M+1]$^+$.

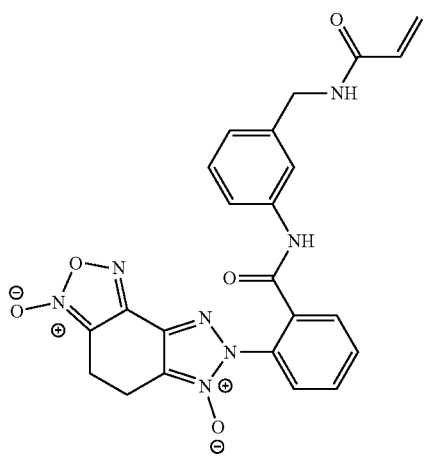

7-(2-((3-(acrylamidomethyl)phenyl)carbamoyl)phenyl)-5,7-dihydro-4H-[1,2,3]triazolo[4',5':3,4]benzo[1,2-c][1,2,5]oxadiazole 3,6-dioxide (9x): Compound 9x was prepared according to the method described in general procedure. Employing compound 8g (200 mg, 0.63 mmol) in 10 mL Dry DMF, HATU (289 mg, 0.76 mmol), DIPEA (0.34 mL 1.9 mmol) and N-(3-aminobenzyl)acrylamide (102 mg, 0.63 mmol) to obtain 9x as a pale yellow solid (241 mg, 83% yield). $^1$H NMR (400 MHz, DMSO-d$_6$): δ (ppm): 10.67 (bs, 1H), 8.62-8.59 (m, 1H), 7.93-7.91 (m, 4H), 7.55-7.52 (m, 2H), 7.26 (t, J=7.71 Hz, 1H), 6.99 (d, J=7.52 Hz, 1H), 6.31-6.24 (m, 1H), 6.12 (d, J=18.12 Hz, 1H), 5.62 (d, J=18.6 Hz, 1H), 4.31 (d, J=5.7 Hz, 2H), 3.07-3.01 (m, 4H); $^{13}$C NMR (100 MHz, DMSO-d$_6$): δ (ppm): 165.0, 164.2, 156.6, 147.8, 140.2, 139.5, 133.9, 132.3, 132.0, 131.6, 130.3, 129.6, 129.0, 128.5, 125.9, 123.2, 119.4, 112.9, 106.4, 42.6, 17.1, 16.4; MS (ESI, m/z): 474.1520 [M]$^+$.

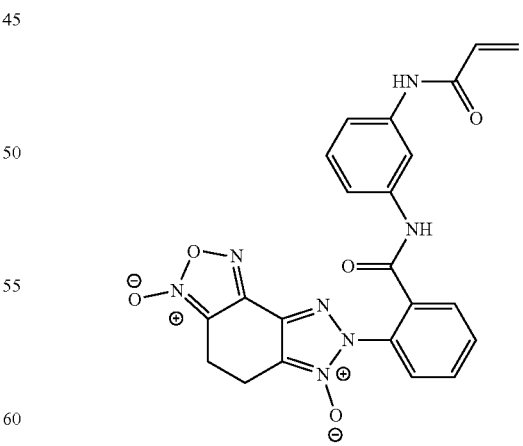

7-(2-((3-acrylamidophenyl)carbamoyl)phenyl)-5,7-dihydro-4H-[1,2,3]triazolo[4',5':3,4]benzo[1,2-c][1,2,5]oxadiazole 3,6-dioxide (9y): Compound 9y was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and N-(3-aminophenyl)acrylamide (102 mg, 0.63 mmol) to obtain 9y as a pale yellow solid (241 mg, 83% yield). $^1$H NMR (400 MHz, DMSO-d$_6$): δ (ppm): 10.67 (bs, 1H), 10.13 (bs, 1H), 8.05 (s, 1H), 7.93-7.70 (m, 4H), 7.42-7.20 (m, 3H), 6.46-6.38 (m, 1H), 6.23 (d, J=16.6 Hz, 1H), 5.73 (d, J=10.1 Hz, 1H), 3.03 (s, 4H); $^{13}$C NMR (100 MHz, DMSO-d$_6$): δ (ppm): 164.2, 163.5, 156.5, 147.7, 139.7, 139.6, 134.0, 132.3, 132.0, 131.6, 130.3, 129.6, 128.6, 127.3, 125.8, 124.3, 115.9, 115.3, 112.8, 111.7, 106.3, 19.6, 17.0, 16.4; MS (ESI, m/z): 460.1561 [M+1]$^+$.

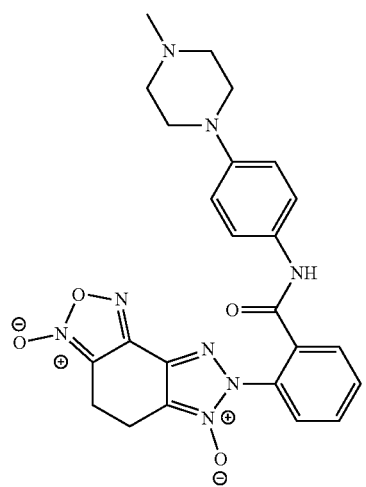

7-(2-((4-(4-methylpiperazin-1-yl)phenyl)carbamoyl)phenyl)-5,7-dihydro-4H-[1,2,3]triazolo[4',5':3,4]benzo[1,2-c][1,2,5]oxadiazole 3,6-dioxide (9z): Compound 9z was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and 4-(4-methylpiperazin-1-yl)aniline (121 mg, 0.63 mmol) to obtain 9z as Yellow solid (254 mg, 82% yield). $^1$H NMR (400 MHz, DMSO-d$_6$): δ (ppm): 10.41 (bs, 1H), 7.92-7.90 (m, 1H), 7.83-7.75 (m, 3H), 7.48-7.43 (m, 2H), 6.92-6.85 (m, 2H), 3.09-3.01 (m, 7H), 2.46 (t, J=4.6 Hz, 4H), 2.23 (s, 3H); $^{13}$C NMR (100 MHz, DMSO-d$_6$): δ (ppm): 163.6, 148.0, 147.8, 134.2, 132.2, 131.7, 131.6, 131.3, 129.5, 128.6, 125.8, 121.6, 115.9, 112.8, 54.9, 48.8, 46.1, 17.0, 16.4; MS (ESI, m/z): 489.1237 [M+1]$^+$.

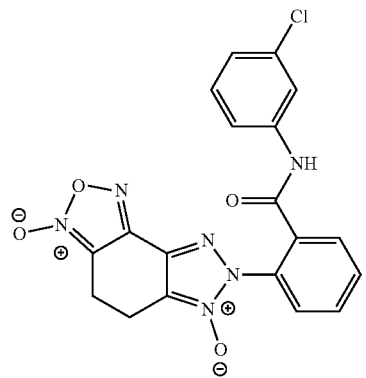

7-(2-((3-chlorophenyl)carbamoyl)phenyl)-5,7-dihydro-4H-[1,2,3]triazolo[4',5':3,4]benzo[1,2-c][1,2,5]oxadiazole 3,6-dioxide (9aa): Compound 9aa was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and 3-chloroaniline (80 mg, 0.63 mmol) to obtain 9aa as yellow solid (231 mg, 86% yield). $^1$H NMR (400 MHz, DMSO-d$_6$): δ (ppm): 10.84 (bs, 1H), 7.95-7.83 (m, 5H), 7.53-7.15 (m, 3H), 3.04 (s, 4H); $^{13}$C NMR (100 MHz, DMSO-d$_6$): δ (ppm): 164.5, 147.8, 140.9, 133.4, 132.4, 131.6, 130.8, 129.5, 128.5, 126.4, 126.0, 125.6, 124.7, 123.9, 119.8, 118.8, 116.2, 112.9, 17.0, 16.4; MS (ESI, m/z): 425.0762 [M+1]$^+$.

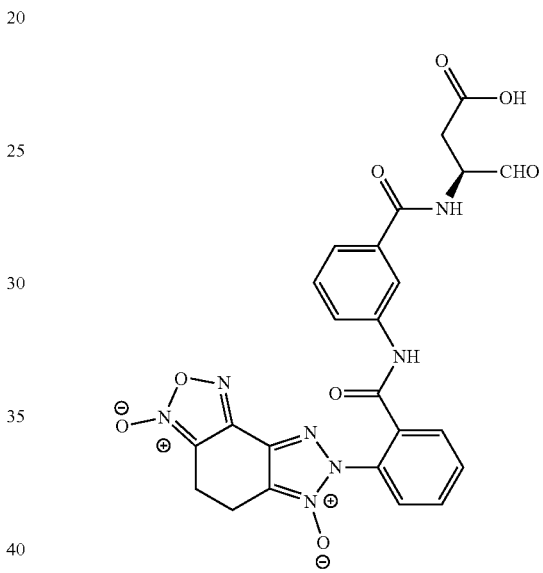

(S)-7-(2-((3-((1-carboxy-3-oxopropan-2-yl)carbamoyl)phenyl)carbamoyl)phenyl)-5,7-dihydro-4H-[1,2,3]triazolo[4',5':3,4]benzo[1,2-c][1,2,5]oxadiazole 3,6-dioxide (9ab): Compound 9ab was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and tertbutyl (S)-3-(3-aminobenzamido)-4,4-dimethoxybutanoate (214 mg, 0.63 mmol) followed by hydrolysis with orthophosphoric acid (85%) solution to obtain 9ab as a pale yellow solid (283 mg, 84% yield). $^1$H NMR (400 MHz, DMSO-d$_6$): δ (ppm): 10.82 (bs, 1H), 8.93 (bs, 1H), 8.14-8.10 (m, 1H), 7.98-7.95 (m, 1H), 7.95-7.86 (m, 4H), 7.59 (d, J=7.7 Hz, 1H), 7.43 (t, J=7.8 Hz, 1H), 4.51-4.32 (m, 1H), 3.34-3.17 (m, 2H), 3.11-2.97 (m, 4H); $^{13}$C NMR (100 MHz, DMSO-d$_6$): δ (ppm): 166.8, 164.3, 147.8, 139.5, 133.6, 132.3, 132.2, 131.6, 129.5, 129.0, 128.6, 125.9, 124.3, 123.6, 122.9, 120.0, 112.9, 60.2, 21.2, 17.0, 16.4, 14.5; MS (ESI, m/z): 534.1366 [M+1]$^+$.

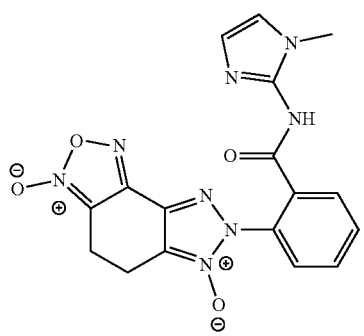

7-(2-((1-methyl-1H-imidazol-2-yl)carbamoyl)phenyl)-5,7-dihydro-4H-[1,2,3]triazolo[4',5':3,4]benzo[1,2-c][1,2,5]oxadiazole 3,6-dioxide (9ac): Compound 9ac was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and 1-methyl-1H-imidazol-2-amine (61 mg, 0.63 mmol) to obtain 9ac as yellow solid (205 mg, 82% yield). MS (ESI, m/z): 395 [M+1]⁺.

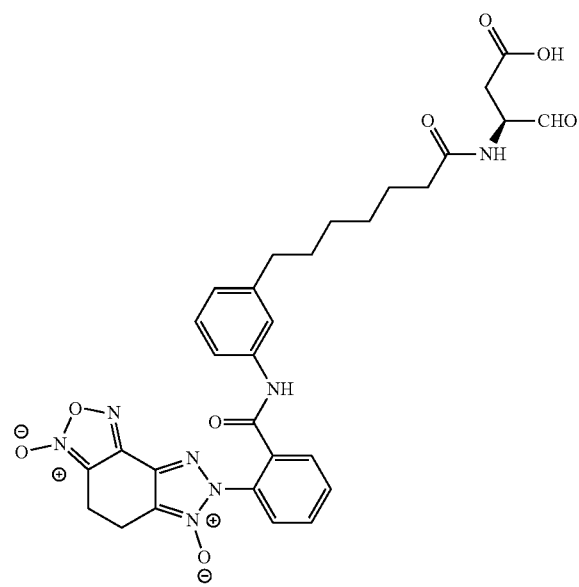

(S)-7-(2-((3-(7-((1-carboxy-3-oxopropan-2-yl)amino)-7-oxoheptyl)phenyl)carbamoyl)phenyl)-5,7-dihydro-4H-[1,2,3]triazolo[4',5':3,4]benzo[1,2-c][1,2,5]oxadiazole 3,6-dioxide (9ad): Compound 9ad was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and tert-butyl (S)-3-(7-(3-aminophenyl)heptanamido)-4,4-dimethoxybutanoate (267 mg, 0.63 mmol) followed by deprotection with orthophosphoric acid (85%) solution to obtain 9ad as a pale yellow solid (230 mg, 84% yield). ¹H NMR (400 MHz, CD₃OD): δ (ppm): 8.01-7.92 (s, 1H), 7.85-7.72 (m, 3H), 7.40 (s, 1H), 7.35 (d, J=8.8 Hz, 1H), 7.22 (t, J=7.7 Hz, 1H), 6.93 (d, J=7.6 Hz, 1H), 4.57 (dd, J=12.6, 3.79 Hz, 1H), 4.34-4.23 (m, 1H), 3.16-3.05 (m, 4H), 2.70-2.41 (m, 4H), 2.24-2.15 (m, 2H), 1.68-1.54 (m, 4H), 1.42-1.30 (m, 4H); ¹³C NMR (100 MHz, DMSO-d₆): δ (ppm): 173.0, 164.1, 147.8, 143.2, 139.4, 134.0, 132.3, 132.0, 131.6, 129.5, 128.9, 128.6, 125.9, 124.2, 120.3, 118.0, 112.9, 35.6, 35.4, 33.6, 31.2, 28.8, 25.5, 17.1, 16.4; MS (ESI, m/z): 618.2310 [M+1]⁺.

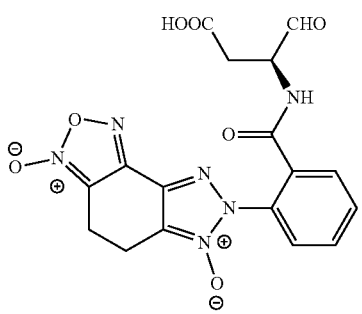

(S)-7-(2-((1-carboxy-3-oxopropan-2-yl)carbamoyl)phenyl)-5,7-dihydro-4H-[1,2,3]triazolo[4',5':3,4]benzo[1,2-c][1,2,5]oxadiazole 3,6-dioxide (9ae): Compound 9ae was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and tert-butyl (S)-3-amino-4,4-dimethoxybutanoate (139 mg, 0.63 mmol) followed by deprotection with Orthophosphoric acid (85%) solution to obtain 9ae as a pale yellow solid (230 mg, 84% yield). ¹H NMR (400 MHz, DMSO-d₆): δ (ppm): 9.04-9.01 (bs, 1H), 7.86-7.68 (m, 4H), 4.24-4.13 (m, 1H), 3.17-2.99 (m, 4H), 2.91-2.81 (m, 2H), 2.57-2.53 (m, 1H); ¹³C NMR (100 MHz, DMSO-d₆): δ (ppm): 165.9, 147.8, 133.2, 132.2, 132.1, 131.7, 131.4, 129.3, 128.4, 126.0, 112.9, 60.2, 21.2, 17.0, 16.4; MS (ESI, m/z): 415.0997 [M+1]⁺.

7-(2-(phenylcarbamoyl)phenyl)-5,7-dihydro-4H-[1,2,3]triazolo[4',5':3,4]benzo[1,2-c][1,2,5]oxadiazole 3,6-dioxide (9af): Compound 9af was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and aniline (59 mg, 0.63 mmol) to obtain 9af as a pale yellow solid (217 mg, 88% yield). ¹H NMR (400 MHz, DMSO-d₆): δ (ppm): 10.64 (bs, 1H), 7.98-7.90 (m, 1H), 7.85-7.77 (m, 3H), 7.63 (d, J=7.8 Hz, 2H), 7.32 (t, J=7.8 Hz, 2H), 7.09 (t, J=7.3 Hz, 1H), 3.09-3.01 (m, 4H); ¹³C NMR (100 MHz, DMSO-d₆): δ (ppm): 164.2, 147.8, 139.4, 133.9, 132.3, 132.1, 131.6, 129.5, 129.0, 128.6, 125.9, 124.2, 120.5, 112.9, 17.0, 16.4; MS (ESI, m/z): 391.1149 [M+1]⁺.

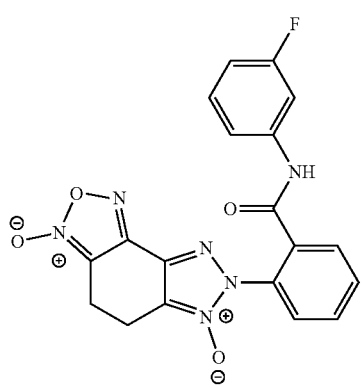

7-(2-((3-fluorophenyl)carbamoyl)phenyl)-5,7-dihydro-4H-[1,2,3]triazolo[4',5':3,4]benzo[1,2-c][1,2,5]oxadiazole 3,6-dioxide (9ag): Compound 9ag was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and 6-methoxybenzo[d]thiazol-2-amine (70 mg, 0.63 mmol) to obtain 9ag as a pale yellow solid (225 mg, 87% yield). $^1$H NMR (400 MHz, DMSO-d$_6$): δ (ppm): 1087 (bs, 1H), 7.96-7.91 (m, 1H), 7.87-7.78 (m, 3H), 7.59 (d, J=11.5 Hz, 1H), 7.42-7.33 (m, 2H), 6.92 (t, J=7.6 Hz, 1H), 3.08-3.02 (m, 4H); $^{13}$C NMR (100 MHz, DMSO-d$_6$): δ (ppm): 164.5, 163.6, 161.2, 147.8, 141.2, 133.4, 132.4, 132.3, 131.6, 130.8, 129.5, 128.6, 1260, 116.2, 112.9, 110.7, 107.3, 17.0, 16.4; MS (ESI, m/z): 409.1055 [M+1]$^+$.

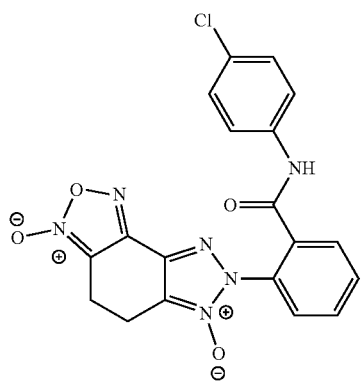

7-(2-((4-chlorophenyl)carbamoyl)phenyl)-5,7-dihydro-4H-[1,2,3]triazolo[4',5':3,4]benzo[1,2-c][1,2,5]oxadiazole 3,6-dioxide (9ah): Compound 9ah was prepared according to the method described in general procedure. Employing compound 8g (200 mg, 0.63 mmol) in 10 mL Dry DMF, HATU (289 mg, 0.76 mmol), DIPEA (0.34 ML1.9 mmol) and 4-chloro aniline (80 mg, 0.63 mmol) to obtain 9ah as a brown solid (231 mg, 86% yield). $^1$H NMR (400 MHz, DMSO-d$_6$): δ (ppm): 10.79 (bs, 1H), 7.96-7.94 (m, 1H), 7.86-7.78 (m, 3H), 7.67 (d, J=8.6 Hz, 2H), 7.38 (d, J=8.6 Hz, 2H), 3.09-3.01 (m, 4H); $^{13}$C NMR (100 MHz, DMSO-d$_6$): δ (ppm): 164.3, 156.6, 147.8, 138.4, 133.6, 132.3, 132.2, 131.6, 129.5, 129.0, 128.5, 127.8, 125.9, 122.0, 112.9, 17.0, 16.4; MS (ESI, m/z): 425.0760 [M+1]$^+$.

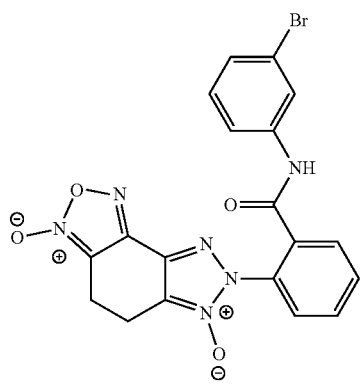

7-(2-((3-bromophenyl)carbamoyl)phenyl)-5,7-dihydro-4H-[1,2,3]triazolo[4',5':3,4]benzo[1,2-c][1,2,5]oxadiazole 3,6-dioxide (9ai): Compound 9ai was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and 3-bromo aniline (109 mg, 0.63 mmol) to obtain 9ai as a pale yellow solid (259 mg, 87% yield). $^1$H NMR (400 MHz, DMSO-d$_6$): δ (ppm): 10.83 (bs, 1H), 7.98-7.90 (m, 2H), 7.96-7.73 (m, 3H), 7.62-7.50 (m, 1H), 7.33-7.28 (m, 2H), 3.05 (bs, 4H); MS (ESI, m/z): 469.0254[M+1]$^+$.

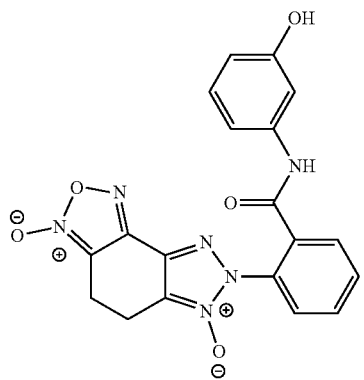

7-(2-((3-hydroxyphenyl)carbamoyl)phenyl)-5,7-dihydro-4H-[1,2,3]triazolo[4',5':3,4]benzo[1,2-c][1,2,5]oxadiazole 3,6-dioxide (9aj): Compound 9aj was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and 3-hydroxy aniline (69 mg, 0.63 mmol) to obtain 9aj as a brown solid (276 mg, 88% yield). $^1$H NMR (400 MHz, DMSO-d$_6$): δ (ppm): 10.52 (bs, 1H), 9.37 (bs, 1H), 7.95-7.89 (m, 1H), 7.84-7.76 (m, 3H), 7.21-7.18 (m, 1H), 7.10-7.01 (m, 2H), 6.50-6.47 (m, 1H), 3.09-3.01 (m, 4H); $^{11}$C NMR (100 MHz, DMSO-d$_6$): δ (ppm): 164.0, 157.9, 147.8, 140.5, 134.1, 132.2, 132.0, 131.6, 129.7, 128.6, 125.8, 124.3, 122.8, 111.3, 111.2, 107.6, 17.0, 16.4; MS (ESI, m/z): 407.1247 [M+1]$^+$.

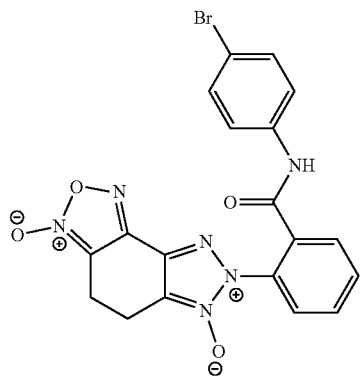

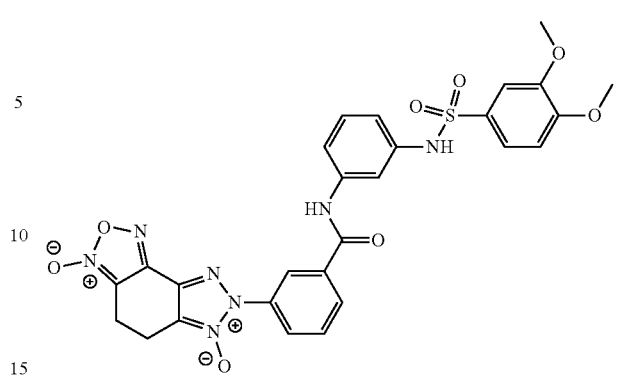

7-(2-((4-bromophenyl)carbamoyl)phenyl)-5,7-dihydro-4H-[1,2,3]triazolo[4',5':3,4]benzo[1,2-c][1,2,5]oxadiazole 3,6-dioxide (9ak): Compound 9ak was prepared according to the method described in general procedure. Employing compound 8g (200 mg, 0.63 mmol) in 10 mL Dry DMF, HATU (289 mg, 0.76 mmol), DIPEA (0.34 mL1.9 mmol) and 4-bromoaniline (109 mg, 0.63 mmol) to obtain 9ak as a pale yellow solid (254 mg, 87% yield). $^1$H NMR (400 MHz, DMSO-$d_6$): δ (ppm): 10.78 (bs, 1H), 7.98-7.92 (m, 1H), 7.85-7.75 (m, 3H), 7.61 (d, J=8.7 Hz, 2H), 7.50 (d, J=8.7 Hz, 2H), 3.09-3.01 (n, 4H); 1-C NMR (100 MHz, DMSO-$d_6$): δ (ppm): 164.3, 156.6, 147.9, 138.8, 133.5, 132.3, 132.2, 131.9, 131.6, 129.5, 128.5, 125.9, 122.3, 115.9, 112.8, 17.0, 16.4; MS (ESI, m/z): 469.0254 [M+1]$^+$.

7-(3-((3-((3,4-dimethoxyphenyl)sulfonamido)phenyl)carbamoyl)phenyl)-5,7-dihydro-4H-[1,2,3]triazolo[4',5':3,4]benzo[1,2-c][1,2,5]oxadiazole 3,6-dioxide (10b): Compound 10b was prepared according to the method described in general procedure. Employing compound 8o (200 mg, 0.63 mmol) in 10 mL Dry DMF, HATU (289 mg, 0.76 mmol), DIPEA (0.34 mL1.9 mmol) and N-(3-aminophenyl)-3,4-dimethoxybenzenesulfonamide (0.63 mmol) to obtain 10b as a brown solid (326 mg, 85% yield). $^1$H NMR (400 MHz, DMSO-$d_6$): δ (ppm): 10.52 (bs, 1H), 10.16 (bs, 1H), 8.43 (s, 1H), 8.16 (d, J=7.6 Hz, 2H), 7.83-7.77 (m, 2H), 7.44-7.34 (m, 3H), 7.20 (t, J=8.0 Hz, 1H), 7.06 (d, J=8.04 Hz, 1H), 6.84 (d, J=7.7 Hz, 1H), 3.79 (s, 3H), 3.76 (s, 3H), 3.10 (s, 4H); MS (ESI, m/z): 606.5816 [M+1]$^+$.

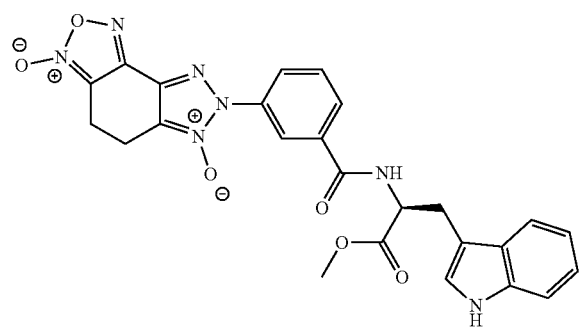 [SMILES: COC(=O)[C@H](Cc1c[nH]c2ccccc12)NC(=O)c1cccc(-n2nc3c([n+]2[O-])CCc2c-3no[n+]2[O-])c1]

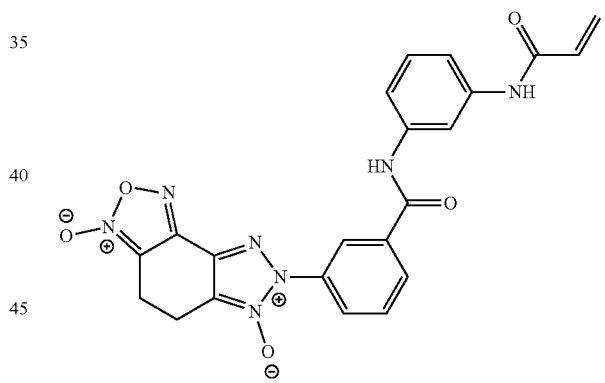

(S)-7-(3-((3-(1H-indol-3-yl)-1-methoxy-1-oxopropan-2-yl)carbamoyl)phenyl)-5,7-dihydro-4H-[1,2,3]triazolo[4',5':3,4]benzo[1,2-c][1,2,5]oxadiazole 3,6-dioxide (10a): Compound 10a was prepared according to the method described in general procedure. Employing compound 8o (200 mg, 0.63 mmol) in 10 mL Dry DM, HATU (289 mg, 0.76 mmol), DIPEA (0.34 mL1.9 mmol) and methyl D-tryptophanate (0.63 mmol) to obtain 10a as a pale yellow solid (280 mg, 86% yield). $^1$H NMR (400 MHz, DMSO-$d_6$): δ (ppm): 10.84 (bs, 1H), 9.14 (d, J=7.5 Hz, 1H), 8.36 (t, J=1.8 Hz, 1H), 8.13-8.10 (m, 1H), 8.07-8.04 (m, 1H), 7.95 (s, 1H), 7.76 (t, J=8.0 Hz, 1H), 7.57 (d, J=7.8 Hz, 1H), 7.33 (d, J=8.0 Hz, 1H), 7.08-6.97 (m, 2H), 4.77-4.72 (m, 1H), 3.65 (s, 3H), 3.35-3.22 (m, 2H), 3.09 (s, 4H); MS (ESI, m/z): 516.1626 [M+1]$^+$.

7-(3-((3-acrylamidophenyl)carbamoyl)phenyl)-5,7-dihydro-4H-[1,2,3]triazolo[4',5':3,4]benzo[1,2-c][1,2,5]oxadiazole 3,6-dioxide (10c): Compound 10c was prepared according to the method described in general procedure. Employing compound 8o (200 mg, 0.63 mmol) in 10 mL Dry DMF, HATU (289 mg, 0.76 mmol), DIPEA (0.34 mL1.9 mmol) and N-(3-aminophenyl)acrylamide (102 mg, 0.63 mmol) to obtain 10c as a pale yellow solid (241 mg, 83% yield). $^1$H NMR (400 MHz, DMSO-$d_6$): δ (ppm): 10.52 (bs, 1H), 10.20 (bs, 1H), 8.46 (s, 1H), 8.22-8.08 (m, 3H), 7.81 (t, J=7.9 Hz, 1H), 7.48-7.43 (m, 2H), 7.30 (t. J=8.0 Hz, 1H), 6.50-6.43 (m, 1H), 6.28 (dd, J=18.1, 1.7 Hz, 1H), 5.75 (dd, J=11.2, 1.7 Hz, 1H), 3.10 (s, 4H); $^{13}$C NMR (100 MHz, DMSO-$d_6$): δ (ppm): 164.5, 163.6, 156.8, 147.8, 139.7, 139.6, 136.5, 134.6, 132.6, 132.3, 130.0, 129.5, 129.3, 127.3, 127.2, 126.9, 125.6, 123.4, 116.2, 115.6, 112.9, 112.1, 17.1, 16.6; MS (ESI, m/z): 460.1364 [M+1]$^+$.

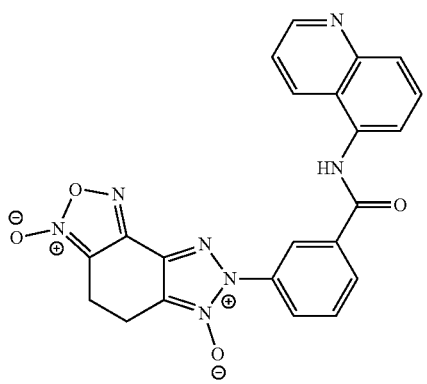

7-(3-(quinolin-5-ylcarbamoyl)phenyl)-5,7-dihydro-4H-[1,2,3]triazolo[4',5':3,4]benzo[1,2-c][1,2,5]oxadiazole 3,6-dioxide (10d): Compound 10d was prepared according to the method described in general procedure. Employing compound 80 (200 mg, 0.63 mmol) in 10 mL Dry DMF, HATU (289 mg, 0.76 mmol), DIPEA (0.34 mL1.9 mmol) and quinolin-5-amine (144 mg, 0.63 mmol) to obtain 10d as a brown solid (238 mg, 85% yield). $^1$H NMR (400 MHz, DMSO-$d_6$): δ (ppm): 1081 (bs, 1H), 8.95 (s, 1H), 8.69-8.15 (m, 4H), 8.15-7.56 (m, 4H), 3.11 (s, 4H); $^{13}$C NMR (100 MHz, DMSO-$d_6$): δ (ppm): 165.3, 151.0, 148.6, 147.8, 1359, 134.7, 132.7, 132.0, 130.2, 129.6, 129.4, 127.8, 127.2, 124.6, 124.3, 123.5, 121.6, 112.9, 17.1, 16.6; MS (ESI, m/z): 442.1257 [M+1]$^+$.

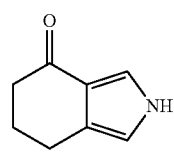

2,5,6,7-tetrahydro-4H-isoindol-4-one (11): To a stirred solution of cyclohexenone (0.026 moles) in 50 ml. of Dry THF was added p-toluenesulfonylmethyl isocyanide (0.026 mol) and followed by t-BuOK (0.052 mol) at 0° C. Continued the stirring at 25° C. for about 1 h, 50 mL of Ice cold water was added and extracted with Ethyl acetate (2×50 ml). The combined organic layers were washed with brine, dried over Na2SO4, filtered, and concentrated to give a crude product, which was purified by column chromatography (silica gel 120-200 mesh), eluting with cyclohexane/EtOAc (from 100:0 to 40:60) to afford with high purity compound 11 as a colourless solid. MS (EI, m/z): 136 [M]$^+$.

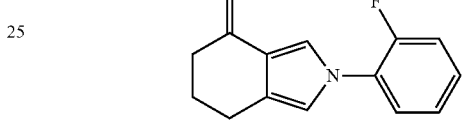

2-(2-fluorophenyl)-2,5,6,7-tetrahydro-4H-isoindol-4-one (12): To a solution of 11 (3.5 g, 0.025 mol) in N-methyl-2-pyrrolidone (NMP) (40 mL) K$_2$CO$_3$ (3.57 g, 0.025 mol) was added, followed by the addition of CuBr (7.43 g, 0.04 mol) and 2-fluoroiodobenzene (3.1 mL, 0.025 mol). The reaction was heated under reflux for 24 h. After the addition 5% HCl Scheme-III. Synthesis of compound 15

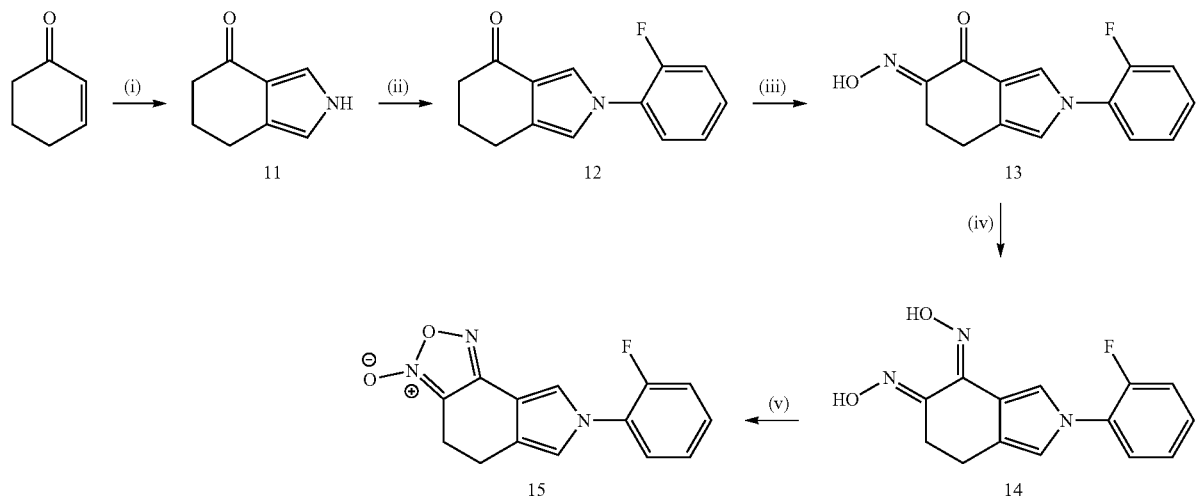

Reagents and conditions: (i) p-toluenesulfonylmethyl isocyanide (TOSMIC), t-BuOK and Dry THF, 25° C., 1 h (85%); (ii) N-methyl-2-pyrrolidone (NMP), K$_2$CO$_3$, 2-Fluoroiodobenzene and Copper (I) bromide, 205° C., 24 h (40%); (iii) Isoamyl nitrite, t-BuOK t-butanol 25° C. for 30 min (60%); (iv) NH$_2$OH.HCl, MeOH, 70° C. 1 h (80%); (v) NaOBr aq Sol, H$_2$O, 30 min (85%).

(50 mL) and ethyl acetate (50 mL) the mixture was filtered through Celite and then stirred with brine. The organic phase was separated, dried (Na$_2$SO$_4$) and evaporated under reduced pressure. Column chromatography (silica gel 120-200 mesh), eluting with cyclohexane/EtOAc (from 100:0 to 40:60) to afford with high purity compound 12 as a pale yellow solid. MS (EI, m/z): 229 [M]$^+$.

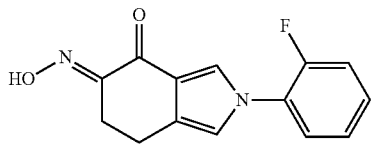 [SMILES: O=C1/C(=N/O)CCc2cn(-c3ccccc3F)cc21]

(E)-2-(2-fluorophenyl)-5-(hydroxyimino)-2,5,6,7-tetrahydro-4H-isoindol-4-one (13): To a stirred solution of 12 (3 mmol) in 10 mL of t-BuOH was added t-BuOK (5.1 mmol) followed by Isoamyl nitrite (1 mL, 7.5 mmol) at 0° C. Continued the stirring at 25° C. for about 30 min, 20 mL of Ice cold water was added and extracted with Ethyl acetate (2×50 ml). The combined organic layers were washed with brine, dried over Na2SO4, filtered, and concentrated to give a crude product, which was purified by column chromatography (silica gel 120-200 mesh), eluting with cyclohexane/EtOAc (from 100:0 to 40:60) to afford with high purity compound 13 as a yellow solid. MS (EI, m/z): 258 [M]$^+$.

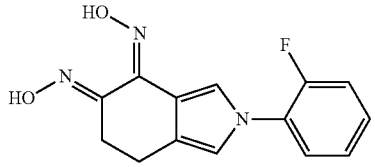 [SMILES: O/N=C1\C(=N\O)CCc2cn(-c3ccccc3F)cc21]

2-(2-fluorophenyl)-6,7-dihydro-2H-isoindole-4,5-dione dioxime (14): To a stirred solution of 13 (1.5 mmol) in 10 mL of 50% EtOH solution was added Na$_2$CO$_3$ (0.93 mmol) followed by NH$_2$OH. HCl (1.93 mmol) at 0° C. Continued the stirring at 25° C. for about 3 h, the reaction mixture was concentrated and to the obtained crude 20 mL of Ice cold water was added and extracted with Ethyl acetate (2×50 ml). The combined organic layers were washed with brine, dried over Na2SO4, filtered, and concentrated to give a crude product, which was purified by column chromatography (silica gel 120-200 mesh), eluting with cyclohexane/EtOAc (from 100:0 to 40:60) to afford with high purity compound 14 as a yellow solid. MS (EI, m/z): 273 [M]$^+$.

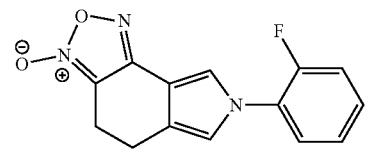 [SMILES: [O-][n+]1onc2c1CCc1cn(-c3ccccc3F)cc1-2]

7-(2-fluorophenyl)-5,7-dihydro-4H-[1,2,5]oxadiazolo[3,4-e]isoindole 3-oxide (15): To a solution of 14 (0.73 mmol) in 2 mL of 10% NaOH was added at reaction temperature 5-10° C. a solution of sodium hypobromite prepared from 30 mg. of NaOH in 2 mL of water and 0.2 mL of bromine. The reaction mixture was stirred 1 h at 25° C. and 0.5 mL of con. HCl was added slowly drop wise. The precipitate obtained was filtered on Buckner funnel and washed with (2 mL×2) H$_2$O and dried to obtain compound-15 as a pale yellow solid (160 mg. 82% yield). $^1$H NMR (400 MHz, CDCl$_3$): δ (ppm): 7.54 (s, 1H), 7.45-7.26 (m, 4H), 6.95 (s, 1H), 3.01-2.90 (m, 4H); $^{13}$C NMR (100 MHz, DMSO-d$_6$): δ (ppm): 156.1, 153.6, 151.2, 129.3, 127.9, 127.8, 121.9, 120.0, 119.9, 119.9, 199.2, 117.6, 117.4, 112.6, 109.8, 19.1, 18.5; MS (ESI, m/z): 272.0830 [M+1]$^+$.

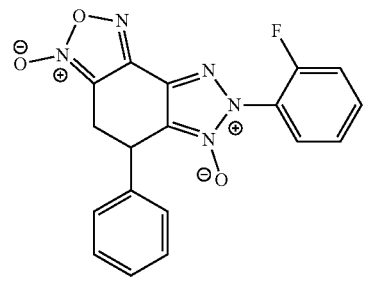

7-(2-fluorophenyl)-5-phenyl-5,7-dihydro-4H-[1,2,3]triazolo[4',5':3,4]benzo[1,2-c][1,2,5]oxadiazole 3,6-dioxide (16): Compound 16 was prepared by a sequence of steps described in Scheme I by employing 4-phenylcyclohexan-1-one as a starting material. MS (ESI, m/z): 366.0997 [M+1]$^+$.

The present invention provides for the following embodiments, the numbering of which is not to be construed as designating levels of importance:

Embodiment 1 relates to a compound of the general formula (I):

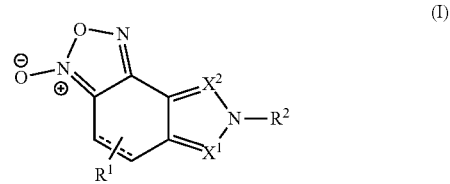

(I)

or a pharmaceutically acceptable salt, polymorph, prodrug, solvate or clathrate thereof, wherein:

the dashed line represents a single or a double bond;

R$^1$ is H or aryl;

R$^2$ is H or aryl; and

X$^1$ and X$^2$ are each, independently, N, N$^+$—O$^-$ or CR$^3$, wherein R$^3$ is H or alkyl and only one of X$^1$ and X$^2$ can be N$^+$—O$^-$;

with the proviso that the compound of the formula (I) is not the compound of the formula:

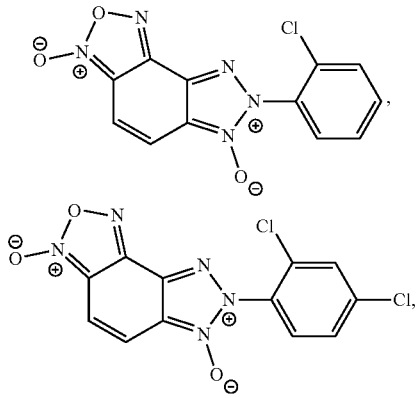

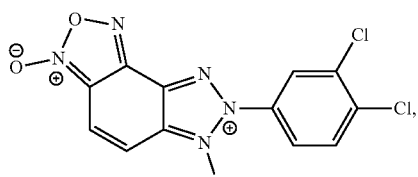

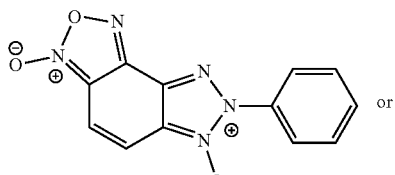 or

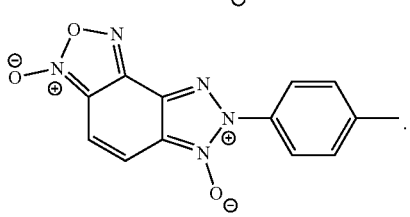

Embodiment 2 relates to the compound of Embodiment 1, wherein the compound of formula (I) is a compound of the general formula (Ia) or (Ib):

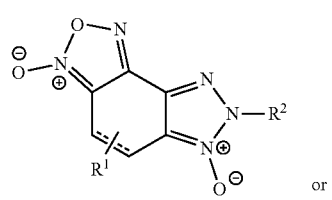

(Ia)

or

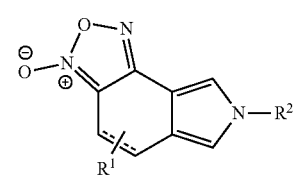

(Ib)

or a pharmaceutically acceptable salt, polymorph, prodrug, solvate or clathrate thereof, wherein the dashed line in the compounds of formula (Ia) and (Ib) represents a single or a double bond and $R^1$ and $R^2$ are defined as in Embodiment 1;

with the proviso that the compound of the formula (Ia) is not the compound of the formula:

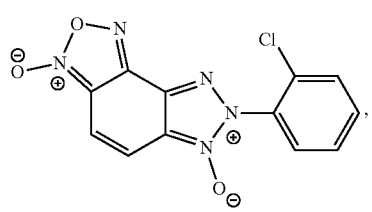

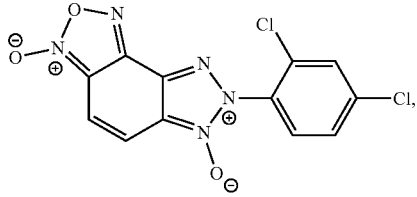

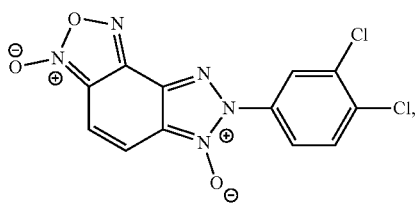

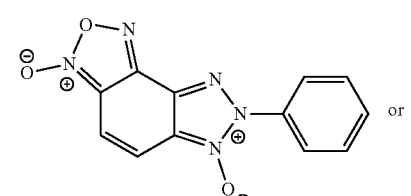 or

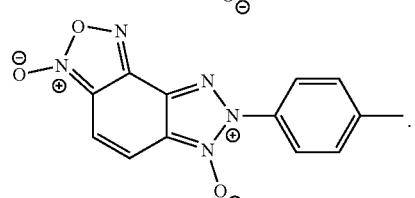

Embodiment 3 relates to the compound of Embodiment 1 or 2, wherein the formula (I) is a compound of the formula (Ic):

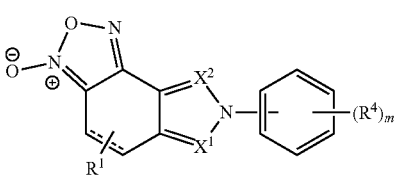

(Ic)

or a pharmaceutically acceptable salt, polymorph, prodrug, solvate or clathrate thereof, wherein the dashed line represents a single or a double bond; $X^1$, $X^2$, and $R^1$ are defined as in claim 1; m is an integer from 1 to 3; and each $R^4$ is, independently, H, halo, alkyl, alkoxy, nitro, $N(R^5)_2$, $COR^6$, or haloalkyl, wherein each $R^5$ is, independently, H, $S(O)_nR^7$ or acyl, wherein $R^7$ can be alkyl or aryl and n is an integer from 1 to 2, and $R^6$ is H, alkyl, alkenyl, alkynyl, aryl, heteroaryl or $N(R^8)_2$, wherein each $R^8$ is, independently, H, alkyl or aryl; or, two adjacent $R^4$ groups, together with the atoms to which they are attached, can form an aryl or a heteroaryl group;

with the proviso that the compound of the formula (Ic) is not the compound of the formula:

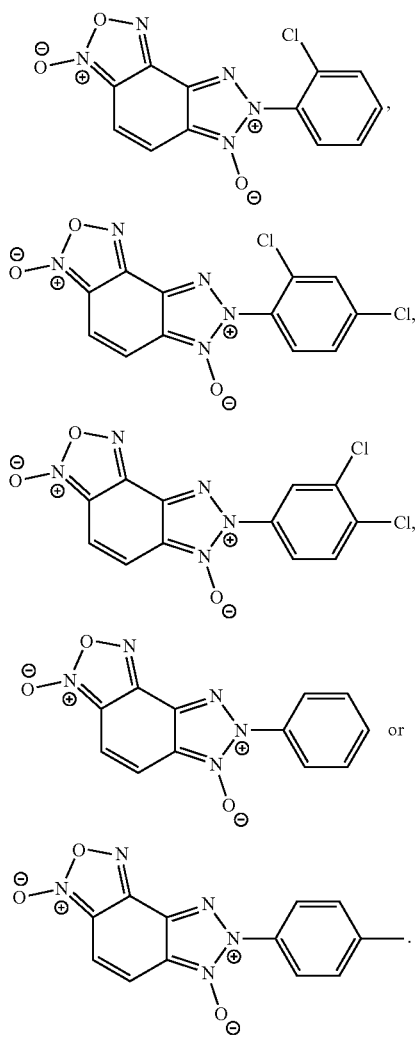

Embodiment 4 relates to the compound of Embodiments 1-3, wherein the compound of the formula (I) is a compound of the formula (Id):

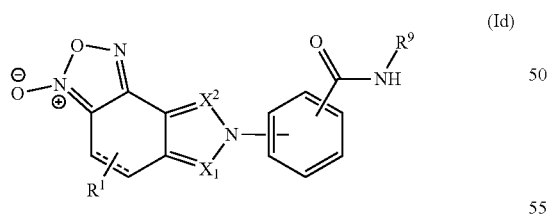

(Id)

or a pharmaceutically acceptable salt, polymorph, prodrug, solvate or clathrate thereof, wherein the dashed line represents a single or a double bond; $X^1$, $X^2$, and $R^1$ are defined as in Embodiment 1; m is an integer from 1 to 3; and $R^9$ is H, alkyl, aryl, alkenyl, alkynyl, arylalkyl or heteroarylalkyl.

Embodiment 5 relates to the compound of Embodiments 1-4, wherein the compound of the formula (I) is a compound of the formula (Ie):

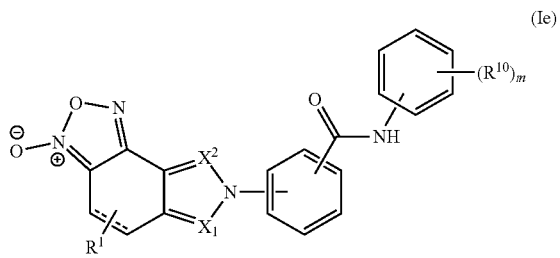

(Ie)

or a pharmaceutically acceptable salt, polymorph, prodrug, solvate or clathrate thereof, wherein the dashed line represents a single or a double bond; $X^1$, $X^2$, and $R^4$ are defined as in Embodiment 1; m is an integer from 1 to 3; and $R^{10}$ is H, halo, alkyl, OH, alkoxy, aryl, alkenyl, alkynyl, arylalkyl, heteroarylalkyl, heterocyclyl, $N(R^5)_2$ or $COR^6$, wherein $R^5$ and $R^6$ are defined herein; or, two adjacent $R^{10}$ groups, together with the atoms to which they are attached, can form a cycloalkyl, aryl or a heteroaryl group.

Embodiment 6 relates to the compound of Embodiments 1-5, wherein the compound of the formula (I) is a compound of the formula (If):

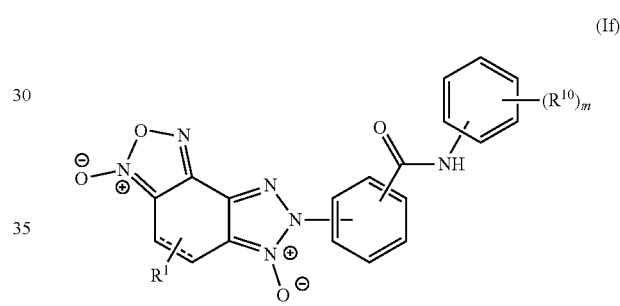

(If)

or a pharmaceutically acceptable salt, polymorph, prodrug, solvate or clathrate thereof, wherein the dashed line represents a single or a double bond and $R^1$, $R^{10}$, and m are defined as in Embodiment 5.

Embodiment 7 relates to the compound of Embodiments 1-6, wherein the compound of the formula (I) is a compound of the formula:

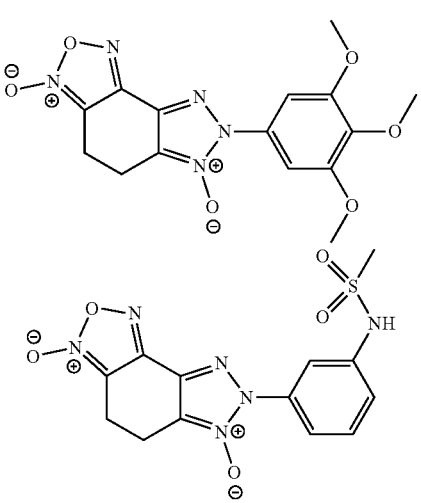

73
-continued
74
-continued
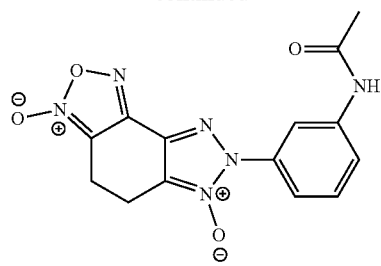
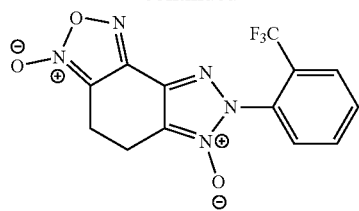
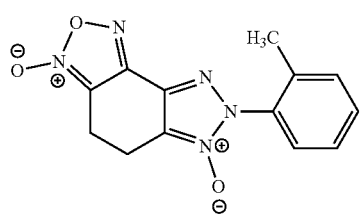
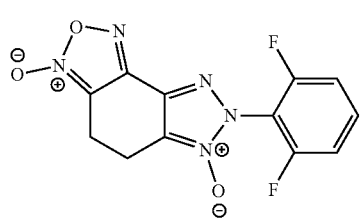
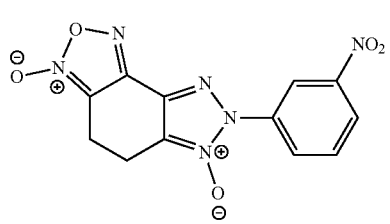
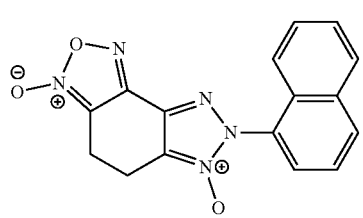
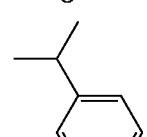
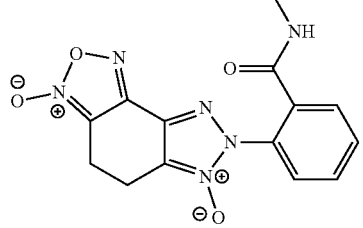

75
-continued
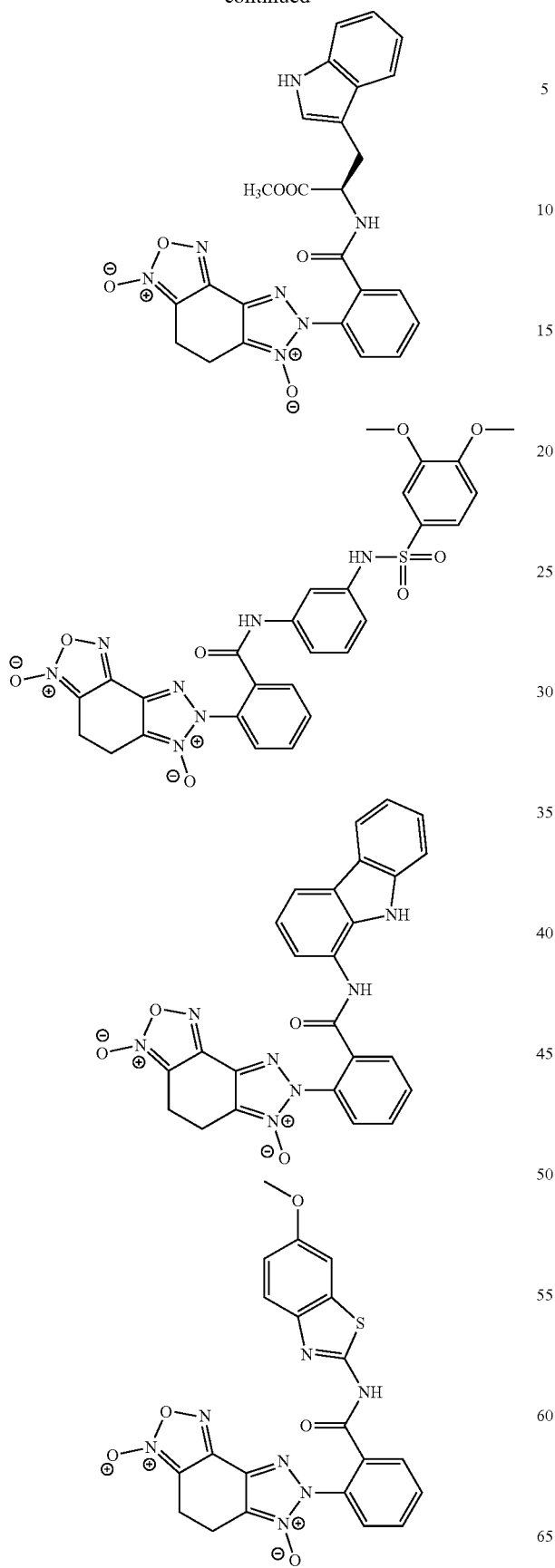
76
-continued
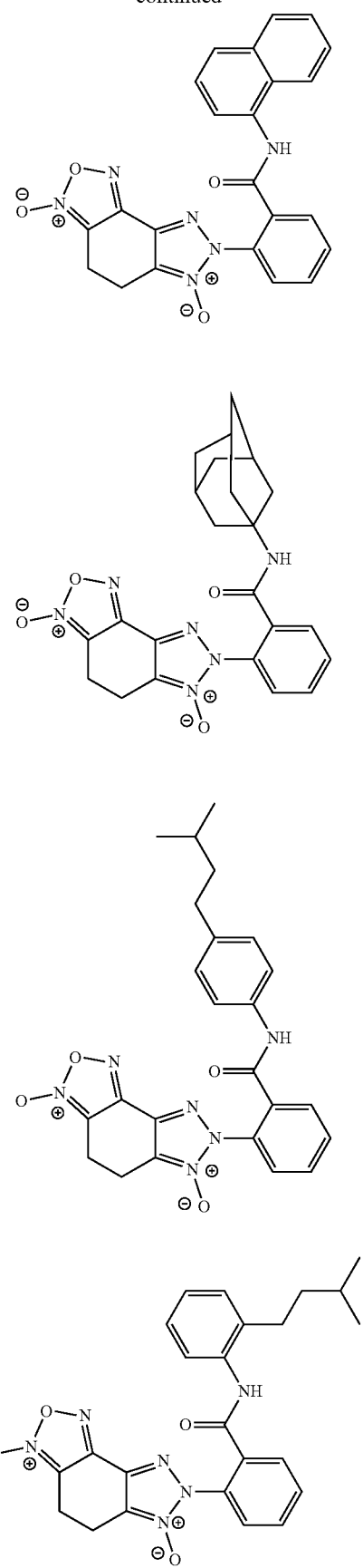

77
-continued
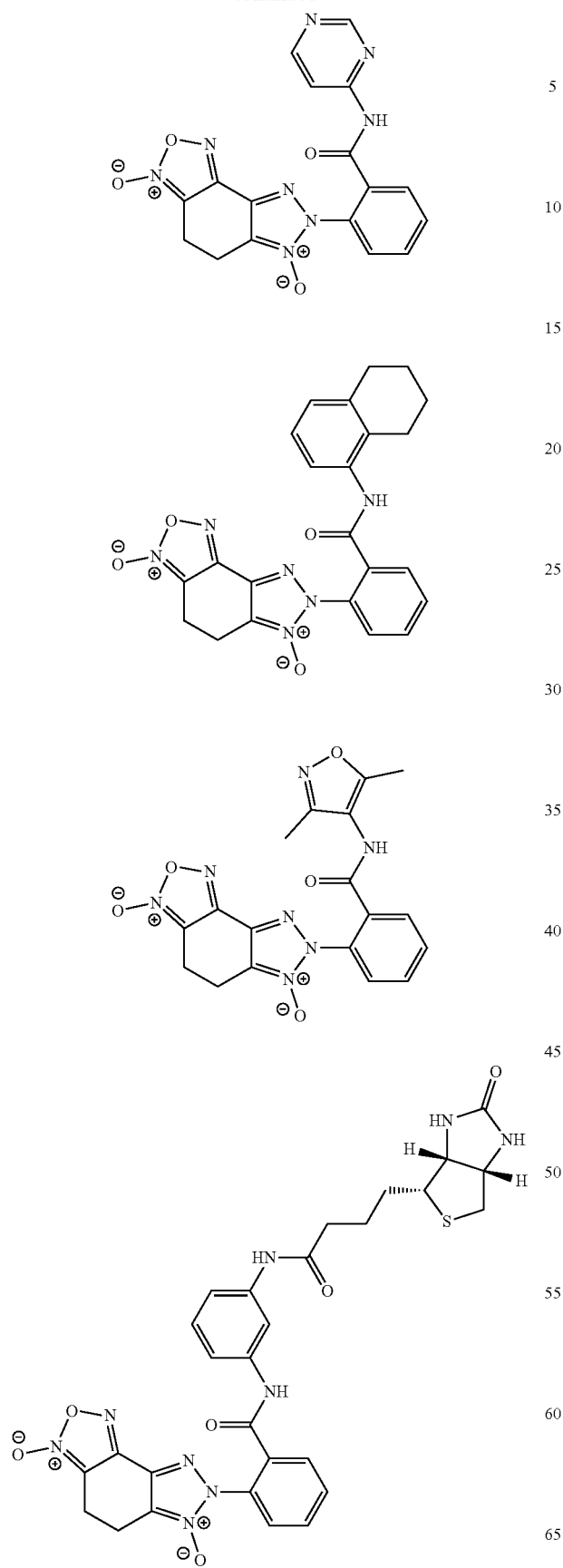
78
-continued
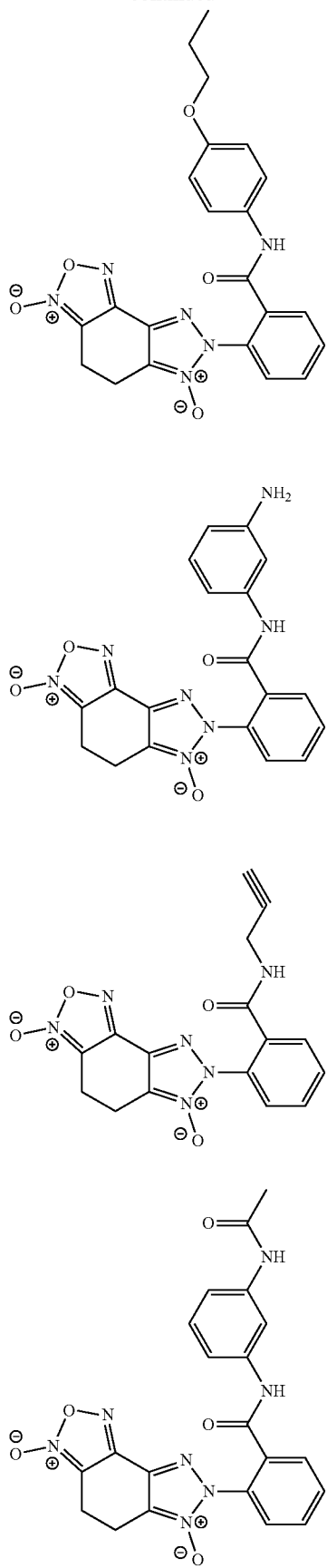

79
-continued
80
-continued
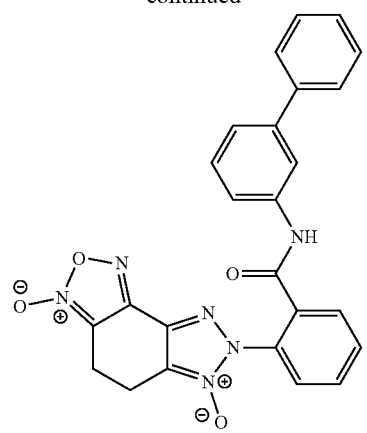
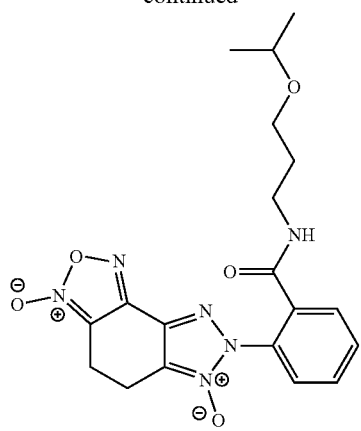
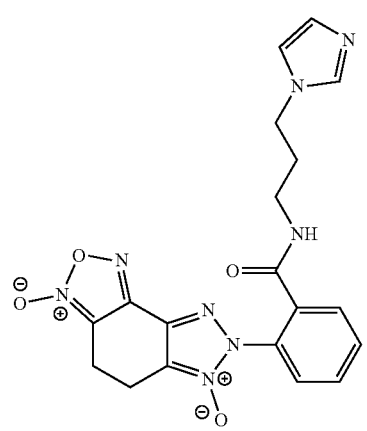
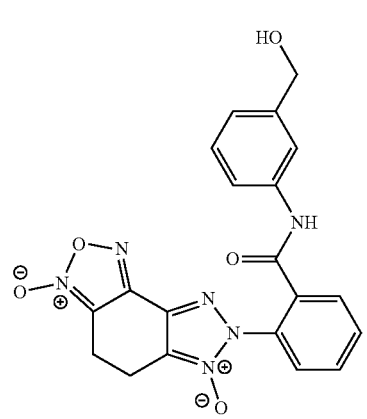
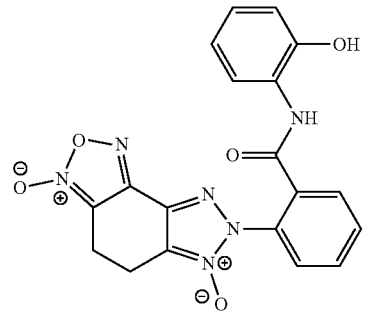

81
-continued
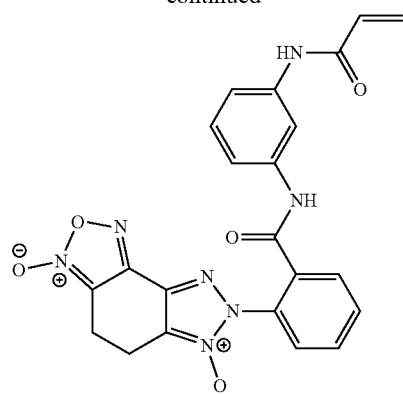
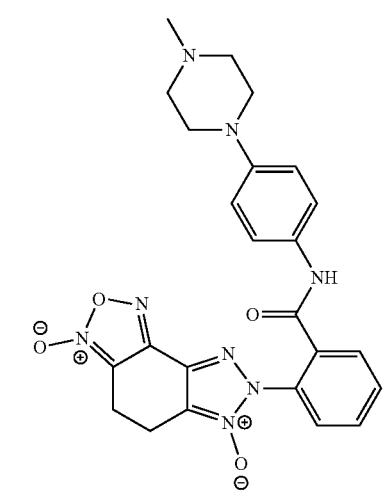
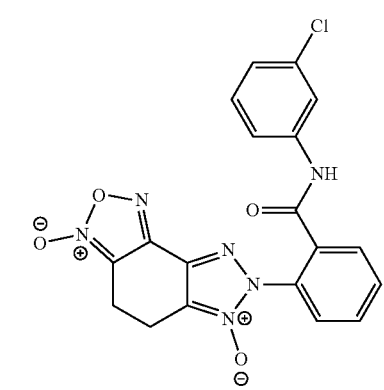
82
-continued
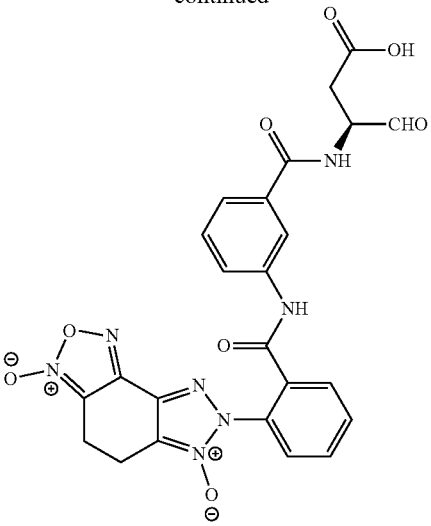
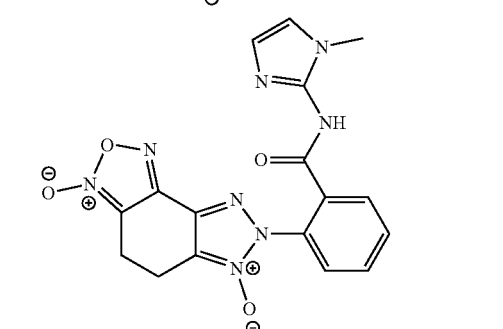
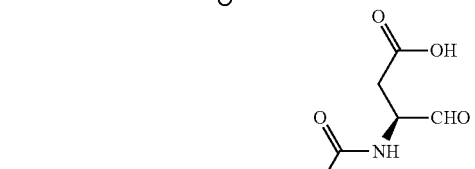
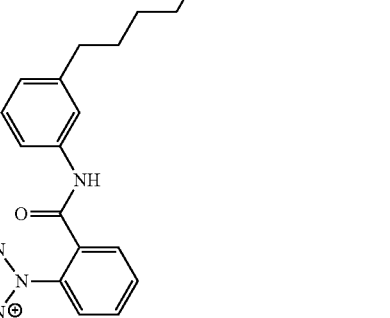
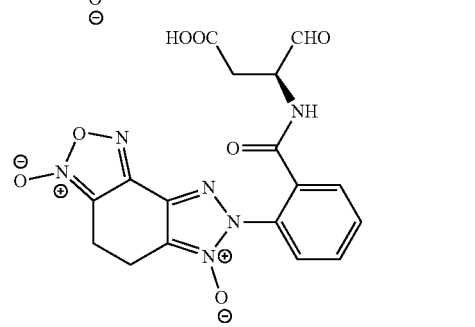

83
-continued
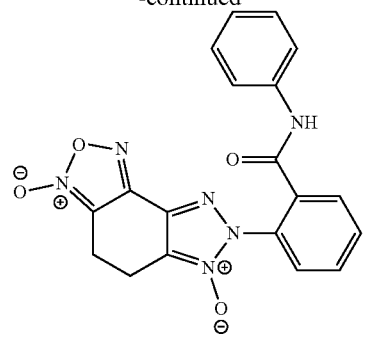
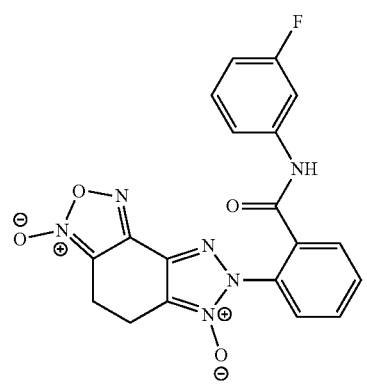
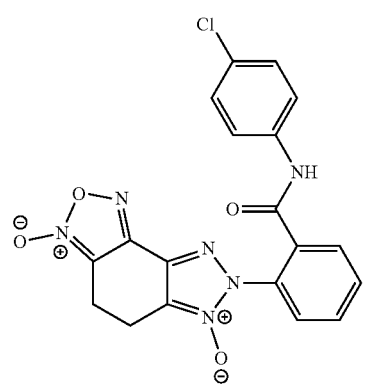
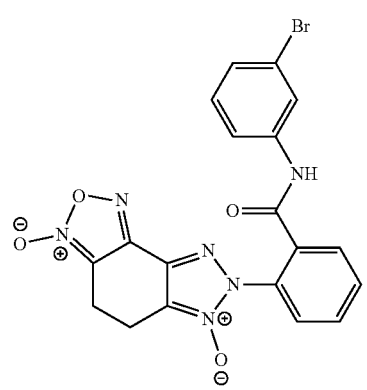
84
-continued
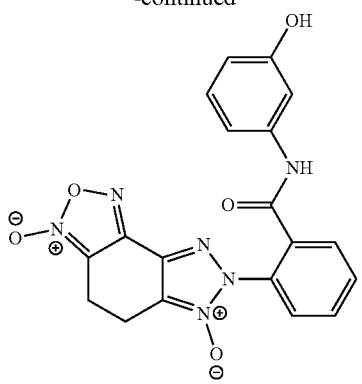
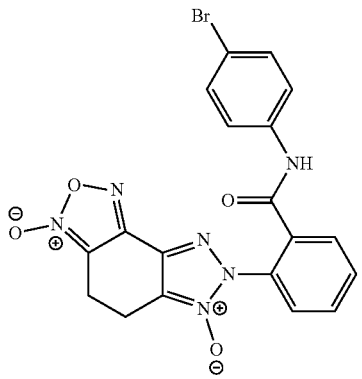
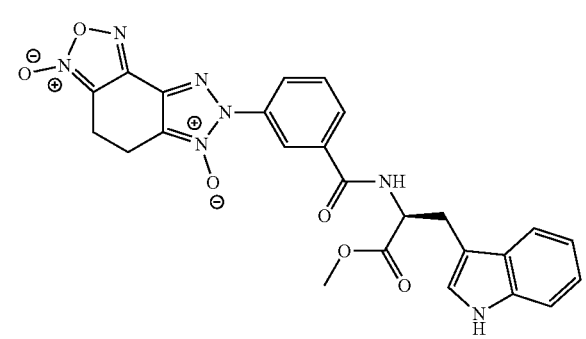
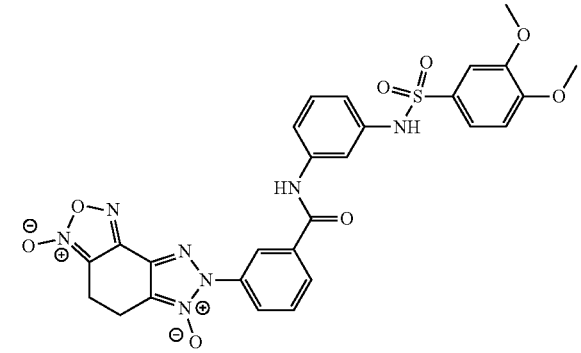

85
-continued

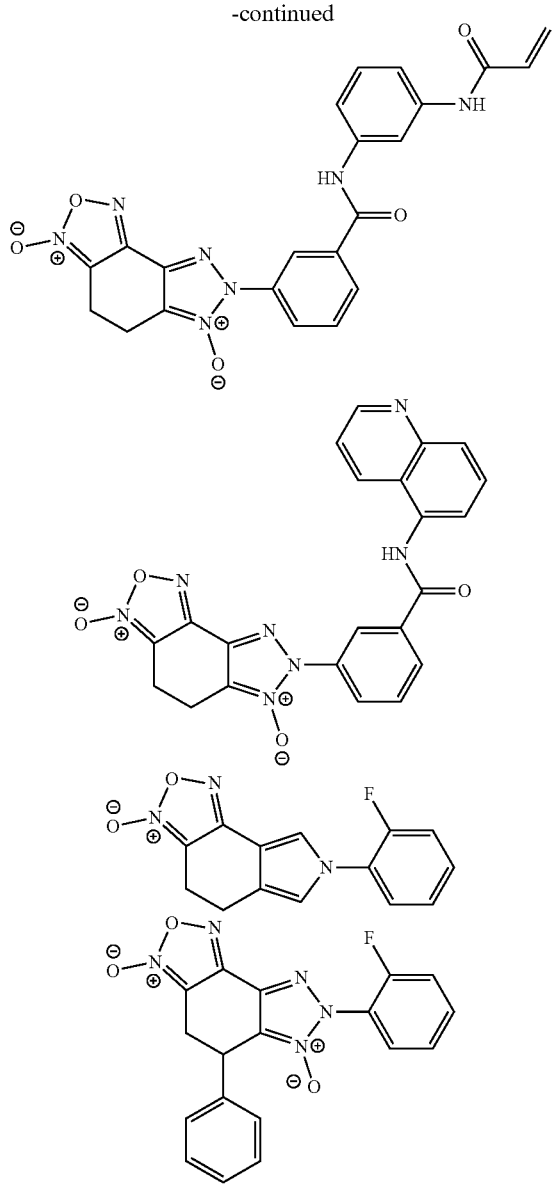

or a pharmaceutically acceptable salt, polymorph, prodrug, solvate or clathrate thereof.

Embodiment 8 relates to a pharmaceutical composition comprising at least one compound of Embodiments 1-7 and a pharmaceutically acceptable excipient.

Embodiment 9 relates to a method for treating a neurodegenerative disease, the method comprising administering a therapeutically effective amount of at least one compound of Embodiments 1-7, or a pharmaceutically acceptable salt, polymorph, prodrug, solvate or clathrate thereof, or the pharmaceutical composition of Embodiment 8, to a patient in need thereof.

Embodiment 10 relates to the method of Embodiment 9, wherein the neurodegenerative disease is Alzheimer's disease, Parkinson's disease, Huntington's disease or multiple sclerosis (MS).

Embodiment 11 relates to a method for inhibiting caspase-6 with a compound that reacts with the sulfhydryl group (SH) on cysteine 264 of caspase-6, the method comprising contacting caspase-6 with an effective amount of said compound.

86

Embodiment 12 relates to a method for treating a neurodegenerative disease, the method comprising administering to a patient in need thereof a therapeutically effective amount of at least one compound of the general formula (I):

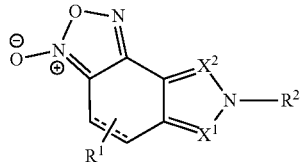

(I)

or a pharmaceutically acceptable salt, polymorph, prodrug, solvate or clathrate thereof,
wherein:
the dashed line represents a single or a double bond;
$R^1$ is H or aryl;
$R^2$ is H or aryl; and
$X^1$ and $X^2$ are each, independently, N, $N^+$—$O^-$ or $CR^3$, wherein $R^3$ is H or alkyl and only one of $X^1$ and $X^2$ can be $N^+$—$O^-$;
or a pharmaceutical composition comprising a compound of the formula (I).

What is claimed is:
1. A compound of the general formula:

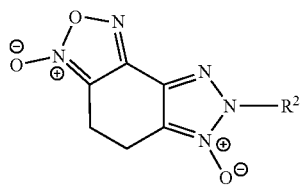

or a pharmaceutically acceptable salt or solvate thereof,
wherein:
$R^2$ is H or substituted aryl, wherein the substituent on the aryl is not $NO_2$, $CH_3$, or chloro.
2. The compound of claim 1, wherein the compound is a compound of the formula:

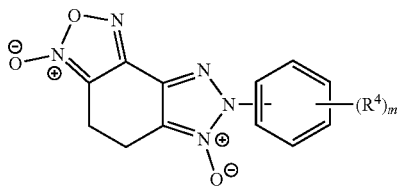

or a pharmaceutically acceptable salt or solvate thereof,
wherein:
m is an integer from 1 to 3; and
each $R^4$ is, independently, H, fluoro, iodo, bromo, alkyl, alkoxy, $N(R^5)_2$, $COR^6$, or haloalkyl, with the proviso that $R^4$ is not $CH_3$, wherein each $R^5$ is, independently, H, $S(O)_nR^7$ or acyl, wherein $R^7$ can be alkyl or aryl and n is an integer from 1 to 2, and $R^6$ is H, alkyl, alkenyl, alkynyl, aryl, heteroaryl or $N(R^8)_2$, wherein each $R^8$ is, independently, H, alkyl or aryl; or
two adjacent $R^4$ groups, together with the atoms to which they are attached, can form an aryl or a heteroaryl group.

3. The compound of claim 1, wherein the compound is a compound of the formula:

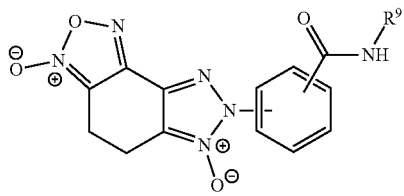

or a pharmaceutically acceptable salt or solvate thereof, wherein:
m is an integer from 1 to 3; and
$R^9$ is H, alkyl, aryl, alkenyl, alkynyl, arylalkyl or heteroarylalkyl.

4. The compound of claim 1, wherein the compound is a compound of the formula:

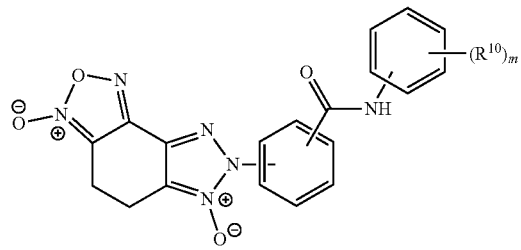

or a pharmaceutically acceptable salt or solvate thereof, wherein:
m is an integer from 1 to 3; and
$R^{10}$ is H, halo, alkyl, OH, alkoxy, aryl, alkenyl, alkynyl, arylalkyl, heteroarylalkyl, heterocyclyl, $N(R^5)_2$ or $COR^6$, wherein each $R^5$ is, independently, H, $S(O)_nR^7$ or acyl, wherein $R^7$ can be alkyl or aryl and n is an integer from 1 to 2, and $R^6$ is H, alkyl, alkenyl, alkynyl, aryl, heteroaryl or $N(R^8)_2$, wherein each $R^8$ is, independently, H, alkyl or aryl; or
two adjacent $R^{10}$ groups, together with the atoms to which they are attached, can form a cycloalkyl, aryl or a heteroaryl group.

5. The compound of claim 1, wherein the compound is a compound of the formula (If):

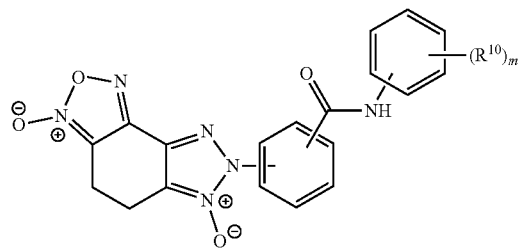

or a pharmaceutically acceptable salt or solvate thereof, wherein:
m is an integer from 1 to 3; and
$R^{10}$ is H, halo, alkyl, OH, alkoxy, aryl, alkenyl, alkynyl, arylalkyl, heteroarylalkyl, heterocyclyl, $N(R^5)_2$ or $COR^6$, wherein each $R^5$ is, independently, H, $S(O)_nR^7$ or acyl, wherein $R^7$ can be alkyl or aryl and n is an integer from 1 to 2, and $R^6$ is H, alkyl, alkenyl, alkynyl, aryl, heteroaryl or $N(R^8)_2$, wherein each $R^8$ is, independently, H, alkyl or aryl; or two adjacent $R^{10}$ groups, together with the atoms to which they are attached, can form a cycloalkyl, aryl or a heteroaryl group.

6. The compound of claim 1, wherein the compound is a compound of the formula:

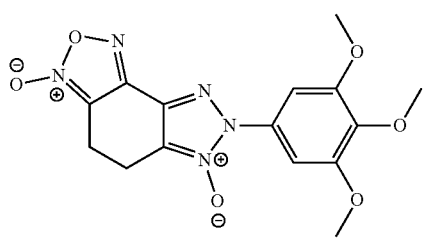

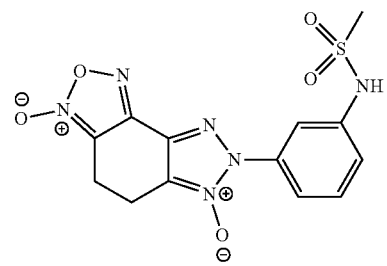

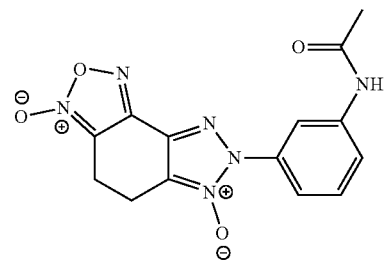

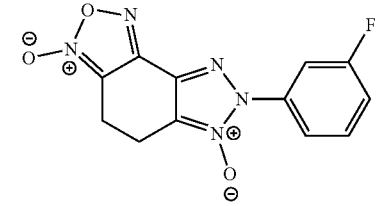

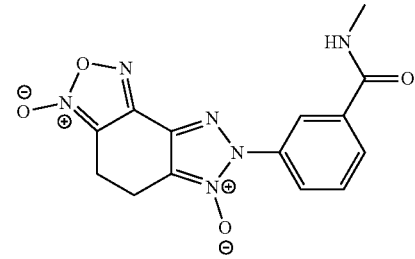

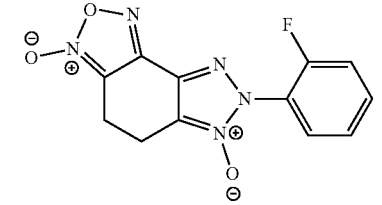

89
-continued
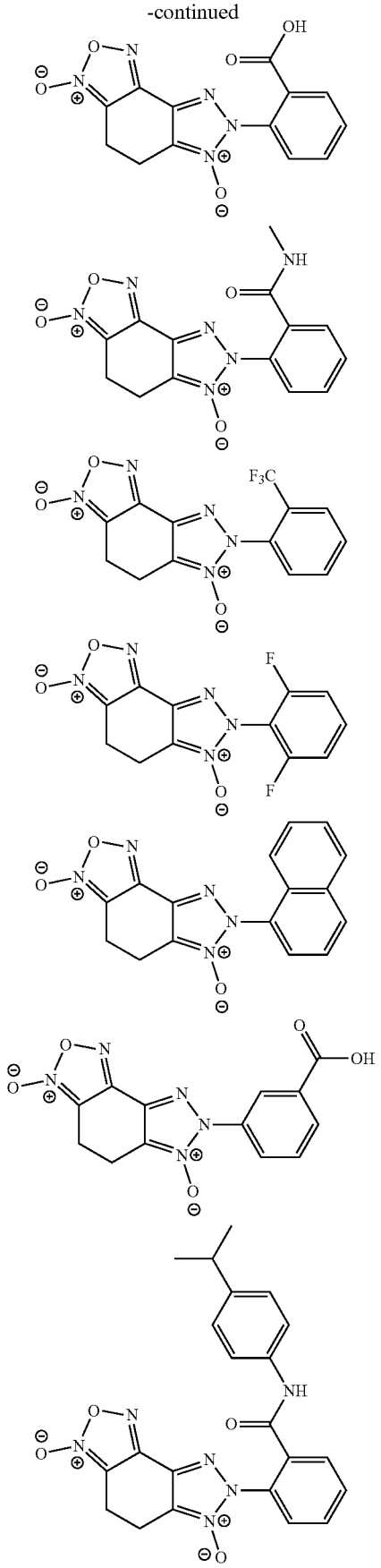
90
-continued
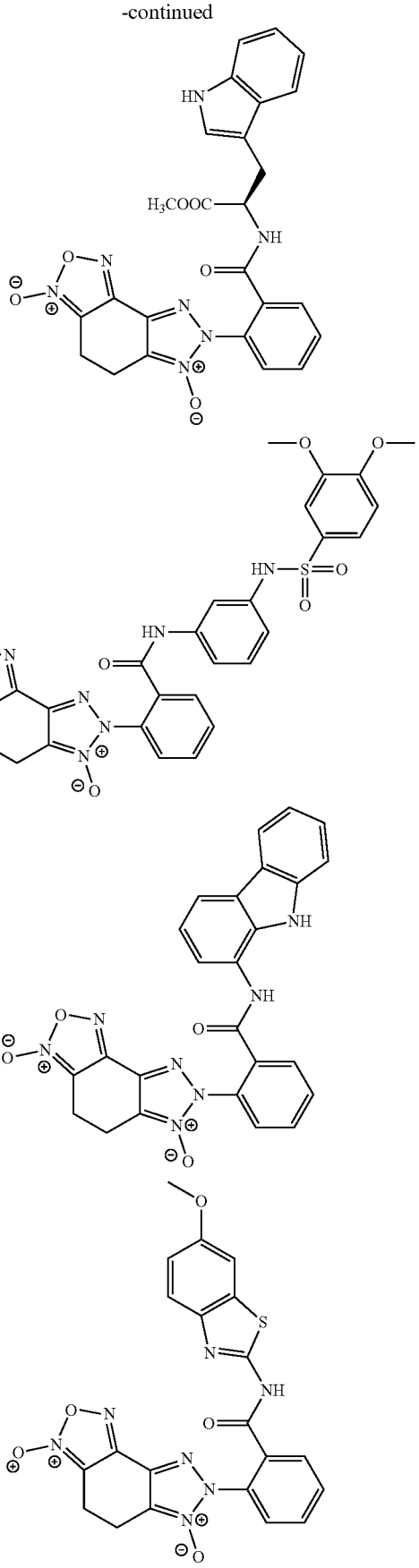

91
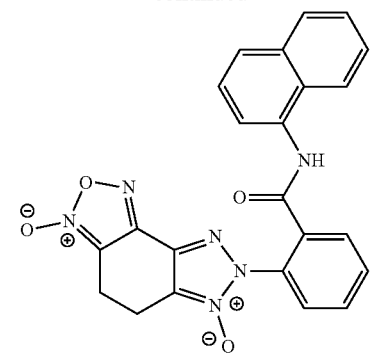
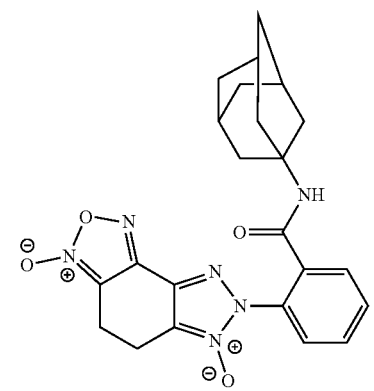
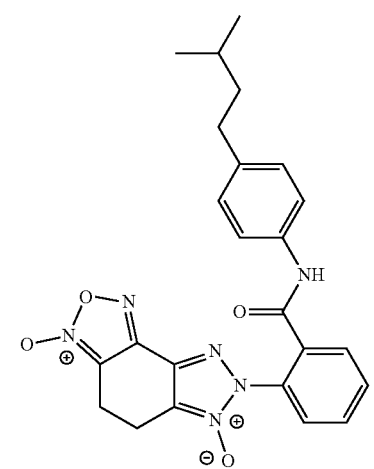
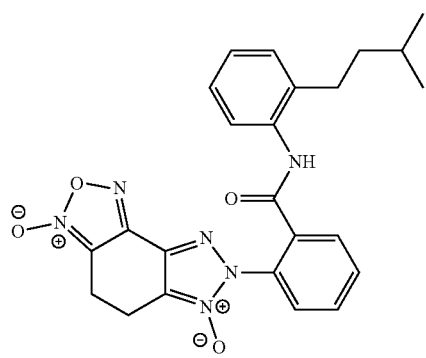
92
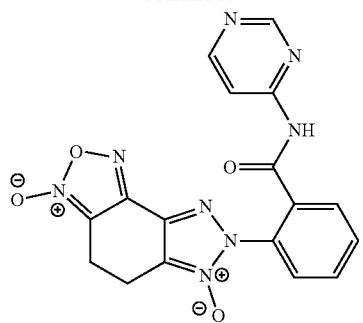
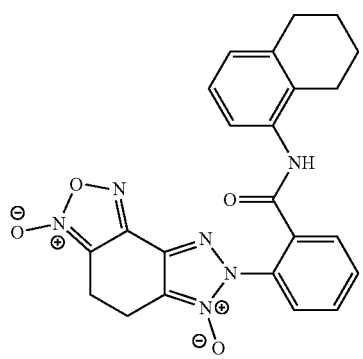
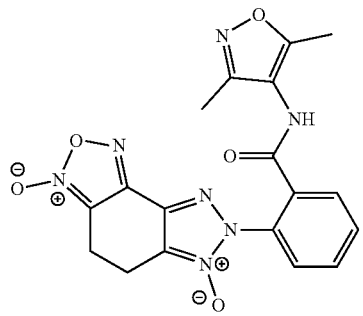
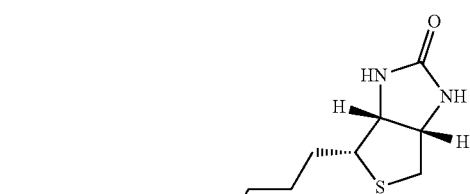
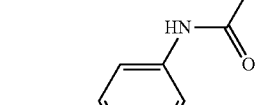
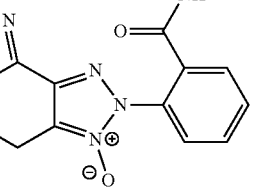

93
-continued
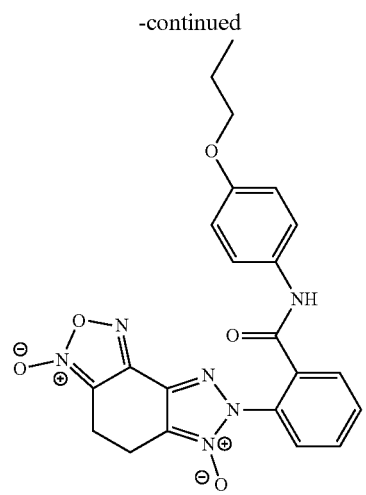
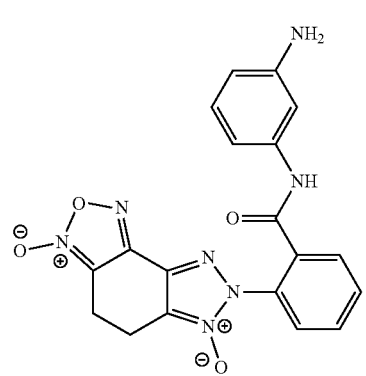
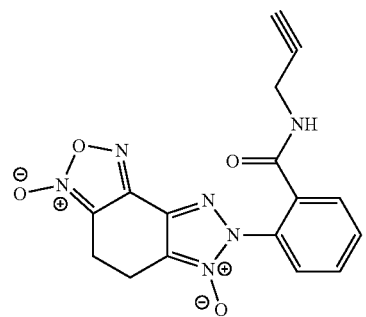
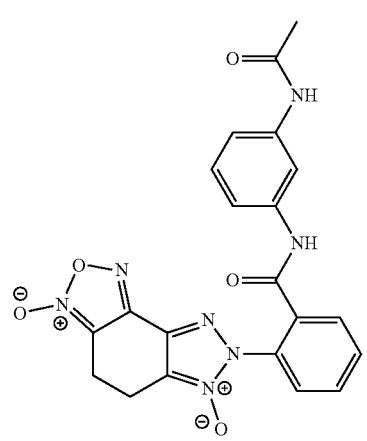
94
-continued
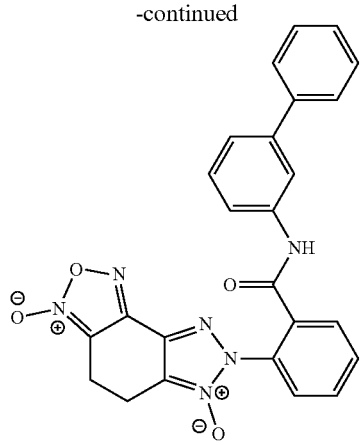
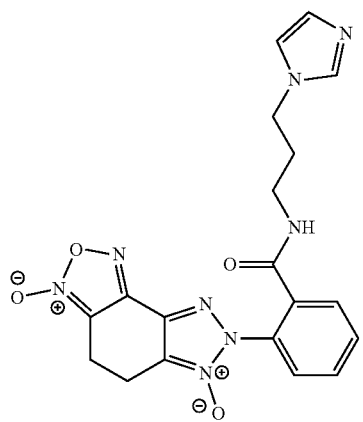
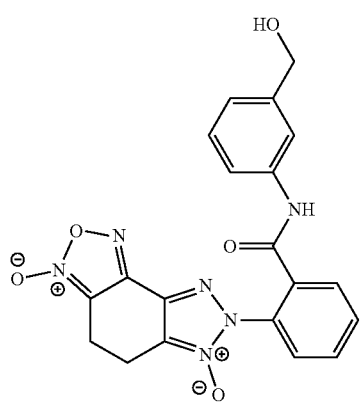
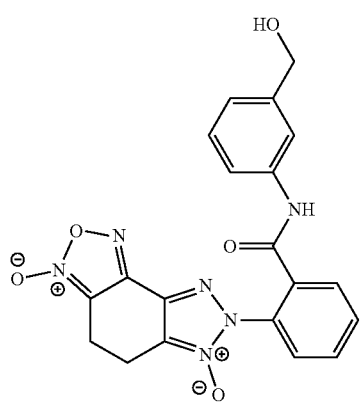

95
-continued
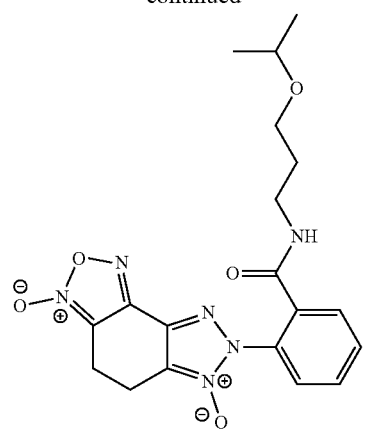
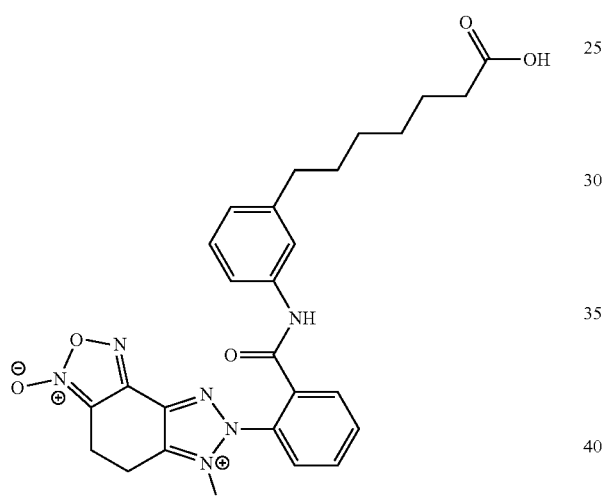
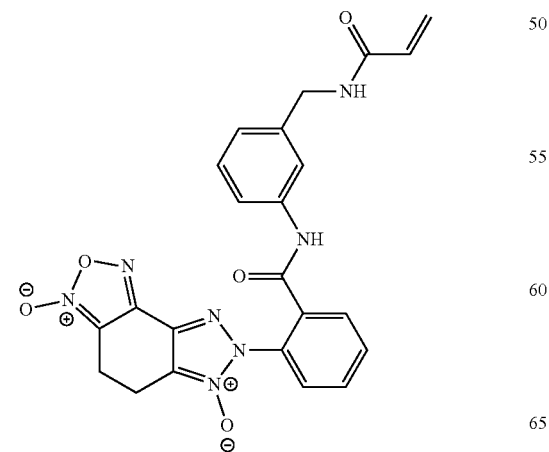
96
-continued
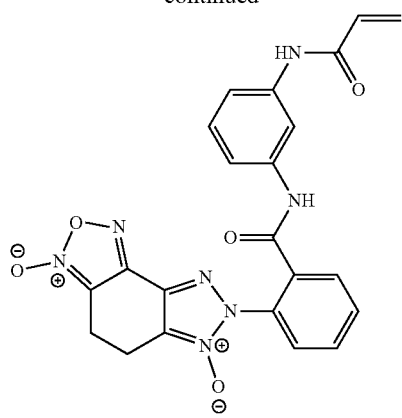
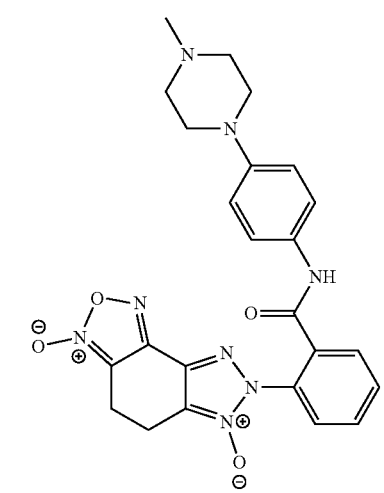
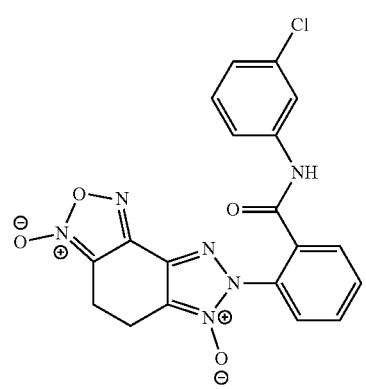

97
-continued
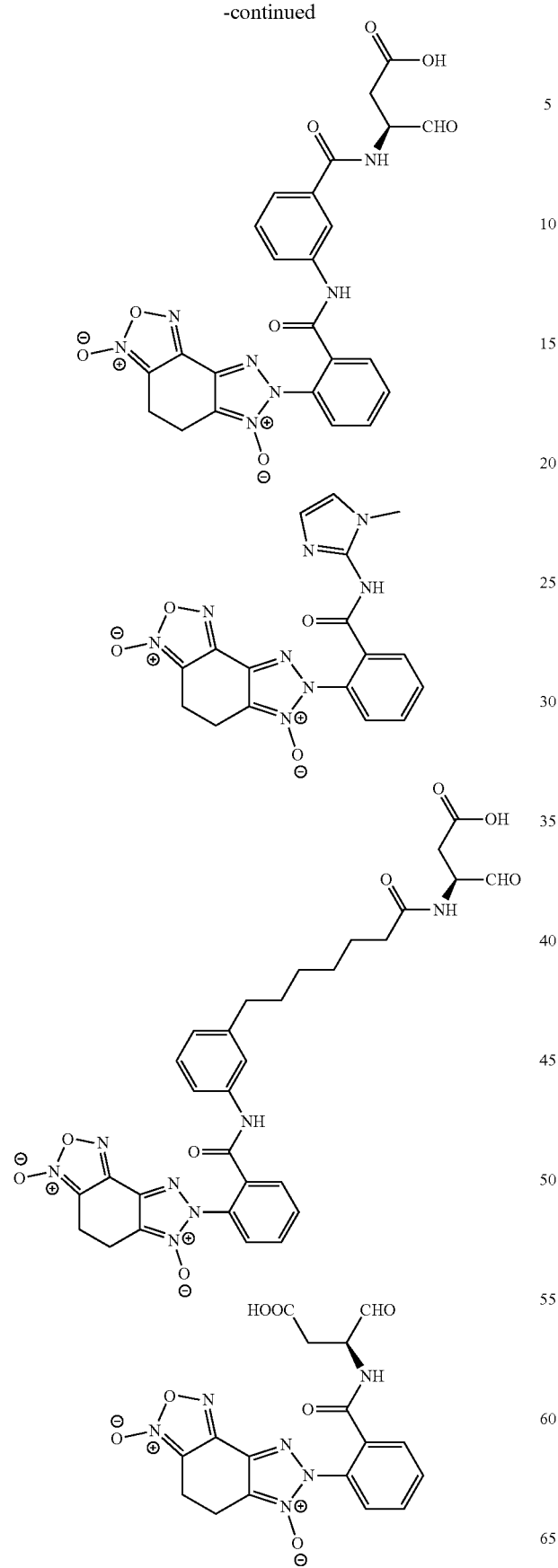
98
-continued
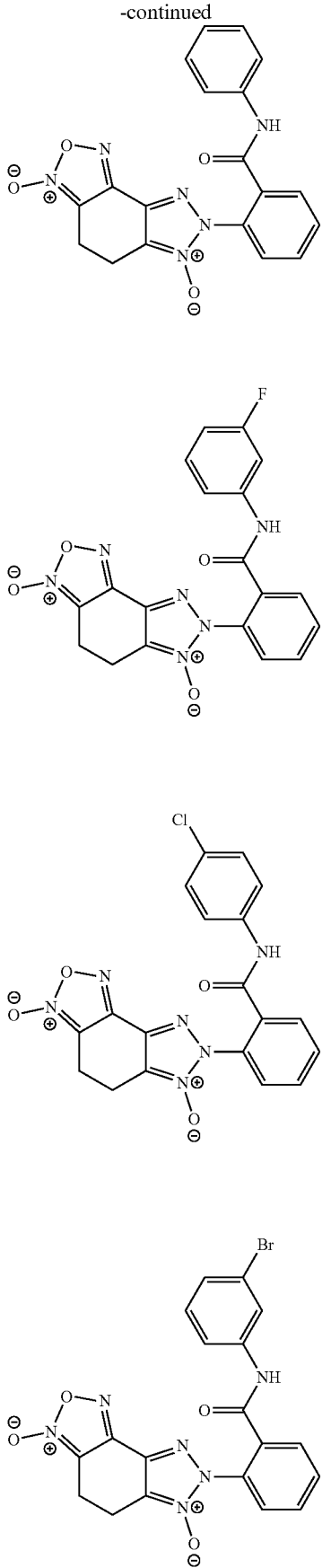

99
-continued
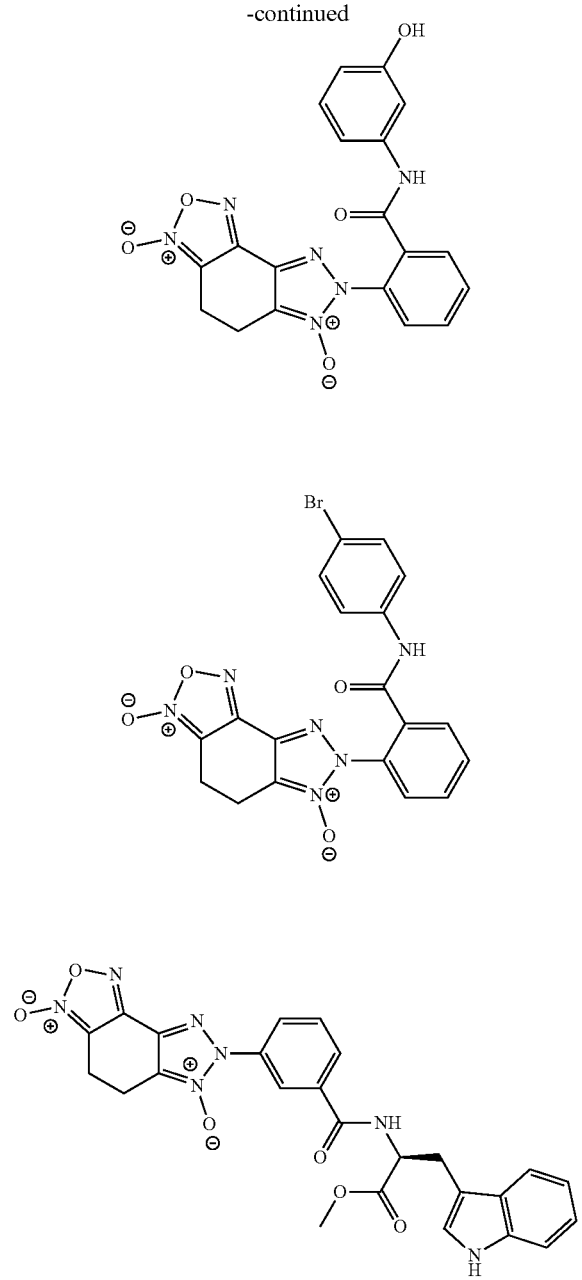
100
-continued
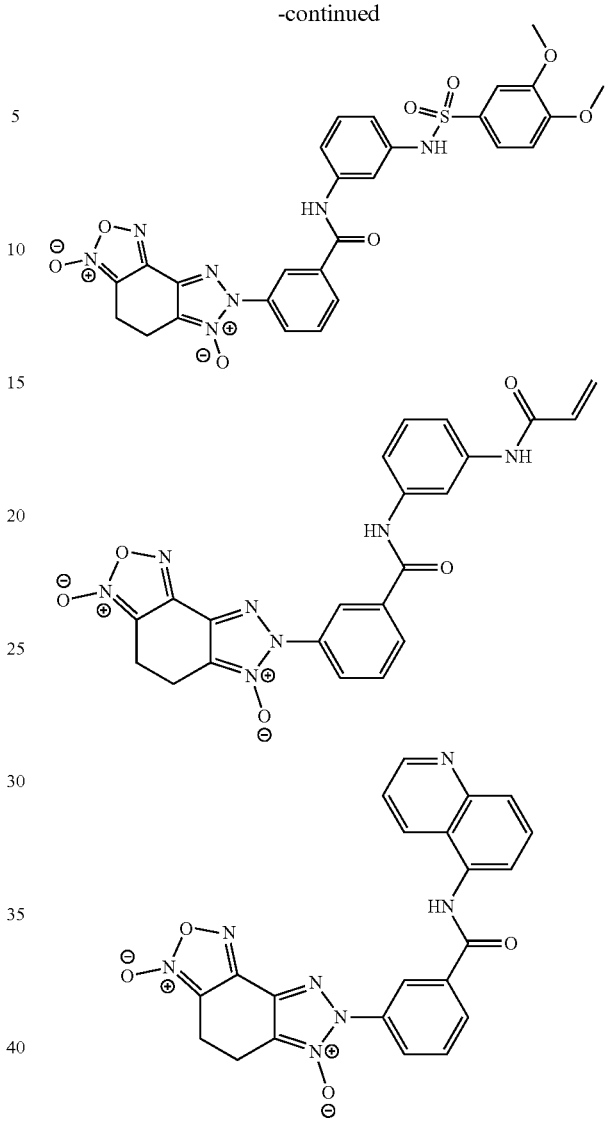
or a pharmaceutically acceptable salt or solvate thereof.
7. A pharmaceutical composition comprising at least one compound of claim 1 and a pharmaceutically acceptable excipient.
* * * * *